US011439166B2

United States Patent
Varadan et al.

(10) Patent No.: US 11,439,166 B2
(45) Date of Patent: Sep. 13, 2022

(54) GROUND MEAT REPLICAS

(71) Applicant: Impossible Foods Inc., Redwood City, CA (US)

(72) Inventors: Ranjani Varadan, Fremont, CA (US); Sergey Solomatin, Mountain View, CA (US); Celeste Holz-Schietinger, East Palo Alto, CA (US); Elysia Cohn, San Carlos, CA (US); Ariel Klapholz-Brown, San mateo, CA (US); Jennifer Woan-Yi Shiu, San Francisco, CA (US); Aniket Kale, Foster City, CA (US); Jessica Karr, San Francisco, CA (US); Rachel Fraser, San Francisco, CA (US)

(73) Assignee: Impossible Foods Inc., Redwood City, CA (US)

( * ) Notice: Subject to any disclaimer, the term of this patent is extended or adjusted under 35 U.S.C. 154(b) by 0 days.

(21) Appl. No.: 17/531,460

(22) Filed: Nov. 19, 2021

(65) Prior Publication Data

US 2022/0095654 A1    Mar. 31, 2022

Related U.S. Application Data

(63) Continuation of application No. 16/238,698, filed on Jan. 3, 2019, which is a continuation of application No. 15/300,339, filed as application No. PCT/US2015/023679 on Mar. 31, 2015, now Pat. No. 10,172,380.

(60) Provisional application No. 62/058,230, filed on Oct. 1, 2014, provisional application No. 61/973,181, filed on Mar. 31, 2014.

(51) Int. Cl.
| | |
|---|---|
| *A23L 13/40* | (2016.01) |
| *C12N 1/16* | (2006.01) |
| *C07K 14/805* | (2006.01) |
| *C12N 9/10* | (2006.01) |
| *C12N 9/88* | (2006.01) |
| *C12N 15/81* | (2006.01) |

(52) U.S. Cl.
CPC ............ *A23L 13/43* (2016.08); *A23L 13/422* (2016.08); *A23L 13/426* (2016.08); *A23V 2002/00* (2013.01); *C07K 14/805* (2013.01); *C12N 1/165* (2021.05); *C12N 9/1029* (2013.01); *C12N 9/88* (2013.01); *C12N 15/815* (2013.01)

(58) Field of Classification Search
None
See application file for complete search history.

(56) References Cited

U.S. PATENT DOCUMENTS

| | | | |
|---|---|---|---|
| 2,934,435 | A | 4/1960 | May |
| 2,934,436 | A | 4/1960 | May |
| 2,934,437 | A | 4/1960 | Morton et al. |
| 2,955,041 | A | 10/1960 | Broderick |
| 3,157,516 | A | 11/1964 | Huber |
| 3,271,167 | A | 9/1966 | Perret |
| 3,316,099 | A | 4/1967 | Hoersch |
| 3,365,306 | A | 1/1968 | Perret |
| 3,394,015 | A | 7/1968 | Giacino et al. |
| 3,394,016 | A | 7/1968 | Bidmead |
| 3,394,017 | A | 7/1968 | Giacino et al. |
| 3,480,447 | A | 11/1969 | Hack |
| 3,493,395 | A | 2/1970 | Soeters |
| 3,519,437 | A | 7/1970 | Giacino et al. |
| 3,524,747 | A | 8/1970 | O'Hara |
| 3,532,514 | A | 10/1970 | May |
| 3,532,515 | A | 10/1970 | Broderick |
| 3,578,465 | A | 5/1971 | van der Zijden |
| 3,615,600 | A | 10/1971 | Zevenaar |
| 3,620,772 | A | 11/1971 | Nagayoshi |
| 3,642,497 | A | 2/1972 | Gunther |
| 3,645,753 | A | 2/1972 | Gasser |
| 3,645,754 | A | 2/1972 | Wiener |
| 3,658,550 | A | 4/1972 | Hawley |
| 3,660,114 | A | 5/1972 | Thomas |
| 3,689,289 | A | 9/1972 | Perret |
| 3,693,533 | A | 9/1972 | Liepa |
| 3,697,295 | A | 10/1972 | van der Ouweland |
| 3,716,379 | A | 2/1973 | de la Potterie |
| 3,716,380 | A | 2/1973 | de la Potterie |
| 3,719,499 | A | 3/1973 | Hai et al. |
| 3,741,775 | A | 6/1973 | Lee |
| 3,761,287 | A | 9/1973 | Jaeggi et al. |
| 3,804,953 | A | 4/1974 | Bentz et al. |
| 3,829,582 | A | 8/1974 | Guadagni et al. |
| 3,840,674 | A | 10/1974 | Joseph et al. |
| 3,857,970 | A | 12/1974 | Tsumura |
| 3,870,801 | A | 3/1975 | Tombs |
| 3,879,561 | A | 4/1975 | Smith et al. |
| 3,881,022 | A | 4/1975 | Gasser |

(Continued)

FOREIGN PATENT DOCUMENTS

| | | |
|---|---|---|
| CN | 1252231 | 5/2000 |
| CN | 1301811 | 7/2001 |

(Continued)

OTHER PUBLICATIONS

U.S. Appl. No. 61/347,193, filed May 21, 2010, Crane et al.

(Continued)

*Primary Examiner* — Kagnew H Gebreyesus
(74) *Attorney, Agent, or Firm* — Fish & Richardson P.C.

(57) ABSTRACT

This document relates to ground meat replicas, and more particularly to plant-based products that mimic ground meat, including the fibrousness, heterogeneity in texture, beefy flavor, and red-to-brown color transition during cooking of ground meat.

14 Claims, 1 Drawing Sheet

(56) References Cited

U.S. PATENT DOCUMENTS

| | | |
|---|---|---|
| 3,928,643 A | 12/1975 | Ishiguro et al. |
| 3,930,046 A | 12/1975 | Baugher |
| 3,966,985 A | 6/1976 | Jonas |
| 3,973,043 A | 8/1976 | Lynn |
| 4,045,587 A | 8/1977 | Katz et al. |
| 4,066,793 A | 1/1978 | Eguchi |
| 4,076,852 A | 2/1978 | Van Delft et al. |
| 4,094,997 A | 6/1978 | Aishima et al. |
| 4,098,913 A | 7/1978 | Baugher |
| 4,132,809 A | 1/1979 | Desrosier |
| 4,161,550 A | 7/1979 | Bernhardt et al. |
| 4,165,391 A | 8/1979 | Corbett nee Rolison |
| 4,197,324 A | 4/1980 | Ziminski et al. |
| 4,218,487 A | 8/1980 | Jaeggi |
| 4,324,807 A | 4/1982 | Kim et al. |
| 4,411,915 A | 10/1983 | Eriksson |
| 4,435,438 A | 3/1984 | Lehnhardt et al. |
| 4,604,290 A | 8/1986 | Lee et al. |
| 4,994,285 A | 2/1991 | Hisano et al. |
| 5,039,543 A | 8/1991 | Lee et al. |
| 5,055,310 A | 10/1991 | Nonaka et al. |
| 5,264,239 A | 11/1993 | Cornet et al. |
| 5,443,852 A | 8/1995 | Shahidi et al. |
| 5,597,594 A | 1/1997 | Matsuura et al. |
| 5,650,554 A | 7/1997 | Moloney et al. |
| 5,753,295 A | 5/1998 | Goldman |
| 5,807,601 A | 9/1998 | Carpenter et al. |
| 5,856,452 A | 1/1999 | Moloney et al. |
| 5,922,392 A | 7/1999 | Kelly et al. |
| 6,093,424 A | 7/2000 | Han et al. |
| 6,146,645 A | 11/2000 | Deckers et al. |
| 6,183,762 B1 | 2/2001 | Deckers et al. |
| 6,210,742 B1 | 4/2001 | Deckers et al. |
| 6,228,418 B1 | 5/2001 | Gluck |
| 6,242,036 B1 | 6/2001 | Han et al. |
| 6,261,827 B1 | 7/2001 | Elrod et al. |
| 6,287,620 B1 | 9/2001 | Van Den Ouweland et al. |
| 6,372,234 B1 | 4/2002 | Deckers et al. |
| 6,372,961 B1 | 4/2002 | Tarczynski |
| 6,379,738 B1 | 4/2002 | Dingman et al. |
| 6,383,531 B1 | 5/2002 | Gottemoller |
| 6,399,135 B2 | 6/2002 | Gottemoller |
| 6,413,569 B1 | 7/2002 | Borders et al. |
| 6,416,797 B1 | 7/2002 | Han et al. |
| 6,420,148 B2 | 7/2002 | Yamaguchi |
| 6,495,184 B1 | 12/2002 | Zheng et al. |
| 6,495,187 B1 | 12/2002 | Borders et al. |
| 6,509,453 B1 | 1/2003 | Moloney |
| 6,582,710 B2 | 6/2003 | Deckers et al. |
| 6,596,287 B2 | 7/2003 | Deckers et al. |
| 6,599,513 B2 | 7/2003 | Deckers et al. |
| 6,692,788 B1 | 2/2004 | Mottram et al. |
| 6,761,914 B2 | 7/2004 | Deckers et al. |
| 6,908,634 B2 | 6/2005 | Hwang |
| 6,936,749 B1 | 8/2005 | Guy et al. |
| 7,052,879 B2 | 5/2006 | Shaw et al. |
| 7,332,587 B2 | 2/2008 | Moloney |
| 7,407,786 B2 | 8/2008 | Giver et al. |
| 7,479,472 B1 | 1/2009 | Harbury et al. |
| 7,507,428 B2 | 3/2009 | Numata et al. |
| 7,585,645 B2 | 9/2009 | Deckers et al. |
| 7,622,290 B2 | 11/2009 | Brunstedt et al. |
| 7,666,618 B2 | 2/2010 | Miasnikov et al. |
| 7,666,628 B2 | 2/2010 | Moloney |
| 7,674,953 B2 | 3/2010 | Mulet Salort et al. |
| 7,709,044 B2 | 5/2010 | Ishimoto |
| 7,807,870 B2 | 10/2010 | Geigenberger et al. |
| 7,931,925 B2 | 4/2011 | Nielsen |
| 8,012,732 B2 | 9/2011 | Brunstedt et al. |
| 8,021,695 B2 | 9/2011 | Gruber et al. |
| 8,188,415 B2 | 5/2012 | Kats et al. |
| 8,304,522 B2 | 11/2012 | Kungitani |
| 8,597,694 B2 | 12/2013 | Guth et al. |
| 9,011,949 B2 | 4/2015 | Brown et al. |
| 9,085,766 B2 | 7/2015 | Crane et al. |
| 9,700,067 B2 | 7/2017 | Fraser |
| 9,808,029 B2 | 11/2017 | Fraser et al. |
| 9,826,772 B2 | 11/2017 | Fraser et al. |
| 9,943,096 B2 | 4/2018 | Fraser et al. |
| 10,039,306 B2 | 8/2018 | Vrljic et al. |
| 10,172,380 B2 | 1/2019 | Varadan et al. |
| 10,172,381 B2 | 1/2019 | Vrljic et al. |
| 2001/0024677 A1 | 9/2001 | Bringe |
| 2001/0049132 A1 | 12/2001 | Kringelum et al. |
| 2002/0034570 A1 | 3/2002 | Krammer et al. |
| 2003/0198700 A1 | 10/2003 | Gruber |
| 2003/0212281 A1 | 11/2003 | Sinha et al. |
| 2003/0224476 A1 | 12/2003 | Chou |
| 2004/0151778 A1 | 8/2004 | Richard et al. |
| 2004/0161513 A1 | 8/2004 | Akashe et al. |
| 2005/0037111 A1 | 2/2005 | Berry |
| 2006/0035003 A1 | 2/2006 | McMindes et al. |
| 2006/0035006 A1 | 2/2006 | McMindes et al. |
| 2006/0204644 A1 | 9/2006 | Cavallini et al. |
| 2006/0233721 A1 | 10/2006 | Tamarkin et al. |
| 2007/0269567 A1 | 11/2007 | McMindes et al. |
| 2007/0269571 A1 | 11/2007 | Akita et al. |
| 2007/0269583 A1 | 11/2007 | McMindes et al. |
| 2008/0026128 A1 | 1/2008 | Yamaguchi |
| 2008/0226810 A1 | 9/2008 | Passe et al. |
| 2008/0254168 A1 | 10/2008 | Mueller et al. |
| 2008/0254199 A1 | 10/2008 | Orcutt et al. |
| 2008/0268112 A1 | 10/2008 | Rolan et al. |
| 2008/0292749 A1 | 11/2008 | Goodwins et al. |
| 2008/0299254 A1 | 12/2008 | Kim et al. |
| 2009/0148558 A1 | 6/2009 | Kim et al. |
| 2009/0264520 A1 | 10/2009 | Bhagat et al. |
| 2009/0274817 A1 | 11/2009 | Yamaguchi et al. |
| 2010/0074998 A1 | 3/2010 | Vega et al. |
| 2010/0136201 A1 | 6/2010 | Bigeard et al. |
| 2010/0196575 A1 | 8/2010 | Sanchez |
| 2010/0233347 A1 | 9/2010 | Uhrhan |
| 2010/0249560 A1 | 9/2010 | Levinson et al. |
| 2010/0281765 A1 | 11/2010 | Schwartz |
| 2010/0310738 A1 | 12/2010 | Ludwig |
| 2010/0311950 A1 | 12/2010 | Kugitani |
| 2011/0008502 A1 | 1/2011 | Hosomi et al. |
| 2011/0064847 A1 | 3/2011 | Miwa et al. |
| 2011/0064862 A1 | 3/2011 | McCready et al. |
| 2011/0081386 A1 | 4/2011 | Guth et al. |
| 2011/0081435 A1 | 4/2011 | Guth et al. |
| 2011/0117180 A1 | 5/2011 | Yan et al. |
| 2011/0286992 A1 | 11/2011 | Gruber et al. |
| 2011/0287467 A1 | 11/2011 | Crane et al. |
| 2011/0288389 A9 | 11/2011 | Levinson et al. |
| 2012/0059150 A1 | 3/2012 | Moloney et al. |
| 2012/0093994 A1 | 4/2012 | Hsieh et al. |
| 2013/0004617 A1 | 1/2013 | Zhang et al. |
| 2014/0011347 A1 | 1/2014 | Yerushalmi et al. |
| 2014/0220217 A1 | 8/2014 | Brown et al. |
| 2015/0289541 A1 | 10/2015 | Brown et al. |
| 2015/0296834 A1 | 10/2015 | Geistlinger et al. |
| 2015/0296835 A1 | 10/2015 | Anderson et al. |
| 2015/0366233 A1 | 12/2015 | Brown et al. |
| 2017/0105438 A1 | 4/2017 | Ajami et al. |
| 2017/0172169 A1 | 6/2017 | Grzanich |
| 2017/0188612 A1 | 7/2017 | Varadan et al. |
| 2017/0321204 A1 | 11/2017 | Kale et al. |
| 2018/0027851 A1 | 2/2018 | Vrlijic et al. |
| 2018/0168209 A1 | 6/2018 | Fraser et al. |
| 2018/0192680 A1 | 7/2018 | Fraser et al. |
| 2018/0199605 A1 | 7/2018 | Fraser et al. |
| 2018/0199606 A1 | 7/2018 | Fraser et al. |
| 2018/0368453 A1 | 12/2018 | Brown et al. |
| 2019/0008192 A1 | 1/2019 | Brown et al. |
| 2019/0116855 A1 | 4/2019 | Vrljic et al. |
| 2019/0133162 A1 | 5/2019 | Varadan et al. |
| 2019/0133163 A1 | 5/2019 | Varadan et al. |
| 2019/0200658 A1 | 7/2019 | Vrljic et al. |

FOREIGN PATENT DOCUMENTS

| | | |
|---|---|---|
| CN | 1407108 | 4/2003 |
| CN | 1466903 | 1/2004 |

(56) References Cited

FOREIGN PATENT DOCUMENTS

| | | |
|---|---|---|
| CN | 1557188 | 12/2004 |
| CN | 1593223 | 3/2005 |
| CN | 1634524 | 7/2005 |
| CN | 101138405 | 3/2008 |
| CN | 101156632 | 4/2008 |
| CN | 101489422 | 7/2009 |
| CN | 101541187 | 9/2009 |
| CN | 101606574 | 12/2009 |
| CN | 101861895 | 10/2010 |
| CN | 101897418 | 12/2010 |
| CN | 102440302 | 5/2012 |
| CN | 102578544 | 7/2012 |
| CN | 102835460 | 12/2012 |
| DE | 102007061256 | 6/2009 |
| DE | 202011002097 | 3/2011 |
| EP | 0136428 | 4/1985 |
| EP | 0500132 | 8/1992 |
| EP | 0815736 | 1/1998 |
| EP | 1166653 | 1/2002 |
| EP | 1254601 | 11/2002 |
| EP | 0680751 | 11/2004 |
| EP | 1529444 | 5/2005 |
| EP | 1759593 | 3/2007 |
| EP | 1361264 | 4/2007 |
| EP | 1952695 | 8/2008 |
| EP | 2138052 | 12/2009 |
| EP | 2943072 | 11/2015 |
| GB | 836694 | 6/1960 |
| GB | 858333 | 1/1961 |
| GB | 858660 | 1/1961 |
| GB | 1023334 | 3/1966 |
| GB | 1032334 | 6/1966 |
| GB | 1069104 | 5/1967 |
| GB | 1076948 | 7/1967 |
| GB | 1082504 | 9/1967 |
| GB | 1084619 | 9/1967 |
| GB | 1099711 | 1/1968 |
| GB | 1115610 | 5/1968 |
| GB | 1126889 | 9/1968 |
| GB | 1130631 | 10/1968 |
| GB | 1135123 | 11/1968 |
| GB | 1146337 | 3/1969 |
| GB | 1148449 | 4/1969 |
| GB | 1182976 | 3/1970 |
| GB | 1198398 | 7/1970 |
| GB | 1205882 | 9/1970 |
| GB | 1206265 | 9/1970 |
| GB | 1221482 | 2/1971 |
| GB | 1224989 | 3/1971 |
| GB | 1232719 | 5/1971 |
| GB | 1234927 | 6/1971 |
| GB | 1256462 | 12/1971 |
| GB | 1283913 | 8/1972 |
| GB | 1284357 | 8/1972 |
| GB | 1302525 | 1/1973 |
| GB | 1311638 | 3/1973 |
| GB | 1313830 | 4/1973 |
| GB | 1318460 | 5/1973 |
| GB | 1325335 | 8/1973 |
| GB | 1357091 | 6/1974 |
| GB | 1364747 | 8/1974 |
| GB | 1382335 | 1/1975 |
| GB | 1384332 | 2/1975 |
| GB | 1447730 | 8/1976 |
| GB | 1471907 | 4/1977 |
| GB | 1515961 | 6/1978 |
| GB | 1515962 | 6/1978 |
| GB | 1525541 | 9/1978 |
| GB | 2016255 | 9/1979 |
| JP | S4222194 | 10/1942 |
| JP | S4939824 | 10/1974 |
| JP | S5163971 | 10/1975 |
| JP | S53115846 | 10/1978 |
| JP | S54122766 | 9/1979 |
| JP | S5959151 | 4/1984 |
| JP | S6283842 | 4/1987 |
| JP | H08140627 | 6/1996 |
| JP | H08173024 | 7/1996 |
| JP | H08289761 | 11/1996 |
| JP | H0970272 | 3/1997 |
| JP | H11508448 | 7/1999 |
| JP | 2001037434 | 2/2001 |
| JP | 2001061415 | 3/2001 |
| JP | 2001346533 | 12/2001 |
| JP | 2002101835 | 4/2002 |
| JP | 2005021163 | 1/2005 |
| JP | 2005530483 | 10/2005 |
| JP | 2009516522 | 4/2009 |
| JP | 2009171877 | 8/2009 |
| JP | 2009284893 | 12/2009 |
| JP | 2010512788 | 4/2010 |
| JP | 2010523125 | 7/2010 |
| JP | 2010200627 | 9/2010 |
| JP | 2011000073 | 1/2011 |
| JP | 2012016336 | 1/2012 |
| JP | 2013192528 | 9/2013 |
| JP | 2014113112 | 6/2014 |
| JP | 2014520544 | 8/2014 |
| KR | 100733589 | 6/2007 |
| KR | 1020090009990 | 1/2009 |
| RU | 2144293 | 1/2000 |
| RU | 2274003 | 4/2006 |
| RU | 2010137628 | 3/2012 |
| SU | 291395 | 6/1971 |
| SU | 301014 | 1/1974 |
| WO | WO 1993025697 | 12/1993 |
| WO | WO 1994017673 | 8/1994 |
| WO | WO 1996017981 | 6/1996 |
| WO | WO 199701961 | 1/1997 |
| WO | WO 1998012913 | 4/1998 |
| WO | WO 1998053698 | 12/1998 |
| WO | WO 2001022829 | 4/2001 |
| WO | WO 2001022830 | 4/2001 |
| WO | WO 2003070172 | 8/2003 |
| WO | WO 2004113543 | 12/2004 |
| WO | WO 2005013713 | 2/2005 |
| WO | WO 2005019165 | 3/2005 |
| WO | WO 2005046354 | 5/2005 |
| WO | WO 2005097059 | 10/2005 |
| WO | WO 2006041966 | 4/2006 |
| WO | WO 2006042608 | 4/2006 |
| WO | WO 2007060288 | 5/2007 |
| WO | WO 2007115899 | 10/2007 |
| WO | WO 2007137125 | 11/2007 |
| WO | WO 2007137128 | 11/2007 |
| WO | WO 2007118751 | 12/2007 |
| WO | WO 2008017499 | 2/2008 |
| WO | WO 2008030089 | 3/2008 |
| WO | WO 2008083117 | 7/2008 |
| WO | WO 2009007424 | 1/2009 |
| WO | WO 2009060678 | 5/2009 |
| WO | WO 2010101625 | 9/2010 |
| WO | WO 2012075088 | 6/2012 |
| WO | WO 2012106751 | 8/2012 |
| WO | WO 2012110797 | 8/2012 |
| WO | WO 2012116703 | 9/2012 |
| WO | WO 2010110493 | 10/2012 |
| WO | WO 2012157544 | 11/2012 |
| WO | WO 2013010037 | 1/2013 |
| WO | WO 2013010042 | 1/2013 |
| WO | WO 2013013292 | 1/2013 |
| WO | WO 2013138793 | 9/2013 |
| WO | WO 2014110532 | 7/2014 |
| WO | WO 2014110540 | 7/2014 |
| WO | WO 2015127388 | 8/2015 |

OTHER PUBLICATIONS

Al-Karadaghi et al., "Crystal structure of ferrochelatase: the terminal enzyme in heme biosynthesis," Structure, Nov. 15, 1997, 5(11):1501-1510.

(56) References Cited

OTHER PUBLICATIONS

Basman et al., "Effects of transglutaminase on SDS-PAGE patterns of wheat, soy, and barley proteins and their blends," Journal of Food Science, Sep. 2002, 67(7):2654-2658.
Bengoechea et al., "Rheology and microstructure of gluten and soya-based o/w emulsions," Rheologica Acta, Oct. 2006, 46(1):13-21.
Berk, "Technology of production of edible flours and protein products from soybeans," FAO Agric. Serv. Bull., 1992, 97: 16 pages.
Bourtoom, "Edible films and coatings: characteristics and properties," International food research journal, Feb. 2008, 15(3):237-248.
Boye et al., "Comparison of the functional properties of pea, chickpea and lentil protein concentrates processed using ultrafiltration and isoelectric precipitation techniques," Food Research International, Mar. 1, 2010, 43(2):537-546.
Dary et al., "Iron compounds for food fortification: guidelines for Latin America and the Caribbean 2002," Nutrition Reviews, Jul. 1, 2002, 60(7):S50-S61.
Day et al., "Wheat-gluten uses and industry needs," Trends in food science & technology, Feb. 1, 2006, 17(2):82-90.
Fdc.gov [online], "Beef, loin, top loin steak, boneless, lip-on, separable lean only, trimmed to 1/8" fat, choice, raw", Dec. 16, 2019, retrieved on May 2, 2022, retrieved from URL<https://fdc.nal.usda.gov/fdc-app.html#/food-details/746759/nutrients>, 5 pages.
Fdc.gov [online], "Beef, round, top round roast, boneless, separable lean only, trimmed to 0" fat, select, raw", Dec. 16, 2019, retrieved on May 2, 2022, retrieved from URL<https://fdc.nal.usda.gov/fdc-app.html#/food-details/746761/nutrients>, 5 pages.
Flückiger-Isler et al., "Dietary components of malt extract such as maltodextrins, proteins and inorganic salts have distinct effects on glucose uptake and glycogen concentrations in rats," The Journal of nutrition, Sep. 1, 1994, 124(9):1647-1653.
Food processing technology: Principles and practice, 3rd ed., 2009, Chapter 6, 69 pages.
Foster et al., "A randomized trial of a low-carbohydrate diet for obesity," New England Journal of Medicine, May 22, 2003, 348(21):2082-2090.
Frustaci et al., "The *Escherichia coli* visA gene encodes ferrochelatase, the final enzyme of the heme biosynthetic pathway," Journal of bacteriology, Apr. 1993, 175(7):2154-2156.
Gennadios et al., "Edible Coatings and Films," Edible coatings and films to improve food quality, 1994, Chapter 9, 81 pages.
Goto et al., "Iron fortification of rice seed by the soybean ferritin gene," Nature biotechnology, Mar. 1999, 17(3):282-286.
Halton et al., "Low-carbohydrate-diet score and the risk of coronary heart disease in women," New England Journal of Medicine, Nov. 9, 2006, 355(19):1991-2002.
Hendrowarsito, "Melt transformation extrusion of soy protein," Doctoral dissertation, Ohio University, The Faculty of the College of Engineering and Technology, Nov. 1984, 114 pages.
Hoare et al., "Precipitation of food proteins and their recovery by centrifuging and ultrafiltration," Journal of Chemical Technology and Biotechnology, Biotechnology, Sep. 1984, 34(3):199-205.
Hou et al., "Genetic variability of seed sugar content in worldwide soybean germplasm collections," Crop Science, May 2009, 49(3):903-912.
Impossiblefoods.com [online], "Heme, Health, and the Plant-Based Diet," Mar. 2, 2018, retrieved on May 2, 2022, retrieved from URL<https://impossiblefoods.com/blog/heme-health-the-essentials>, 6 pages.
Ingredients in meat products: properties, functionality and applications, Springer Science & Business Media, Feb. 21, 2009, Chapter 7, 145-171.
Iwanaga et al., "Extraction and characterization of oil bodies from soy beans: a natural source of pre-emulsified soybean oil," Journal of agricultural and food chemistry, Oct. 17, 2007, 55(21):8711-8716.

Kang et al., "Comparative study of the quality characteristics of defatted soy flour treated by supercritical carbon dioxide and organic solvent," Journal of Food Science and Technology, Jul. 2017, 54(8):2485-2493.
Keerati-u-rai et al., "Soy Protein Functionality," Comprehensive Biotechnology, 2011, 4(45):543-551.
Klue.com [online], "Beyond Meat vs. Impossible Foods: The very real battle between the biggest 'fake-meat' competitors," Jun. 7, 2021, retrieved on May 2, 2022, retrieved from https://klue.com/blog/beyond-meat-vs-impossible-foods-the-very-real-battle-between-the-biggest-fake-meat-competitors, 7 pages.
Krebs et al., "Efficacy and safety of a high protein, low carbohydrate diet for weight loss in severely obese adolescents," The Journal of pediatrics, Aug. 1, 2010, 157(2):252-258.
Li et al., "Purification and structural characterization of the central hydrophobic domain of oleosin," Journal of Biological Chemistry, Oct. 4, 2002, 277(40):37888-37895.
Lim et al. "Response to consumer demand for reduced-fat foods; multi-functional fat replacers," Japan Journal of Food Engineering, Dec. 15, 2010, 11(4): 147-152.
Motoki et al., "Transglutaminase and its use for food processing," Trends in food science & technology, May 1, 1998, 9(5):204-210.
Olivares et al., "Hemoglobin-fortified biscuits: bioavailability and its effect on iron nutriture in school children," Archivos Latinoamericanos de Nutrición, Jun. 1, 1990, 40(2):209-220, Abstract.
Ortiz-Monasterio et al., "Enhancing the mineral and vitamin content of wheat and maize through plant breeding," Journal of Cereal Science, Nov. 1, 2007, 46(3):293-307.
Paoli et al., "Structure-function relationships in heme-proteins," DNA and cell biology, Apr. 2002, 21(4):271-280.
Processed Meats, 3rd ed., 1996, Chapter 3, 28 pages.
Purslow, "Intramuscular connective tissue and its role in meat quality," Meat science, Jul. 1, 2005, 70(3):435-447.
Randle et al., "Quantifying onion flavor compounds responding to sulfur fertility-sulfur increases levels of alk (en) yl cysteine sulfoxides and biosynthetic intermediates," Journal of the American Society for Horticultural Science, Nov. 1, 1995, 120(6):1075-1081.
Reizenstein, "Cattle haemoglobin—a possible dietary iron supplement," British Journal of Haematology, Nov. 1975, 31(3):265-268.
Renkema et al., "The effect of pH on heat denaturation and gel forming properties of soy proteins," Journal of Biotechnology, May 26, 2000, 79(3):223-230.
Sadler, "Meat alternatives—market developments and health benefits," Trends in Food Science & Technology, May 1, 2004, 15(5):250-260.
Sault et al., "A Review of Developments in Simulated Meats," Quarterly Review of Agricultural Economics, Oct. 1970, 23(4): 16 pages.
Scott et al., "Elevation of oil body integrity and emulsion stability by polyoleosins, multiple oleosin units joined in tandem head-to-tail fusions," Plant biotechnology journal, Oct. 2010, 8(8):912-927.
Sonac, "Harimix Proteins: Color Enhancement of Meat," Jul. 2007, Brochure, 4 pages.
Soyinfocenter.com [online] "History of Meat Alternatives (960 CE to 2014)", Dec. 17, 2017, retrieved on May 3, 2022, retrieved from URL<https://www.soyinfocenter.com/books/179>, 7 pages.
Suman et al., "Myoglobin chemistry and meat color," Annual review of food science and technology, Feb. 28, 2013, 4:79-99.
Tzen et al., "Oleosin isoforms of high and low molecular weights are present in the oil bodies of diverse seed species," Plant physiology, Nov. 1990, 94(3):1282-1289.
Tzen et al., "Surface structure and properties of plant seed oil bodies," The Journal of cell biology, Apr. 15, 1992, 117(2):327-335.
Ueda et al., "Characteristic flavor constituents in water extract of garlic," Agricultural and Biological Chemistiy, Jan. 1, 1990, 54(1):163-169.
USDA.gov [online], "What's Your Beef—Prime, Choice or Select?," Sep. 12, 2019, retrieved on May 3, 2022, retrieved from, URL<https://www.usda.gov/media/blog/2013/01/28/whats-your-beef-prime-choice-or-select>, 17 pages.
Warriss et al., "The influence of slaughter method on the residual blood content of meat," Journal of the Science of Food and Agriculture, Jul. 1978, 29(7):608-610.

(56) References Cited

OTHER PUBLICATIONS

Yang et al., "Roles of components of rice-based fat substitute in gelation," Food research international, Nov. 1, 2007, 40(9):1155-1160.
Bartsch et al., "Isolation and Properties of Two Soluble Henne Proteins in Extracts of the Photoanaerobe Chronnatiunn", The Journal of Biological Chemistry, Mar. 1960, 234(3) 825-831.
Carpenter et al., "Rational Design of Stable Lyophilized Protein Formulations: Some Practical Advice", May 15, 1997, 14(8); 969-975.
Dilworth, "Leghemoglobins", Methods in Enzymology, 1980, 69:812-823.
Krainer, et al., "Optimizing cofactor availability for the production of recombinant heme peroxidase in Pichia pastoris," 2015, 1-9, 14(4), Microbial Cell Factories, Vienna, Austria.
[No Author Listed] Impossible Foods Inc. "GRAS Notification for Soybean Leghemoglobin Protein Derived from Pichia Pastoris." GRAS notice 000737, Retrieved from internet <<URL:https://www.fda.gov/downloads/Food/IngredientsPackagingLabeling/GRAS/NoticeInventory/default.htmf>, 1063 pages (Oct. 2, 2017).
Abou El-Ella, "Hard cheese substitute from soy milk," J. Food Sci. 45(6):1777-1778, Jan. 1980.
Acidified Milk Products and Protein Stabilization,Herbstreith & Fox, retrieved on Mar. 3, 2014, http://www.herbstreith-fox.de/en/informative-literature/informative-literature-from-rd-and-tech-application.html, 15 pages.
Alemán et al., "Oxidative stability of a heme iron-fortified bakery product: Effectiveness of ascorbyl palmitate and co-spray-drying of heme iron with calcium caseinate," Food Chemistry, 2016, 196:567-576.
Ames et al., "Volatile Components of a Yeast Extract Composition," J Food Sci 50, pp. 125-131, 1985.
Ames, "Volatile Sulfur Compounds in Yeast Extracts," Chapter 12, Sulfur compounds in foods. Washington DC: ACS, pp. 147-159, 1994.
Analysis of soy hydrolysate, Avomen Analytical Services Laboratory Test Results, Jul. 25, 2019.
Anderson et al., "A new hemoglobin gene from soybean: A role for hemoglobin in all plants," Proc. Natl. Acad. Sci. USA, 93, 5682-5687, 1996.
Asgar et al., "Nonmeat Protein Alternatives as Meat Extenders and Meat Analogs," Comprehensive Reviews in Food Science and Food Safety, 2010, 9:513-529.
Aubrey, "Food For Thought: Saving the Planet, One Burger at a Time: This Juicy Patty Is Meat-Free," The Salt, Feb. 11, 2017, retrieved on Feb. 14, 2017, retrieved from <http://www.npr.org/sections/thesalt/2017/02/11/514544431/saving-the-planet-one-burger-at-a-time-this-juicy-patty-is-meat-free>, 14 pages.
Australian Patent Examination Report No. 1 in Australian Application No. 2012281064, dated Jan. 25, 2016, 5 pages.
Australian Patent Examination Report No. 1 in Australian Application No. 2012281069, dated Sep. 25, 2015, 5 pages.
Baek et al., "Aroma Extract Dilution Analysis of a Beeflike Process Flavor from Extruded Enzyme-Hydrolyzed Soybean Protein," J. Agric. Food Chem., 49, 790-793, 2001.
Baek, "Process Flavors," Handbook of Meat, Poultry and Seafood Quality, Second Edition, 2012, Chapter 7, 91-104.
Baohua, "Animal products processing,", China agricultural science and technology press, 2008, pp. 224-222, English Translation.
Bastide et al., "Heme iron from meat and risk of colorectal cancer: a meta-analysis and a review of the mechanisms involved.," Cancer Prev Res; 4(2); 177-84, 2011.
Bastide et al., "Heme Iron from Meat and Risk of Coloretctal Cancer: A Meta-analysis and a Review of the Mechanisms Involved," Cancer Prevention Research, 2011, vol. 4, pp. 177-184.
Battaglia et al., "The Enigmatic LEA Proteins and Other HydroPhilins1 [W]," Plant Physiology, Sep. 2008, 148:6-24.
Becana et al., "Recent insights into antioxidant defenses of legume root nodules," New Phytologist, 2010, 188:960-976.

Belitz et al., "Aroma Compounds," Food Chemistry, Springer 2009, pp. 340-402.
Belitz et al., Food Chemistry, 3rd revised edition, Springer-Verlag, Berlin (2006), p. 368.
Berrios, et al., "Carbohydrate composition of raw and extruded pulse flours," Food Research International, 2010, 43:531-536.
Beuchat et al., "Fermentation of Peanut Milk with Lactobacillus bulgaricus and L. acidophilus," J. Food Sci. 1978, 43:1109-1112.
Beyond Better Order page and Nutritional Facts, retrieved on Feb. 6, 2014, http://www.beyond-better.com/order.html, 8 pages.
Beyond Meat, posted on or before Feb. 24, 2001, accessed Jan. 7, 2014, http://beyondmeat.com/, 2 pages.
Biede, et al., "Swiss cheese flavor: I, chemical analysis," Journal of Dairy Science, 1979, 62:227-237.
Boca Bruschetta Tomato Basil Parmesan Veggie Patties Package Ingredients, posted on or before Jul. 22, 2008, accessed on Jan. 7, 2014, http://www.bocaburger.com/products/nutrition-info.aspx?product=5928360103, 1 page.
Boca Flame Grilled Meatless Burgers Package Ingredients, posted on or before Jul. 14, 2008, accessed on Jan. 7, 2014, http://www.bocaburger.com/products/nutrition-info.aspx?product=5928367321, 1 page.
Boca Original Meatless Chik'n Nuggets Package Ingredients, posted on or beforeJul. 22, 2008, accessed Jan. 7, 2014, http://www.bocaburger.com/products/nutrition-info.aspx?product=5928360012, 1 page.
Boca Original Vegan Meatless Burgers Package Ingredients, posted on or before Jul. 14, 2008, accessed Jan. 7, 2014, http://www.bocaburger.com/products/nutrition-info.aspx?product=5928333445, 1 page.
Bodnar, "Novel approaches to improving qualities of maize endosperm," Graduate Theses and Dissertations. Paper 10271. Ames, Iowa, USA: Iowa State University Digital Repository @ Iowa State University, 2011, 147 pages.
Boral and Bohidar, "Effect of Ionic Strength on Surface-Selective Patch Binding-Induced Phase Separation and Coacervation in Similarly Charged Gelatin-Agar Molecular Systems," Journal of Physical Chemistry B, 2010, 114(37): 12027-35.
Bradshaw, "Food 2.0: the future of what we eat," FT Magazine, Oct. 31, 2014, retrieved on Nov. 11, 2014, http://www.ft.com/cms/s/2/bfa6fca0-5fbb-11e4-8c27-00144feabdc0.html#axzz3InGaCIdL, 6 pages.
Brewer, "The Chemistry of Beef Flavor," Dec. 2006, retrieved on Aug. 30, 2016, <http://beefresearch.org/CMDocs/BeefResearch/The%20Chemistry%20of%20Beef%20Flavor.pdf>, 16 pages.
Brooks et al., "Prediction of beef flavor by precursor and volatile compounds Principal Investigators: Funded by the Beef Checkoff," Texas Tech University, May 31, 2012, retrieved Aug. 30, 2016, <http://www.beefresearch.org/CMDocs/BeefResearch/PE_Project_Summaries_FY11Prediction_of_beef_flavor.pdf>.
Brown et al., "The structure and function of mammalian and plant globins," International Review of Scientific Synthesis, Sep. 2013, 2014, 21 pages.
Bunge et al., "Quest Heats up for Alternatives to Beef," The Wall Street Journal, Business News, Nov. 4, 2016, p. B5.
Burdock, "Fenaroli's handbook of flavor ingredients," CRC press, 17 pages (2016).
Bute Island Foods, "Sheese," posted on or before Dec. 5, 2006, retrieved on Feb. 6, 2014, http://www.buteisland.com/a_sheese_home.htm, 2 pages.
Butler et al., "A haemoprotein from the lipid of peanuts," Nature, Mar. 1965, pp. 1319-1321.
Buttery et al., "Thiamin Odor and Bis(2-methyl-3-furyl) Disulfide," J. Agri. Food Chem., vol. 32, No. 3, pp. 674-676, 1984.
Buttery, "Flavor Chemistry and Odor Thresholds," In: Teranishi, R, Wick, EL, Hornstein, I, editors. Flavor chemistry: thirty years of progress, pp. 353-365, 1999.
Cadwallader and Macleod, "16 Instrumental methods for analyzing the flavor of muscle foods," Flavor of Meat, Meat Products and Seafoods, 18 pages (1998).
Calkins et al., "A fresh look at meat flavor," Meat Science, 77(1):63-80 (2007).
Carlsen et al., "Heme-iron in lipid oxidation," Coordination Chemistry Review, 2005, 249:485-498.

(56) References Cited

OTHER PUBLICATIONS

Cerny et al., "Formation of Aroma Compounds from Ribose and Cysteine during the Maillard Reaction," J. Agric. Food Chem., 2003, 51, pp. 2714-2721.
Chamlee, "Why Do People Want Veggie Burgers That Bleed?," Eater, Jul. 25, 2016, retrieved Aug. 25, 2016, <http://www.eater.com/2016/7/25/12270698/lab-grown-meat-beyond-burger-impossible-foods>, 11 pages.
Charkin, et al., "Fragmentation of heme and hemin+ with sequential loss of carboxymethyl groups: A DFT and mass-spectrometry study," Chemical Physics Letters, 2005, 415:362-369.
Chau, "Uncanny Patty," The Ringer, Feb. 27, 2017, retrieved on Feb. 28, 2017, retrieved from <https://theringer.com/impossible-burger-last-meal-on-earth-week-food-f9f14acdb99d#.vocb2hi6e>, 19 pages.
Chaudhari et al., "The cell biology of taste," 190(3):285-296 (Aug. 2010).
Chen et al., "Effect of Urea on Volatile Generation from Maillard Reaction of Cysteine and Ribose," J. Agric. Food Chem., 48:3512-3516 (2000).
Chen et al., "Influence of DNA on Volatile Generation from Maillard Reaction of Cysteine and Ribose," Nutraceutical Beverages, American Chemical Society, pp. 427-442 (Dec. 2003).
Chicago Vegan Foods, accessed on Jan. 7, 2014, http://chicagoveganfoods.com/products/teese-vegan-cheese/, 8 pages.
Chohan et al., "Catalytic Effect of Cobalt, Copper, Iron, Magnesium, Manganese, Nickel and Zinc Metal ions on the Conversion of Glucose into 5-Bydroxymethylfurfuraldehyde.," Jour. Chem. Soc. Pak. vol. 19, No. 3, pp. 221-223, 1997.
Christlbauer et al., "Characterization of the Key Aroma Compounds in Beef and Pork Vegetable Gravies á la Chef by Application of the Aroma Extract Dilution Analysis," J. Agric. Food Chem., 2009, 57:9114-9122.
Clare et al., "Effects of Transglutaminase Catalysis on the Functional and Immunoglobulin Binding Properties of Peanut Flour Dispersions Containing Casein," J. Agric. Food Chem., 2008, 56(22):10913-10921.
Collman et al., "Regioselective and Enantioselective Epoxidation Catalyzed by Metalloporphyrins," Science, vol. 261, pp. 1404-1411, 1993.
Connelly and Piper, "Person of the Year: Tal Ronnen," VegNews, Nov./Dec. 2013, 29-32.
Cott et al., "The 'Impossible' Veggie Burger: A Tech Industry Answer to the Big Mac," Business Day, Jan. 13, 2017, retrieved on Jan. 17, 2017, <https://mobile.nytimes.com/2017/01/13/business/veggie-burger-impossible-burger.html?referer=http://www.drudgereport.com/>, 7 pages.
Cross et al., "Developing a heme iron database for meats according to meat type, cooking method and doneness level," Food Nutr Sci., 3(7): 905-913, 2012.
Dai, "David Chang Adds Plant Based 'Impossible Burger' to Nishi Menu," Jul. 26, 2016, retrieved Jul. 27, 2016 <http://ny.eater.com/2016/7/26/12277310/david-chang-impossible-burger-nishi>, 6 pages.
Daiya, Deliciously Dairy Free, "Say Cheese, Dairy-Free cheesy deliciousness," posted on or before Jan. 26, 2010, accessed Jan. 7, 2014, http://www.daiyafoods.com, 6 pages.
Datar, I. et al., "Possibilities for an in vitro meat production system" Innovative Food Science and Emerging Technologies, vol. 11, 13-22, 2010.
Davis et al., "Some Rheological Properties of Aqueous Peanut Flour Dispersions," J. Texture Studies, 2007, 38:253-272.
Declaration of Dr. Jorge Ruiz-Carrascal, dated Jul. 29, 2019, 72 pages.
Deliciously Healthy Nacheez, Products and Nutrition Facts, posted on or before Jan. 23, 2011, retrieved on Feb. 7, 2014, http://nacheez.com/, 9 pages.
Derwent, "Cheese-like, soybean-fermented foodstuff prodn.—by inoculating soybean milk with lactic acid bacteria and protein decomposing yeast," 1979.
Dharmadhikari, "Yeast Autolysis," Vineyard and Vintage View, retrieved on Nov. 27, 2020, retrieved from URL <https://www.extension.iastate.edu/wine/yeast-autolysis>,6 pages.
Dinh et al., "Effects of USDA quality grade and cooking on water-soluble precursors of beef flavor," Meat Science, 2018, 146:122-130.
Dixie Diner's Club, Cheese (Not!) Sauce Nutrition Facts, posted on or before Sep. 3, 2009, retrieved on Feb. 7, 2014, http://www.dixiediner.com/cheese-notÂ™-sauce-regular-cheese-p-69.html, 2 pages.
D'Onfro, "I tried the plant-based meat that Google wanted to buy and I never want to eat a 'real' hamburger again" Business Insider, Jun. 12, 2016, retrieved Jun. 14, 2016, <http://www.businessinsider.com/impossible-burgers-taste-test-2016-6>, 14 pages.
Donnelly, "Meet the Impossible Burger: It Looks and Tastes Like the Real Thing But Is Totally Meat-Free," Vogue, Aug. 1, 2016, retrieved Aug. 25, 2016 <http://www.vogue.com/13462891/impossible-burger-meat-free-vegan-david-chang/>, 6 pages.
Door 86 Vegan Cheese, Discover a New World of Vegan Cheese and Menu, posted on or before Dec. 5, 2013, retrieved Feb. 7, 2014, http://door86vegancheese.wix.com/door-86-vegan-cheese#, 14 pages.
Dr. Cow, Natural Living & Organic Foods, "Aged Cashew & Brazil Nut Cheese," posted on or before Sep. 22, 2008, accessed Feb. 7, 2014, http://www.dr-cow.com/products/aged-cashew-brazil.html, 1 page.
Dr. Cow, Natural Living & Organic Foods, "Aged Cashew & Crystal Algae Cheese," posted on or before Sep. 22, 2008, accessed Feb. 7, 2014, http://www.dr-cow.com/products/aged-cashew-crystal.html, 1 page.
Dr. Cow, Natural Living & Organic Foods, "Aged Cashew & Dulse Cheese," posted on or before Sep. 22, 2008, accessed Feb. 7, 2014, http://www.dr-cow.com/products/aged-cashew-dulse.html, 1 page.
Dr. Cow, Natural Living & Organic Foods, "Aged Cashew & Hemp Seeds Cheese," posted on or before Sep. 22, 2008, accessed Feb. 7, 2014, http://www.dr-cow.com/products/aged-cashew-hemp.html, 1 page.
Dr. Cow, Natural Living & Organic Foods, "Aged Cashew Nut Cheese," posted on or before Sep. 22, 2008, accessed Feb. 7, 2014, http://www.dr-cow.com/products/aged-cashew-nut-cheese.html, 1 page.
Dr. Cow, Natural Living & Organic Foods, "Aged Macadamia & Hemp Seeds Cheese," posted on or before Sep. 22, 2008, accessed Feb. 7, 2014, http://www.dr-cow.com/products/aged-macadam-hemp.html, 1 page.
Dr. Cow, Natural Living & Organic Foods, "Aged Macadamia Nut Cheese," posted on or before Sep. 22, 2008, accessed Feb. 7, 2014, http://www.dr-cow.com/products/aged-macadam-nut-cheese.html, 1 page.
Dr. Cow, Natural Living & Organic Foods, "Cashew Nut Cream Cheese," posted on or before Sep. 22, 2008, accessed Jan. 7, 2014, http://www.dr-cow.com/products/cashew-nut-cream-cheese.html, 1 page.
Duane, "Engineering the Future of Artisanal Vegan Cheese," Food & Wine, Nov. 2013, http://www.foodandwine.com/articles/engineering-the-future-of-artisanal-vegan-cheese, 5 pages.
Duff et al., "Hemoglobin expression in germinating barley.," Seed Science Research, 431-436, 1998.
DuFosse et al., "Importance of lactones in food flavours," Sciences Des Aliments, 14:17-25 (1994).
Dwivedi, Basant K. et al., "Meat flavor" Critical Reviews in Food Science & Nutrition, vol. 5, 487-535, 1975.
Edris et al., "Application of headspace-solid-phase micro extraction and HPLC for the analysis of the aroma volatile components of treacle and determination of its content of 5-hydroxymethylfurfural (HMF)," Food Chemistry vol. 104, Issue 3, pp. 1310-1314, 2007.
Elise, "Classic Meatloaf Recipe," Simply Recipes, 2009, https://www.simplyrecipes.com/recipes/classic meatloaf/, downloaded Nov. 22, 2017, 11 pages.
Ellfolk, Nils, "Crystalline Leghemoglobin" ACTA Chemical Scandinavica, vol. 15, 545-554, 1961.
Ellis et al., "Structure of ferric soybean leghemoglobin a nicotinate at 2.3 A resolution," Acta Crystallographica, May 1997, Section D, 53(3):302-310.

(56) References Cited

OTHER PUBLICATIONS

Elmore et al., "Effect of the Polyunsaturated Fatty Acid Composition of Beef Muscle on the Profile of Aroma Volatiles," J. Agric. Food Chem. 47:1619-1625 (1999).
Elzerman et al., Exploring meat substitutes: consumer 2013 experiences and contextual factors: British Food Journal, vol. 115 Issue: 5, pp. 700-710, 705, 2013.
EP Opposition "Letter from Opponent" in EP Appln. No. 14737766.7 dated Aug. 6, 2019, 55 pages.
EP Opposition "Response to Summons," in Appln. No. 14737766.7, dated, Nov. 19, 2020, 9 pages.
EP Opposition "Third-Party Observation," in Appln. No. 14737766.7, dated, Jan. 18, 2021, 5 pages.
EP Opposition, "Supplemental responsive declaration of Dr. Jorge Ruiz-Carrascal," Exhibit D103 in European Appln. No. 1737766.7, dated Nov. 11, 2020, 7 pages.
EP Opposition, in Application No. 14737766.7, dated Jul. 4, 2019, 8 pages.
EPO Opposition, "Proprietor's observations and amendments under Rule 79(1) EPC," Feb. 27, 2019, 50 pages.
Erickson et al., "Lipid Oxidation of Muscle Foods," Chapter 12, Food Lipids Chemistry, Nutrition, and Biotechnology Second Edition,48 pages, 2002.
Estevez, et al., "Analysis of volatiles in meat from Iberian pigs and lean pigs after refrigeration and cooking by using SPME-GC-MS," Journal of Agricultural and Food Chemistry, 2003, 51:3429-3435.
Etienne, "Eating the plant-derived Impossible Burger cooked by Momofuku's David Chang," Tech Crunch, Jul. 26, 2016, retrieved Aug. 25, 2016, <https://techcrunch.com/2016/07/26/eating-the-plant-derived-impossible-burger-cooked-by-momofukus-david-chang/>, 9 pages.
European Search Report (Supplementary) in European Application No. 12810661.4, dated Mar. 12, 2015, 14 pages.
European Search Report (Supplementary) in European Application No. 12811683.7, dated Mar. 12, 2015, 9 pages.
European Search Report for International Application No. EP 14737766, dated Jul. 15, 2016, 11 pages.
European Search Report for International Application No. EP 17210528, dated May 14, 2018, 10 pages.
Evers et al., "Furans Substituted at the Three Position with Sulfur," American Chemical Society: Washington, pp. 184-119, 1976.
Everse, "Heme Proteins.," In Encyclopedia of Biological Chemistry, Elsevier Inc., vol. 2, pp. 354-361, 2004.
Extended European Search Report for International Application No. EP 21161324.5, dated Sep. 22, 2021, 12 pages.
Extended European Search Report in Application No. 18203176.5, dated May 31, 2019.
Fang et al., "Food Nutrition health theory and technology," China light industry press, p. 448, Jan. 31, 1997 (English Translation).
Fantastic World Foods, "Fantastic Foods Nature's Burger (Meatless Burger Mix)," posted on or before Jan. 6, 2009, accessed on Jan. 7, 2014, http://fantasticfoods.elsstore.com/view/product/?id=8715&cid=1967, 2 pages.
Farmer et al., "Interaction of Lipid in the Maillard Reaction between Cysteine and Ribose: the Effect of a Triglyceride and Three Phospholipids on the Volatile Products," J Sci Food Agric., 53, 505-525, 1990.
FDA Statement and Response, GRAS Notice 540, dated May 29, 2015, 13 pages.
FDA Statement, "Structural comparison of plant hemoglobins and animal myoglobins," annex to communication in opposition to EP Patent No. 2943072, 2019, 5 pages.
Felt, "Raw Vegan Almond Ricotta Cheese," FeedYourSkull, Mar. 12, 2012, https://feedyourskull.com/2012/03/12/raw-vegan-almond-ricotta-cheese/, 15 pages.
Fengyi et al., "Soybean protein production and application,", China light industry press, 2004, pp. 275-277, English Translation.
Field et al., "Heme Pigment Content of Bovine Hemopoietic Marrow and Muscle," J. Food Sci., 45:1109-1112, 1980.
Follow Your Heart Homepage, posted on or before Nov. 28, 1999, accessed Jan. 7, 2014, http://www.followyourheart.com, 3 pages.
Follow Your Heart, Products and Nutrition Facts, posted on or before Nov. 28, 1999, accessed Feb. 7, 2014, http://www.followyourheart.com/products/, 26 pages.
Foo, "Beef and Scallop Stir-Fry," Food & Wine, Jul. 2001, retrieved on Sep. 10, 2015, http://www.foodandwine.com/recipes/beef-and-scallop-stir-fry/print, 3 pages.
Food for Lovers, Vegan Queso Original & Vegan Queso Mild, posted on or before Oct. 27, 2011, retrieved Feb. 7, 2014, http://www.foodforlovers.com/products, 3 pages.
Fountoulakis and Lahm, "Hydrolysis and amino acid composition analysis of proteins," J. Chromatogr A, 826: 109-134, 1998.
Fourth Chinese Office Action in Chinese Application No. 201280041713.1, dated Nov. 11, 2016, 18 pages (with translation).
Free & Easy Dairy Free Cheese Flavour Sauce Mix, Holland & Barrett, posted on or before Jun. 22, 2013, retrieved Feb. 7, 2014, http://www.hollandandbarrett.com/pages/product_detail.asp?pid=2686, 2 pages.
Fridman et al., "Isolation and Characterization of Soybean Cytochrome c," Archives of biochemistry and biophysics, Feb. 1968, 126:299-304.
Friedman and Brandon, "Nutritional and health benefits of soy proteins," J. Agric. Food Chem., 2001, 49(3): 1069-1086.
Fromson, "The Race to Build a Fake-Meat Burger That Just Might Save the World, Free the cows!" New York Magazine, Jun. 1-7, 2015, 46-48.
Fyrestam and Ostman, "Determination of heme in microorganisms using HPLC-MS/MS and cobalt(III) protoporphyirin IX inhibition of heme acquisition in *Escherichia coli*," Anal. Bioanal. Chem., 2017, 409:6999-7010.
Galaxy Foods Vegan Soy Grated Parmesan, ShopRite, retrieved Feb. 7, 2014, http://www.shoprite.com/pd/Galaxy-Nutritional-Foods/Vegan-Grated-Soy-Topping-Parmesan-Flavor/4-oz/077172640006/, 6 pages.
Gardein the Ultimate Beefless Burger Package Ingredients, posted on or before 2013, accessed Jan. 7, 2014, http://gardein.com/products/beefless-burger/, 12 pages.
Gardenburger the Original Veggie Burger Package Ingredients, posted on or before Oct. 5, 2008, accessed Jan. 7, 2014, http://www.gardenburger.com/product.aspx?id=11630, 1 page.
Gasser et al., "Identification of volatile flavour compounds with high aroma values from cooked beef," Z Lebensm Unlcrs Forsch, 186: 489-494, 1988.
Gasser et al., "Primary odorants of chicken broth," Z Lebensm Unters Forsch, 190: 3-8, 1990.
GenBank Accession No. AAA02168.1, May 21, 1993, 1 page.
GenBank Accession No. AFB70892.1, Sariam, "Non-symbiotic hemoglobin [*Vigna radiata*]," dated Feb. 26, 2012, 1 page.
GenBank Accession No. AFK42304.1, unknown [Medicago truncatula], May 25, 2012, 1 page.
Gharst, "Biochemical and Rheological Characteristics of Peanut Proteins Cross-linked with Microbial Transglutaminase," A dissertation submitted to the Graduate Faculty of North Carolina State University, Raleigh NC, 2007, 149 pages.
Gharst, "Effects of Transglutaminase Catalysis on the Functional and Immunoglobulin Binding Properties of Peanut Flour Dispersions Containing Casein," J. Agric. Food Chem., 2008, 56:10913-10921.
Gharst, "The Effect of Transglutaminase Crosslinking on the Rheological Characteristics of Heated Peanut Flour Dispersions," J. Food Sci., 2007, 72(7):C369-C375.
Gilbert et al., "The revolutionary meatless burger from Impossible Foods is perfect for vegetarians and carnivores alike," Tech Insider, Aug. 4, 2016, retrieved on Aug. 25, 2016, <http://www.techinsider.io/the-impossible-foods-burger-review-vegetarian-2016-8>, 9 pages.
Gledhill, "The detection of iron protoporphyrin (heme b) in phytoplankton and marine particulate material by electrospray ionisation mass spectrometry—comparison with diode array detection," Anal. Chim. Acta., 2014, 841:33-43.
Go Veggie!, "O% Dairy. 100% Yum.," posted on or before 2013, accessed Jan. 7, 2014, http://goveggiefoods.com/our-products/dairy-free-cheese-alternative-products/, 1 page.

(56) References Cited

OTHER PUBLICATIONS

Go Veggie!, Dairy Free Products and Nutrition Facts, posted on or before 2013, accessed Feb. 7, 2014, http://goveggiefoods.com/our-products/dairy-free-cheese-alternative-products/, 13 pages.
Gordinier, "Masters of Disguise Among Meatless Burgers," The New York Times, Mar. 22, 2011, accessed Jan. 7, 2014, http://www.nytimes.com/2011/03/23/dining/23meatless.html?pagewanted=all&_r=0, 5 pages.
Griffths, "XCIII. The Action of Gastic Juice on Beef Muscle-Globulin, With References to Anaemia," Biochemistry Journal, 28:671-675 (1934).
Grigorakis et al., "Organoleptic and volatile aroma compounds comparison of wild and cultured gilthead sea bream (*Sparus aurata*): sensory differences and possible chemical basis," Aquaculture 225:109-119 (2003).
Grobart, "Making a Steak Without a Cow," Bloomberg Technology, Jun. 21, 2016, retrieved Jun. 23, 2016 <http://www.bloomberg.com/news/articles/2016-06-21/making-a-steak-without-the-cow>, 2 pages.
Grosch, "Evaluation of the Key Odorants of Food by Dilution Experiments, Aroma Models and Omission," Chem. Senses 26:533-545 (Jun. 2001).
Grounds for Opposition Against European Patent No. EP 2 943 072, dated Sep. 27, 2018, 44 pages.
Groves et al., "Asymmetric Hydroxylation, Epoxidation, and Sulfoxidation Catalyzed by Vaulted Binaphthyl Metalloporphyrins," J. Org. Chem., 55, 3628-3634, 1990.
Grunwald et al., "Mechanisms of Heme Protein-Mediated Lipid Oxidation Using Hemoglobin and Myoglobin Variants in Raw and Heated Washed Muscle," J. Agric. Food Chem., 2006, 54:8271-8280.
Güntert et al., "Identification and Formation of Some Selected Sulfur-Containing Flavor Compounds in Various Meat Model Systems," J. Agri. Food Chem., 38, 2027-2041, 1990.
Gupta et al., "Plant hemoglobins: Important players at the crossroads between oxygen and nitric oxide.," FEBS Letters, pp. 3843-3849, 2011.
Haandel et al., "Characterization of Different Commercial Soybean Peroxidase Preparations and Use of the Enzyme for N-Demethylation of Methyl N-Methylanthranilate to Produce the Food Flavor Methylanthranilate," J. Agric. Food Chem, 2000, 48: 1949-1954.
Hanlon, "Fake Meat: is science fiction on the verge of becoming fact?," The Guardian, Jun. 22, 2012, http://www.theguardian.com/science/2012/jun/22/fake-meat-scientific-breakthroughs-research, 7 pages.
Hannah, "A fermented feast," Bittersweet, retrieved on Nov. 3, 2016, retrieved from <https://bittersweetblog.com/2010/06/09/a-fermented-feast/>, 2 pages.
Happycow.net, [online], "For Love of Sea Vegetables," dated Jul. 10, 2019, Internet URL: https://www.happycow.net/blog/for-love-of-sea-vegetables/, 5 pages.
Hardison, R., "Hemoglobin's from bacteria to man: Evolution of different patems of gene expression.," The Journal of Experimental Biology, 1099-1117, 1998.
Hargrove et al., Characterization of Recombinant Soybean Leghemoglobin and Apolar Distal Histidine Mutants, Journal of molecular biology, 1032-42, 1997.
Heller, "Barbecued Soybeans," Vegetarian Soybean Recipes, Mother Earth News, Jan./Feb. 1985, http://motherearthnews.com/real-food/vegetarian-soybean-recipes-zmaz85asie.aspx.
Heme Protein Database, "Welcome to the Heme Protein Database," posted on or before Apr. 14, 2013, accessed Dec. 18, 2013, http://hemeprotein.info/heme.php, 1 page.
Heritage Health Food Creamy Veeta Cheese Sauce Mix, Vegan Essentials, posted on or before Aug. 13, 2013, retrieved Feb. 7, 2014, http://store.veganessentials.com/creamy-veeta-cheeze-sauce-mix-by-heritage-health-food-p3945,aspx, 1 page.
Herper, "Mission Impossible Burger: Tasting the Fake Meat That Wants to Save the World," Forbes, Jul. 28, 2016, retrieved on Aug. 25, 2016, <http://www.forbes.com/sites/matthewherper/2016/07/28/mission-impossible-burger-tasting-the-fake-meat-that-wants-to-save-the-world/#57781d823c43>, 6 pages.
Herper, "Drop that Burger," Forbes Online, Nov. 12, 2009, http://www.forbes.com/forbes/2009/1130/thought-leaders-mcdonalds-global-warming-drop-that-burger.html, 4 pages.
Heterologous, Merriam-Webster Dictionary, retrieved on Sep. 10, 2015, http://www.merriam-webster.com/dictionary/heterologous, 1 page.
Hofmann et al., "Evaluation of the Key Odorants in a Thermally Treated Solution of Ribose and Cysteine by Aroma Extract Dilution Techniques," J. Agri. Food Chem., 43, 2187-2194, 1995.
Hofmann et al., "Lactic Fermentation of Ground Soybean for Use in Imitation Cream Cheese Products," J. Food Sci., 50(2):325-329, 1985.
Hofmann et al., "Studies on the Formation and Stability of the Roast-Flavor Compound 2-Acetyl-2-thiazoline," J. Agri. Food Chem., 43, 2946-2950, 1995.
Homma et al. "Cheese-like food production from various nuts," Food Preservation Science, Japan 2009, Abstract.
Hoshaw, "Silicon Valley's Bloody Plant Burger Smells, Tastes and Sizzles Like Meat" the salt, Jun. 21, 2016, retrieved Jun. 21, 2016 <http://www.npr.org/sections/thesalt/2016/06/21/482322571/silicon-valley-s-bloody-plant-burger-smells-tastes-and-sizzles-like-meat>, 8 pages.
Hui et al., "Handbook of meat and meat processing," CRC Press, 2012, retrieved on Dec. 5, 2016, retrieved from <https://www.crcpress.com/Handbook-of-Meat-and-Meat-Processing-Second-Edition/Hui/p/book/9781439836835>, 3 pages.
Ibrahim, et al., "Mechanism of the CO-sensing heme protein CooA: new insights from the truncated heme domain and UVRR spectroscopy," Journal of Inorganic Biochemistry, 2007, 101:1776-1785.
Ice Cream and Ice Cream Desserts, Herbstreith & Fox, retrieved on Mar. 3, 2014, http://www.herbstreith-fox.de/en/informative-literature/informative-literature-from-rd-and-tech-application.html, 5 pages.
Impossible Foods Response to Opponent's Reply in opposition to EP Patent No. 2943072, dated Nov. 21, 2019, 28 pages.
Innovation at Its Best: 5 Years of Food Valley Awards, Food Valley, retrieved on Mar. 7, 2014, http://www.foodvalley.nl/English/Afbeeldingen/FVAjubileumuitgave/Innovation%20at%20Its%20Best%20-%205%20Years%20of%20Food%20Valley%20Awards.pdf, 51 pages.
International Preliminary Report on Patentability in International Application No. PCT/US2012/046560, dated Jan. 23, 2014, 12 pages.
International Preliminary Report on Patentability in International Application No. PCT/US2012/46552, dated Jan. 23, 2014, 9 pages.
International Preliminary Report on Patentability in International Application No. PCT/US14/11347, dated Jul. 14, 2015, 10 pages.
International Preliminary Report on Patentability in International Application No. PCT/US14/11362, dated Jul. 23, 2015, 10 pages.
International Preliminary Report on Patentability in International Application No. PCT/US2014/011361, dated Jul. 14, 2015, 13 pages.
International Search Report and Written Opinion in International Application No. PCT/US2012/046560, dated Dec. 14, 2012, 11 pages.
International Search Report and Written Opinion in International Application No. PCT/US2012/46552, dated Nov. 19, 2012, 12 pages.
International Search Report and Written Opinion in International Application No. PCT/US14/11347, dated Jul. 3, 2014, 20 pages.
International Search Report and Written Opinion in International Application No. PCT/US14/11361, dated Jun. 16, 2014, 26 pages.
International Search Report and Written Opinion in International Application No. PCT/US14/11362, dated Jun. 13, 2014, 19 pages.
International Search Report and Written Opinion in International Application No. PCT/US2015/017147, dated May 1, 2015, 15 pages.
International Search Report and Written Opinion in International Application No. PCT/US2015/023679, dated Aug. 28, 2015, 26 pages.
Invitation to Pay Fees in International Application No. PCT/US14/11361, dated Apr. 10, 2014, 4 pages.

(56) References Cited

OTHER PUBLICATIONS

Jahreis, et al., "Legume flours: nutritionally important sources of portein and dietary fiber," Ernahrungs Umschau, 2016, 63(2):36-42.
Jamieson, "Iroquois Stew with Beef, Chicken and Pork," Epicurious, Nov. 1995, retrieved on Sep. 10, 2015, http://www.epicurious.com/recipes/food/printerfriendly/iroquois-stew-with-beef-chicken-and-pork-865, 2 pages.
Jenschke, et al., "Unsaturated fatty acids and sodium affect the liver-like off-flavor in cooked beef," J. Anim. Sci., 2007, 85:3072-3078.
Jensen, "Comparative Analysis of Autoxidation of Hemoglobin," J. Experimental Biology, 2001, 204:2029-2033.
Jianjun Jiang, et al., "Food technology (vol. 1)," Higher Education Press, 2002, 1:31-32, English translation.
Jin et al., "Aroma Properties of Some Oxazoles," Perfumer & Flavorist, vol. 9, August/September, 4 pages, 1984.
Ju and Kilara, "Textural Properties of Cold-set Gels Induced from Heat-denatured Whey Protein Isolates," J. Food Science, 1998, 63(2): 288-292.
Jublot et al., "Quantitation of sulphur aroma compounds in maillard model reaction systems of different composition," Expression of Multidisciplinary Flavour Science, 4 pages (2010).
Kanani, "The Future of Meat is Meatless, Just as Tasty, and About to Change the World," Forbes, Mar. 6, 2014, retrieved on Sep. 11, 2015, http://www.forbes.com/sites/rahimkanani/2014/03/06/the-future-of-meat-is-meatless-just-as-tasty-and-about-to-change-the-world/, 8 pages.
Karahadian et al., "Action of Tocopherol-Type Compounds in Directing Reactions Forming Flavor Compounds in Autoxidizing Fish Oils," J. Amer. Oil Chem. Soc., 66:1302-8 (1989).
Kendrick and Watts, "Acceleration of inhibition of lipid oxidation by heme compounds," Lipids, 1969, 4:454-458.
Kerler et al., "Basic chemistry and process conditions for reaction flavours with particular focus on Maillard-type reactions," Food Flavor Tech., 2010, 3:3.2-3.3.
Kerscher and Grosch, "Quantification of 2-Methyl-3-furnathiol, 2-Furfurylthiol, 3-Mercapto-2-pentanone in Heated Meat," J. Agric. Food Chem. 46:1954-1958 (1996).
Kerth and Miller, "Beef flavor: a review from chemistry to consumer," White Paper: Product Quality, Texas A&M University Dept of Animal Sciences, 25 pages (2013).
Khan et al., "Meat flavor precursors and factors influencing flavor precursors—A systematic review," Meat Science, 110:278-284 (Dec. 2010).
Kohler, et al., "Physiological Characterization of a Heme-Deficient Mutant of *Staphylococcus aureus* by a Proteomic Approach," Journal of Bacteriology 2003, 185:6928-6937.
Kolodyaznaya, "Pishchevaya khimiya [Food chemistry]," St. Petersburg, SPBGAKHPT Publ. 1999, Translation, 7 pages.
Konermann et al., "Acid-induced denaturation of myoglobin studied by time resolved electrospray ionization mass spectrometry", Biochemistry, 1997, vol. 36, pp. 6448-6454.
Koutsidis et al., "Water-soluble precursors of beef flavor: I. Effect of diet and breed," Meat Science, 79:124-130, 2008.
Kraft American Singles Package Ingredients, posted on or before Jun. 27, 2012, accessed on Jan. 7, 2014, http://www.kraftrecipes.com/Products/ProductInfoDisplay.aspx?SiteId=1&Product=2100060473, 1 page.
Kummer, "The Problem with Fake Meat," MIT Technology Review, Mar. 31, 2015, retrieved Apr. 20, 2016, <https://www.technologyreview.com/s/536296/the-problem-with-fake-meat/>, 11 pages.
Kung et al., "Tobacco as a Potential Food Source and Smoke Material: Nutritional Evaluation of Tobacco Leaf Protein," J. Food Sci., 1980, 45(2):320-322, 327.
Lane and Nursten, "The Variety of Odors Produced in Maillard Model Systems and How They Are Influenced by Reaction Conditions," in: The Maillard Reaction in Foods and Nutrition, Waller and Feather, eds., ACS Symposium Series, 1983, No. 215, pp. 141-158.
Lane et al., "The Variety of Odors Produced in Maillard Model Systems and How They are Influenced by Reaction Conditions," The Maillard Reaction in Foods and Nutrition, American Chemical Society, pp. 141-158 (Apr. 1983).
Leahy Gardens Vegan & Delicious, Macaroni & Cheese and Cheese Flavored Sauce Mix Product and Nutrition Facts, posted on or before Feb. 8, 2010, retrieved Feb. 7, 2014, http://www.leaheyfoods.com/products/MacCheese.aspx, 3 pages.
Leduc et al., "Differentiation of fresh and frozen/thawed fish, European sea bass (*Dicentrarchus labrax*), gilthead seabream (*Spams aurata*), cod (*Gadus morhua*) and salmon (*Salmo salar*), using volatile compounds by SPME/GC/MS," J. Sci. Food Agric., 92:2560-80 (2012).
Lee et al., "Cloning and Expression Analysis of 2-on-2 Hemoglobin from Soybean.," Journal of Plant Biology, 47(2), 92-98, 2004.
Leghemoglobin, NCBI's database accession 004939, Mar. 1, 2002.
Lendl, "Untersuchung des Rsstzwiebelaromas," Z. Lebensm. Unters.-Forsch. 157, 229-234, 1975.
Lira-Ruan et al., "Expression of non-symbiotic hemoglobin 1 and 2 genes in rice (*Oryza sativa*) embiyonic organs.," Communicative and Integrative Biology, 4(4), 457-458, 2011.
Lisanatti Foods, Vegan Cheese Products and Nutrition Facts, posted on or before Mar. 26, 2013, retrieved Feb. 7, 2014, http://www.lisanatti.com/index.php?option=com_zoo&view=category&layout=category&Itemid=22, 5 pages.
Lisitsin et al., "Analogues of meat products with functional properties", All about meat, 2007, Translation, 8 pages.
Liu et al., "Intermolecular Interactions During Complex Coacervation of Pea Protein Isolate and Gum Arabic," Journal of Agricultural and Food Chemistry, 2010, 58:552-556.
Liu, "Comparison of lipid content and fatty acid composition and their districtuion within seeds of 5 small grain species," J. Food Sco., 2011, 76(2):C334-C342.
Lombardi et al., "Total Heme and Non-heme Iron in Raw and Cooked Meats," Journal of Food Science, 67(5):1738-1741 (2002).
Lopez, "We just tried the 'Impossible Burger'—the meatless burger NYC has been waiting for," Business Insider, Jul. 27, 2016, retrieved on Aug. 25, 2016, <http://www.businessinsider.com/what-the-impossible-burger-tastes-like-2016-7>, 5 pages.
Low Methylester Amidated Pectins, Herbstreith & Fox, retrieved on Mar. 3, 2014, http://www.herbstreith-fox.de/en/informative-literature/informative-literature-from-rd-and-tech-application.html, 13 pages.
Lu et al., "Catalytic C—H functionalization by metalloporphyrins: recent developments and future directions," Chem. Soc. Rev., 40, 1899-1909, 2011.
Lugay and Kim, "Freeze alignment: A novel method for protein texturization," Utilization of Protein Resources, 1981, p. 177-187.
Luteness, "The Richest Source of Protein," MOSAIC, May/Jun. 1979, 39-45.
MacLeod, "The Scientific and Technological Basis of Meat Flavours," 12, 36 pages, 1986.
Macleod, Glesni et al., "Natural and simulated meat flavors (with particular reference to beef)" Critical Reviews in Food Science & Nutrition, vol. 14, 309-437, 1981.
MacMunn "An address on some of the applications of the spectroscope to medicine", The British Medical Journal, Jan. 3, 1989, pp. 3-9.
Macnicol, "Developmental changes in the free amino acid pool and total protein amino acids of pea cotyledons (*Pisum sativum* L.)," Plant Physiol., 1983, 72:492-497.
Mahajan, et al., "Aroma compounds in sweet whey powder," Journal of dairy science, 2004, 87:4057-4063.
Maltais et al., "Formation of Soy Protein Isolate Cold-Set Gels: Proteins and Salt Effects," J. Food Science, 2005, 70 (1): C67-C73.
Maqsood et al., "Haemoglobinmediated lipid oxidation in the fish muscle: A review," Trends in Food Science & Technology, 2012, 28:33-43.
Marshall et al., "We Tried the "Bleeding" Vegetarian Burger and It Was Actually Good," Jul. 27, 2016, retrieved Jul. 28, 2016 <https://www.buzzfeed.com/chelseamarshall/bleeding-vegetable-burger?utm_term=.jaa03Kyo7#.ogV0m7MAW>, 10 pages.
Martins et al., "Meat flavor generation in complex maillard model systems," American Chem. Soc., 2010, 71-83.
McGorrin, "Advances in Dairy Flavor Chemistry," FoodFlavors and Chemistry: Advances of the New Millennium, Spanier, A. M.;

(56) References Cited

OTHER PUBLICATIONS

Shahidi,F.; Parliment, T. H.; Mussinan, C. J.; Ho, C.-T.; Contis, E. T., Eds., Royal Society of Chemistry, Cambridge, pp. 67-84 (2001).
McGorrin, "Character-impact flavor and off-flavor compounds in foods," Flavor, Fragrance, and Odor Analysis, 2nd, 207-262 (2012).
McGorrin, "The significance of volatile sulfur compounds in food flavors," Volatile sulfur compounds in food 1068, 29 pages (2011).
Meisinger, et al., Flavor relationships among muscles from the beef chuck and round, Journal of Animal Science, 2006, 84:2826-2833.
Mercola.com [online], "Controversy over fake meat burger heats up as documents reveal FDA safety concerns," Aug. 21, 2017, retrieved on Jan. 2, 2018, retrieved from URL <https://articles.mercola.com/sites/articles/archive/2017/08/21/impossible-burger-meat-substitute.aspx>, 9 pages.
Meunier et al., "Metal-oxo species in P450 enzymes and biomimetic models. Oxo-hydroxo tautomerism with water-soluble metalloporphyrins," Topics in Catalysis vol. 21, Nos. 1-3, pp. 47-54, 2002.
Mintel, [Online], "Greek Style Cultured Almond Milk Yogurt," retrieved from www.gnpd.com, Nov. 2012 Database accession No. 1943001, 5 pages.
Moon et al., "Odour-active components of simulated beef flavour analyzed by solid phase micro extraction and gas chromatography-mass spectrometry and -olfactometry," Food Research International, 39:294-308 (Apr. 2006).
Morita, "Comparison of aroma characteristics of 16 fish species by sensory evaluation and gas chromatographic analysis," J. Sci. Food Agric., 83:289-297 (2003).
Morningstar Farms Garden Veggie Patties Package Ingredients, posted on or before Jun. 26, 2013, accessed Jan. 7, 2014, https://www.morningstarfarms.com/products/burgers/garden-veggie-patties, 6 pages.
Mottram et al., "Formation of Sulfur Aroma Compounds in Reaction Mixtures Containing Cysteine and Three Different Forms of Ribose," J. Agric. Food Chem., 50:4080-4086 (2002).
Mottram, "Flavor Compounds Formed during the Maillard Reaction," Chapter 10, 23 pages, 1993.
Mottram, "Flavour formation in meat and meat products: a review," Food Chemistry, 62(4):415-24 (Aug. 1998).
Mottram, "An Overview of the Contribution of Sulfur-Containing Compounds to the Aroma in Heated Foods," Heteroatomic Aroma Compounds, American Chemical Society, pp. 73-92 (Aug. 2002).
Mouritsen et al., "Seaweeds for umami flavour in the New Nordic Cuisine," Flavour 1:4, 12 pages, 2012.
Nacho Mom's Vegan Queso, Products and Nutrition Facts, posted on or before Sep. 20, 2010, retrieved on Feb. 7, 2014, http://fatgoblin.com/Home.html, 6 pages.
Naike, "Food Flavor Chemistry," 1st Edition China Light Industry Press, pp. 236-243 (1996) (English Translation).
Nielsen et al., "Improved Method for Determining Food Protein Degree of Hydrolysis," Journal of Food Science: Food Chemistry and Toxicology, vol. 66, 2001.
Nielson, Introduction to the Chemical Analysis of Foods, Jones & Bartlett Publishers, 1994.
Nutty Cow Nut Cheeses, Products and Nutrition Facts, posted on or before Jul. 23, 2012, retrieved Feb. 7, 2014, http://www.nuttycow.com/, 6 pages.
Oellingrath, "Heat Degradation of Heme in Methemoglobin and Metmyoglobin Model Systems Measured by Reversed-Phase Ion-Pair High Performance Liquid Chromatography," J Food Science, 1998, 53(1): 40-42.
Ofori and Hsieh, "The Use of Blood and Derived Products as Food Additives," Chapter 13 of book Food Additive Edited by Yehia El-Samragy Published: Feb. 22, 2012.
Oldach, "Biochemistry of a Burger: Impossible Foods does science, makes food and tries to change the world," ASBMB Today, retrieved from URL <https://www.asbmb.org/asbmb-today/industry/100119/biochemistry-of-a-burger>, Oct. 1, 2019, 12 pages.
Opponent's Reply Letter in opposition to EP Patent. No. 2943072, dated Jan. 20, 2020, 18 pages.
Opponent's Reply Letter in opposition to EP Patent. No. 2943072, dated Nov. 21, 2019, 15 pages.
Oshodi et al., "In vitro protein digestibility, amino acid profile and available iron of infant-weaning food prepared from maize flour and bovine blood," Food Research International, vol. 30, No. 3-4, pp. 193-197, 1997.
Pacificharvest.com, [online], "Red Seaweeds—Nutritional Benefits & Quick Applications," dated Jul. 14, 2016, Retrieved from Internet on Jul. 26, 2019, Internet URL: https://www.pacificharvest.co.nz/blog/general-information/red-seaweeds, 11 pages.
PancakeNinja, "Beef and chicken cheese burgers"—Pancake Ninja, 2011, http://pancake-ninja.blogspot.com/2011/06/beef-and-chicken-cheese-burgers.html, downloaded Nov. 22, 2017, 8 pages.
Parmela Parmesan Style Aged Nut Cheese, Product and Nutrition Facts, 2012, retrieved Feb. 7, 2014, http://www.parmelafoods.com/your-health.html, 4 pages.
Pashynska, et al., "Characterization of Noncovalent Complexes of Antimalarial Agents of the Artemisinin-Type and FE(III)-Heme by Electrospray Mass Spectrometry and Collisional Activation Tandem Mass Spectrometry," J. Am. Soc. Mass Spectrom., 2004, 15:1181-1190.
Pazos et al., "Effect of pH on Hemoglobin-Catalyzed Lipid Oxidation in Cod Muscle Membranes in Vitro and in Situ," J. Agric. Food Chem., 2005, 53:3605-3612.
Peace Cheese 100% Plant-based Cheese Alternative, Product and Nutrition Facts, posted on or before Jun. 6, 2012, retrieved Feb. 7, 2014, http://www.ilovepeacecheese.com/#/products/4571642621, 3 pages.
Peas, green raw,FoodData Central, US Department of Agriculture, retrieved from URL <https:/fdc.nal.usda.gov/fdc-app.html#/food-details/170419/nutrients>, Apr. 1, 2019, 8 pages.
Peterson, "The Impact of the Enzymatic Hydrolysis Process on Recovery and Use of Proteins", In: Birch G.G., Blakebrough N., Parker K.J. (eds) Enzymes and Food Processing. Springer, Dordrecht (1981).
Pittet et al., "Comparative Study of Flavor Properties of Thiazole Derivatives," J. Agr. Food Chem., vol. 22, No. 2, pp. 264-269, 1974.
Proulx et al., "Iron Bioavailability of Hemoglobin from Soy Root Nodules Using a Caco-2 Cell Culture Model," J. Agricultural and Food Chemistry, Feb. 2006, 54(4): 1518-1522.
Proulx, "Diversified strategies for improving iron bioavailability of maize," Iowa State University—Retrospective Theses and Dissertations, 2007 retrieved on Sep. 19, 2016, retrieved from <http://lib.dr.iastate.edu/rtd/15852/>, 144 pages.
Punk Rawk Labs: an ongoing experiment in optimal health, Nut Milk Cheese Products, posted on or before Jun. 8, 2011, retrieved Feb. 7, 2014, http://www.punkrawklabs.net/cheeses.html, 4 pages.
Ramos et al., "What is Masa?—Ingredient Intelligence," The Kitchen, retrieved on Dec. 1, 2016, http://www.thekitchn.com/whats-the-difference-between-masa-and-masa-harina-226434, 5 pages.
Rebellato et al., "Iron in fortified biscuits: A simple method for its quantification, bio accessibility study and physicochemical quality," Food Research International, 2015, 77:385-391.
Rebuttal Declaration of Dr. Jorge Ruiz-Carrascal and Supporting Exhibits, dated Jan. 20, 2020, 12 pages.
Reedy et al., "Development of a heme protein structure-electrochemical function database," Nucleic Acids Research, 2008, 36:307-313.
Rethink Meat,Presented at the 6th Annual Sustainable Innovation Forum, Paris, France, Dec. 7-8, 2015, retrieved on Feb. 1, 2016, https://amp.twimg.com/v/7c7f7084-b173-42cb-bc12-723f35994dff, 1 page (Video Submission).
Richards et al., "Effects of Fish Heme Protein Stmcture and Lipid Substrate Composition on Hemoglobin-Mediated Lipid Oxidation," J. Agric. Food Chem., 2007, 55:3643-3654.
Richards et al., "Pro-oxidative Characteristics of Trout Hemoglobin and Myoglobin: A Role for Released Heme in Oxidation of Lipids," J. Agric. Food Chem., 2005, 53:10231-10238.
Richins et al., "Effect of Iron Source on Color and Appearance of Micronutrient-Fortified Com Flour Tortillas," Cereal Chem., 85:561-5 (2008).

(56) References Cited

OTHER PUBLICATIONS

Road's End Organics, Cheese Sauce Mix Products and Nutrition Facts, posted on or before Oct. 28, 2009, retrieved Feb. 7, 2014, http://www.edwardandsons.com/reo.shop.chreese.itml, 6 pages.
Road's End Organics, Mac & Cheese Products and Nutrition Facts, posted on or before Oct. 28, 2009, retrieved Feb. 7, 2014, http://www.edwardandsons.com/reo_shop_pastas.itml, 7 pages.
Rochet and Chaintreau, "Carbonyl Odorants Contributing to the In-Oven Roast Beef Top Note," J. Agric. Food Chem., 53:9578-9585 (Nov. 2005).
Rowe, "Chemistry and technology of flavors and fragrances," Oxford:: Blackwell; 2005, 351 pages.
Rusli, "The Secret of These New Veggie Burgers: Plant Blood," The Wall Street Journal, Oct. 7, 2014, retrieved on Oct. 9, 2014, http://online.wsj.com/articles/the-secret-of-these-new-veggie-burgers-plant-blood-1412725267, 5 pages.
Schieberle et al., "Characterization of Key Odorants in Dry-Heated Cysteine-Carbohydrate Mixtures: Comparison with Aqueous Reaction Systems," Flavor Analysis, American Chemical Society, pp. 320-330 (Sep. 1998).
Schwartz, "Meet the Silicon Valley-Backed Vegan Cheese That You Might Actually Eat," Fast Company, Feb. 26, 2014, retrieved Sep. 11, 2015, http://www.fastcoexist.com/3025648/meet-the-silicon-valley-backed-vegan-cheese-that-you-might-actually-eat, 6 pages.
Segner, "Meatless burger made possible with local effort," Jul. 29, 2016, retrieved Aug. 1, 2016 <http://www.southernminn.com/owatonna_peoples_press/news/article_3d414149-1040-534d-blaf-bf4f8c486788.html>, 5 pages.
Selli et al., "Odour-active and off-odour components in rainbow trout (*Oncorhynchus mykiss*) extracts obtained by microwave assisted distillation-solvent extraction," Food Chemistry, 114:317-322 (2009).
Shahidi et al., "Meat flavor volatiles: A review of the composition, techniques of analysis, and sensory evaluation," CRC Critical Reviews in Food Science and Nutrition, 24(2):141-243 (Jan. 1986).
Shaw et al., "Bioavailability of Iron from Purple Laver (*Porphyra* spp.) Estimated in a Rat Hemoglobin Regeneration Bioassay," J. Agric. Food Chem., 48, pp. 1734-1737, 2000.
Shi et al., "Identification of characteristic flavour precursors from enzymatic hydrolysis-mild thermal oxidation tallow by descriptive sensory analysis and gas chromatography-olfactometry and partial least squares regression," Journal of Chromatography B, 913-914:96-76 (Jan. 2013).
Shimbayashi et al.,"Free Amino Acids and Phsphorylethanolamine in Milk Whey of Cow" Agr. Biol. Chem, 29(1): 13-19, 1965.
Shu et al., "Parameter Effects on the Thermal Reaction of Cystine and 2,5-Dimethyl-4-hydroxy-3(2H)-furanone," Thermal Generation of Aromas, American Chemical Society, pp. 229-241 (Oct. 1989).
Silicon Valley gets a taste for food,The Economist Technology Quarterly, Mar. 7, 2015, http://cdn.static-economist.com/sites/default/files/sponsorships/accenture_tq_march2015/20150307_tq_mailout.pdf, pp. 11-13.
Singh, et al., "Functional and edible uses of soy protein products," Comp. Rev. Food Sci. Food Safety, 2008, 7:14-28.
Sister River Foods Parma!, Products and Nutrition Facts, Posted on or before Jun. 2, 2012, retrieved Feb. 11, 2014, http://www.veganstore.com/product/parma-vegan-parmesan/vegan-cheese-and-dairy-alternatives, 6 pages.
Soller, "The Impossible Burger is Ready for Its (Meatless) Close-Up," The Wall Street Journal, Jun. 14, 2016, retrieved Jun. 21, 2016 <http://www.wsj.com/articles/the-impossible-burger-is-ready-for-its-meatless-close-up-1465912323>, 8 pages.
Song, et al., "Agricultural and sideline products processing value-added technology II: Processing of soybean products," Henan Science and Technology Press, 2009, 1:64-69, English translation.
Song, et al., "Contribution of oxidized tallow to aroma characteristics of beef like process flavour assessed by gas chromatography-mass spectrometry and partial least squares regression," Journal of Chromatography A, 1254:115-124 (Sep. 2012).

Soy Kaas, Products, posted on or before Jan. 20, 2011, retrieved Feb. 11, 2014, http://www.soykaas.com/products, 1 page.
Soyco Cheese Products, Natural Pantry, retrieved Feb. 11, 2014, http://www.natural-pantry.com/search_results.asp?ct=All&site_search_qu=soyco&storeID=D92VLAQVMPDL9L5UHTS2W-LU67NADEHUA, 10 pages.
Soymage Cheese Products, Good Earth Natural Foods, retrieved on Feb. 11, 2014, http://www.goodearthnaturalfoods.com/shop/brand2.asp?storeID=PJ102JRNHNGT8G0QMPEQ7LDC7GX6C2W2&alpha=S&brand=Soymage&brand_id=805, 6 pages.
Specht et al., "Identification of Volatile Flavor Compounds with High Aroma Values from Shallow-Fried Beef," J. Agric. Food Chem., 1994, 42:2246-2253.
Spence et al., "Multisensory Flavor Perception," Cell 161: 24-35 (2015).
Stabilization of Whey and Whey Mix Products with Pectin, Herbstreith & Fox, retrieved on Mar. 3, 2014, http://www.herbstreith-fox.de/en/informative-literature/informative-literature-from-rd-and-tech-application.html, 6 Pages.
Ste Martaen Cheese, Products and Nutrition Facts, posted on or before May 28, 2009, retrieved Feb. 11, 2014, http://stemartaen.bigcartel.com/, 14 pages.
Sterling, "Welcome to the Era of Plant-Based Meat," Food & Wine, Apr. 13, 2016, Retrieved Apr. 20, 2016, <http://www.foodandwine.com/blogs/welcome-era-plant-based-meat>, 3 pages.
Strelec et al., "Aminopeptidases of Germinated and Non-Germinated Barley," Barley Aminopeptidases, Food Technol. Biotechnol. 47 (3), 296-303, 2009.
Supplementary European Search Report for International No. EP 14737909.3, dated Oct. 7, 2016, 10 pages.
Supplementary European Search Report in European Application No. 15774164, dated Oct. 27, 2017, 11 pages.
Supplementary Partial European Search Report in European Application No. 14738061 dated Nov. 7, 2016, 11 pages.
Swanson, "Patenting the Quest for a More Perfect Veggie Burger," JDSUPRA Business Advisor, Jun. 21, 2016, retrieved Jun. 23, 2016 <http://www.jdsupra.com/legalnews/patenting-the-quest-for-a-more-perfect-72212/>. 13 pages.
Swiderski et al., "Spent Brewer's Yeast Autolysates as a New and Valuable Component of Functional Food and Dietary Supplements," J. Food Process Technol, 2015, 6:12, 6 pages.
Tang et al., "Flavor chemistry of 2-methyl-3-furanthiol, an intense meaty aroma compound," Journal of Sulfur Chemistry, 11 pages, (2012).
Texturizing of Fermented Milk Products, Herbstreith & Fox, retrieved on Mar. 3, 2014, http://www.herbstreith-fox.de/en/informative-literature/informative-literature-from-rd-and-tech-application.html, 6 pages.
The Daiya Advantage, Products and Nutrition Facts, posted on or before Jan. 26, 2010, retrieved on Feb. 7, 2014, http://us.daiyafoods.com/our-products, 126 pages.
The Good Scents Company, "The Good Scents Company Information System," 2015, retrieved on Dec. 1, 2016, http://www.thegoodscentscompany.com/, 2 pages.
The Vegetarian Express Parma Zaan Sprinkles, posted on or about Oct. 17, 2009, retrieved Feb. 11, 2014, http://www.thevegetarianexpress.com/cart/home.php?cat=250, 2 pages.
Tofu Rella Mozzarella Cheese, Natural Pantry, retrieved Feb. 11, 2014, http://www.natural-pantry.com/shop/product_view.asp?id=24684&StoreID=D92VLAQVMPDL9L5UHTS2WLU67NADEHUA&private_product=0, 2 pages.
Tofutti Cheese Products and Nutrition, posted on or before Jun. 26, 2013, retrieved Feb. 11, 2014, http://www.tofutti.com/dairy-free-cheeses/, 18 pages.
Tofutti Milk Free, "Premium Dairy Free Cheeses,", posted on or before Jun. 26, 2013, accessed Jan. 7, 2014, http://www.tofutti.com/dairy-free-cheeses/, 2 pages.
Tong et al. ,"Blood Composition of Different Beef Breed Types" Can. J. Anim. Sci, 66:915-924 (Dec. 1986).
Topunov, A.F., et al., "Hemoglobin's: Evolution, Abundance, and Heterogeneity," Uspekhi Biologicheskoi Khimii, vol. 41, 2001, p. 207, partial translation, 1 page.

(56) References Cited

OTHER PUBLICATIONS

Trader Joe's Sliced Soy Cheese Alternative, Fotki, posted Oct. 27, 2008, retrieved Feb. 11, 2014, http://public.fotki.com/harwons/food/tj-sliced-soy-cheese.html, 1 pages.
Trader Joe's Vegan Mozzarella, A(soy) Bean, posted Jun. 7, 2013, retrieved Feb. 11, 2014, http://a-soy-bean.blogspot.com/2013/06/showdown-trader-joes-vegan-mozzarella.html, 13 pages.
Treeline Treenut Cheese, Products and Nutrition Facts, posted on or before Dec. 10, 2013, retrieved on Feb. 11, 2014, http://www.treelinecheese.com/treeline-cheese-products.html, 3 pages.
Tressl et al., "Formation of Amino Acid Specific Maillard Products and Their Contribution to Thermally Generated Aromas," Thermal Generation of Aromas, American Chemical Society, pp. 156-171 (Oct. 1989).
Uauy et al., "Iron Fortification of Foods: Overcoming Technical and Practical Barriers," J. Nutr. 132:849S-852S (2002).
United States Environmental Protection Agency Document EPA-745-B-99-0145, 1999.
Usami, Aya et al., "Heme-mediated binding of a-casein to ferritin: evidence for preferential a-casein binding to ferrous iron" Biometals, vol. 24, 1217-1224, 2011.
Vaghefi, et al., "Influence of the extent of hemoglobin hydrolysis on the digestive absorption of heme iron. An in vitro study," Journal of Agricultural and Food Chemistry, 2002, 50:4969-4973.
Van Ba et al., "Principles of Meat Aroma flavors and Future Prospect," INTECH Open Science, Open Minds, 2012, Chapter 7, 145-176.
Van Den Ouweland et al., "Components Contributing to Beef Flavor. Volatile Compounds Produced by the Reaction of 4-Hydroxy-5-methyl-3(2.ff)-furanone and Its Thio Analog with Hydrogen Sulfide," J. Agri. Food Chem., vol. 23, No. 3, pp. 501-505, 1975.
Van Den Ouweland et al., "Process Meat Flavor Development and the Maillard Reaction," In Thermal Generation of Aromas, ACS Symposium Series, American Chemical Society, 1989, 433-441.
Vasilescu et al., "Chapter 6: Meat Freshness: Peroxynitrite's Oxidative Role, Its Natural Scavengers, and New Measuring Tools," American Chemical Society, Dec. 2014, 30 pages.
VBites, "Cheezly," posted on or before 2013, accessed Jan. 7, 2014, http://www.vbitesfoods.com/meat-free/cheezly.html, 2 pages.
Vegan Sun Artisan Aged Raw Cheese, Vegan Essentials, retrieved Feb. 11, 2014, http://store.veganessentials.com/vegan-sun-artisan-aged-raw-cheese-p4201.aspx, 3 pages.
VegCuisine Soy Cheese Products, The Vegan Store, retrieved on Feb. 11, 2014, http://www.veganstore.com/category/s?keyword=vegcuisine, 5 pages.
Veggie Brothers Mozzarella Sticks, Vegan Essentials, Nov. 9, 2013, retrieved Feb. 11, 2014, http://store.veganessentials.com/vegan-mozzarella-sticks-by-veggie-brothers-p3761.aspx, 2 pages.
Veggie burgers that look, taste, and bleed like real meat,CBS News, Aug. 9, 2016, retrieved Aug. 25, 2016 <http://www.cbsnews.com/news/food-trend-veggie-burgers-that-look-bleed-taste-like-real-meat/>, 4 pages.
Vernin et al., "Mechanisms of Formation of Heterocyclic Compounds in Maillard and Pyrolysis Reactions," Chapter III, Heterocycles in Maillard and Pyrolysis Reactions, pp. 151-217, 1982.
Victoria Vegan Sauces, Products and Nutrition Facts, posted on or about Sep. 16, 2012, retrieved Feb. 11, 2014, http://www.victoriafinefoods.com/products/specialty-sauces/victoria-vegan, 9 pages.
Vitalitymagazine.com,[online], "Sprouts: The Miracle Food," Vitality Magazine, dated Feb. 1, 2005, Retrieved from Internet Jul. 29, 2019, Internet URL: https://vitalitymagazine.com/article/sprouts-the-miracle-food/, 10 pages.
Wajcman et al., "L 'Hemoglobin, from microorganism to man: a single structural motif, multiple functions.," Comptes Rendus Biologies, 325(12), 1159-1174, 2002.
Walter et al, Effect of bovine-hemoglobin-fortified cookies on iron status of schoolchildren: a nationwide program in Child, Am J Clin Nutr, 1993, 57, pp. 190-194.

Wang and Wang, "Principles and techniques of food nutrition and health care," China Light Industry Press, 1998, 1:446-449, English translation.
Wansink, B., "Overcoming the Taste Stigma of Soy" Journal of Food Science: Sensory and Nutritive Qualities of Food, vol. 68, 2604-2606, 2003.
Warendorf, et al., "The flavour of bouillon: 2. Sensory analysis of non-volatiles and imitation of a bouillon," Z. Lebensm. Unters. Forsch., 1992, 195(3):215-223, English Abstract.
Watch Momofuku Cook Impossible Foods' Plant-Based Burger that 'Bleeds', Vice, Jul. 27, 2016, retrieved Aug. 25, 2016, <https://munchies.vice.com/en/videos/watch-momofuku-cook-impossible-foods-plant-based-burger-that-bleeds>, 3 pages.
Wayfare We Can't say It's Cheese Spread, Products and Nutrition Facts, posted on or about Oct. 12, 2013, retrieved Feb. 11, 2014, http://www.wayfarefoods.com/we-cant-say-its-cheese/, 5 pages.
Weenen, "Process Flavourings," Flavourings, pp. 233-258, 1998.
Weinberger et al., "Different regulation of halo peroxidation during agar oligosaccharide-activated defense mechanisms in two related red algae, *Gracilaria* sp. and *Gracilaria chilensis*," Journal of Experimental Botany, vol. 58, No. 15/16, pp. 4365-4372, 2007.
Werkhoff et al., "Isolation and Characterization of Volatile Sulfur-Containing Meat Flavor Components in Model Systems," J. Agri. Food Chem., 38, 777-791, 1990.
Whitfield et al., "Effect of Phospholipid on the Formation of Volatile Heterocyclic Compounds in Heated Aqueous Solutions of Amino Acids and Ribose," 1. Sci. Food Agric., 42, 261-272, 1988.
Wisuthiphaet and Kongruang, "Production of Fish Protein Hydrolysates by Acid and Enzymatic Hydrolysis," J Med Bioeng, 2015, 4(6): 466-470.
Withycombe et al., "Identification of 2-Methyl-3-Furanthiol in the Steam Distillate from Canned Tuna Fish," Journal of Food Science, 53(2):658-660 (1988).
Wood, et al., "Fatty deposition, fatty acid composition and meat quality: a review," Meat Science, 2008, 78:343-358.
Wortham and Miller, "Venture Capitalists Are Making Bigger Bets on Food Start-Ups," The New York Times Online, Apr. 28, 2013, http://www.nytimes.com/2013/04/29/business/venture-capitalists-are-making-bigger-bets-on-food-start-ups.html?pagewanted=all&_r=1&, 4 pages.
Wu et al., "Characterization of the Aroma of a Meat like Process Flavoring from Soybean-Based Enzyme-Hydrolyzed Vegetable Protein," J. Agric. Food Chem., 50, 2900-2907, 2002.
www.jackkruse.com, [online], "Brain Gut 6: Epi-Paleo Rx," dated Jul. 2012, Internet URL: https://jackkruse.com/brain-gut-6-epi-paleo-rx/?print=pdf, 12 pages.
www.maraseaweed.com, [ online], "Smoked Dulse," Applewood Smoked Dulse—Seaweed Flakes | Mara Seaweed, No Date, Retrieved from the Internet Jul. 15, 2019, Internest URL: https://maraseaweed.com/collections/products/products/smoked-dulse, 3 pages.
www.myliquidsupplements.com, "Redseaweed is a rich source of nutrients, essential fatty acids, fiber, protein, complex cards, and minerals and now red sea vegetables are easy to find," Health Benefits of Red Seaweed, dated 2013, Retrieved from Internet Jul. 29, 2019, Internet URL: https//:www.myliquidsupplements.com/red-seaweed/, 10 pages.
www.scotsman.com, [online], "Tom Kitchin: ideas for cooking with seaweed," dated Aug. 5, 2012, Retrieved from Internet Jul. 29, 2019, Internet URL: https://www.scotsman.com/news-2-15012/tom-kitchin-ideas-for-cooking-with-seaweed-1-2451932,12 pages.
www.shop.healthyhealing.com,[online], "What Are Sea Vegetables? (/healthyhealing-safety/what-are-sea-vegetables)," dated Oct. 25, 2012, Retrieved from the Internat Jul. 15, 2019, Internet URL: (https://shop.healthyhealing.com/Seaweed-Products_c_140.html), 5 pages.
www.universal-tao.com, [online], "Sprouts," No Date, Retrieved from Internet on Jul. 29, 2019, Internet URL: https://www.universal-tao.com/article/sprouts/html, 9 pages.
www.wildfoodplants.com, [online], "Teriyaki Weed," dated Sep. 9, 2007, Retrieved from Internet Jul. 15, 2019, Internet URL: https://wildfoodplants.com/2007/09/teriyaki-weed/, 2 pages.

(56) References Cited

OTHER PUBLICATIONS

Xiaoling, "Practical Technology and Quality Management of Deep Processing of Meat Products," China Textile & Apparel Press, pp. 9 and 10 (English Translation), 10 pages.

Yancey et al., "Effects of total iron, myoglobin, hemoglobin, and lipid oxidation of uncooked muscles on livery flavor development and volatiles of cooked beef steaks," Meat Science, 73:680-686 (2006).

Yaylayan et al., "Microwave and Thermally Induced Maillard Reactions," Chapter 38, Thermally Generated Flavors, 8 pages, 1993.

Yeast Metabolom Database, "Heme (YMDB0041)," (http://www.ymdb.ca/compounds/YMDB00041).

Young and Pellett, "Plant proteins in relation to human protein and amino acid nutrition," Am. J. Clin. Nutr., 1994, 59(Suppl):1203S-1212S.

Yves Veggie Cuisine the Good Slice, Shop Well, retrieved on Feb. 11, 2014, http://www.shopwell.com/yves-veggie-cuisine-the-good-slice-cheese-alternative-cheddar-style/soy-foods/p/6082260001, 1 page.

Zampronio et al., "Catalytic oxidation of cyclohexane and cyclooctene over a new metalloporphyrin supported on VOPO4 catalyst," Catalysis Letters vol. 104, Nos. 1-2, 4 pages, 2005.

Zhang et al., "Comparison of the Volatile Compounds Formed from the Thermal Reaction of Glucose with Cysteine and Glutathione," J. Agri. Food Chem., 39, 760-76, 1991.

Zhao et al., "Degradation of RNA during the autolysis of *Saccharomyces cerevisiae* produces predominantly ribonucleotides," J. Ind. Microbiol Biotechnol, Aug. 10, 2005, 32:415-423.

Zhengnong et al., "Cihai biological fascicle," Shanghai Lexicographical Publishing House, p. 243, Dec. 31, 1987 (English Translation).

Flavor compounds affect by the addition of carotenoids in wheat gluten flour upon cooking. Data collected by SPME GCMS.

| Compounds | Peak Area — Lutein Amount |   |   |
|---|---|---|---|
|  | None | Low | High |
| 2,4-Decadienal, (E,E)- | — | ▪ | ■ |
| 2-Pyrrolidinone | — | ■ | — |
| Dimethyl trisulfide | ■ | ▪ | — |
| 2-Acetylthiazole | ■ | ■ | — |
| Carbon disulfide | ■ | — | — |
| Methanethiol | ■ | — | — |
| Pentanoic acid | — | — | ■ |
| Acetic acid | — | — | ■ |
| Butanoic acid | — | — | ■ |
| Propanoic acid | — | — | ■ |
| Ethanone, 1-(2-furanyl)- | ■ | ▪ | — |
| 5-Hepten-2-one, 6-methyl- | ■ | ■ | — |
| 4-Heptenal, (Z)- | ■ | ▪ | — |
| 3-Furaldehyde | ■ | ▪ | — |
| 2-Nonenal, (Z)- | ■ | ▪ | — |
| Phenylacetaldehyde | — | ▪ | ■ |
| 2,4-Nonadienal, (E,E)- | ■ |   |   |
| Acetaldehyde | ■ | ▪ | — |
| Butanal, 3-methyl- | ■ | — | — |
| Propanal, 2-methyl- | ■ | — | — |
| Acetone | ■ | — | — |
| Furfural | ■ | ▪ | — |
| Butanal | ■ | — | — |
| 3-Octen-2-one | ▪ | ■ | — |
| 3,5-Octadien-2-one, (E,E)- | ■ | ▪ | — |
| Phenol | ■ | ▪ | — |
| 1-Penten-3-ol | ■ | ▪ | — |
| Benzyl alcohol | ■ | ▪ | — |
| 2-Penten-1-ol, (Z)- | ■ | — | — |
| 1-Butanol, 3-methyl- | ▪ | ■ | — |
| Butyrolactone | ■ | — | — |
| 2(3H)-Furanone, 5-ethyldihydro- | ■ | — | — |
| 2(5H)-Furanone, 5-ethyl- | ■ | ▪ | — |

GROUND MEAT REPLICAS

CROSS-REFERENCE TO RELATED APPLICATIONS

This application is a continuation of U.S. application Ser. No. 16/238,698 filed on Jan. 3, 2019, which is a continuation of U.S. application Ser. No. 15/300,339 filed on Sep. 29, 2016, which is a U.S. National Application of PCT/US2015/023679 filed Mar. 31, 2015, which claims priority to U.S. Application Ser. No. 61/973,181 filed on Mar. 31, 2014, and to U.S. Application Ser. No. 62/058,230 filed on Oct. 1, 2014, the disclosures of which are incorporated herein by reference in their entirety.

TECHNICAL FIELD

This disclosure relates to meat replicas, such as ground meat replicas, and more particularly to plant-based products that mimic the texture, appearance, and sensory aspects of ground meat, including the texture, appearance, and sensory aspects of cooking and eating ground meat, such as the fibrousness, heterogeneity in texture, beefy flavor, and red-to-brown color transition during cooking of ground meat. This disclosure also relates to compositions and methods for altering the flavor of a food product or a food replica, such as a cheese or meat replica.

BACKGROUND

Meat substitute compositions typically are extruded soy/grain mixtures that fail to replicate the experience of cooking and eating meat. Common limitations of plant-based meat substitute products include a texture and mouth-feel more homogenous than that of equivalent meat products. Furthermore, as these products must largely be sold pre-cooked, with artificial flavors and aromas pre-incorporated, they fail to replicate the aromas, flavors, and other key features, such as texture and mouth-feel, associated with cooking or cooked meat, and they also may have added off flavors. As a result, these products mainly appeal to a limited consumer base that is already committed to vegetarianism, but have failed to appeal to the larger consumer segment accustomed to eating meat. It would be useful to have improved plant-based meat substitutes, which better replicate the fibrousness, texture, aromas and flavors of meat during and/or after cooking.

SUMMARY

This document is based on methods and materials for making plant-based products that can mimic ground meat, including the fibrousness, heterogeneity in texture, beefy or other meat flavor, and red-to-brown color transition during cooking of ground meat, without off flavors. For example, this document provides meat replicas that include proteins that are selected based upon the temperature at which they gel and/or denature to replicate the behavior and qualities of meat during cooking, i.e., the firming, syneresis (water release), chew texture, or mouthfeel. For example, the temperature of denaturing and gelling of the proteins selected to be in the meat replica can be similar to that of proteins typically found in meat (e.g., actin and myosin). Further the plant-based products provided herein can include flavoring agents (e.g., flavorings, flavoring precursors, and/or flavoring compounds) that can provide meaty flavors, such that a plant-based meat replica has a more natural flavor and does not have off flavors. This document therefore also provides methods for making plant-based products containing such flavoring agents.

In one aspect, this document features a meat replica composition that includes about 5% to about 88% (e.g., about 40% to about 88%, about 45% to about 60%, or about 15% to about 55%) by weight of a meat dough; about 0% to about 40% (e.g., about 1% to about 30%, about 5% to about 25%, or about 15% to about 25%) by weight of a carbohydrate-based gel; about 5% to about 35% (e.g., about 10% to about 15%, about 12% to about 18%, or about 20% to about 25%) by weight of a fat; about 0.00001% to about 10% (e.g., about 3% to about 7%, about 0.001% to about 2%, or about 0.00001% to about 2%) by weight of a flavoring agent; about 0% to about 15% (e.g., about 2% to about 15% or about 2% to about 10%) by weight of a binding agent; and about 0.01% to about 4% (e.g., about 0.05% to about 1%, or about 0.5% to about 2%) by weight of a heme-containing protein and/or an iron salt. The meat dough can include a flavoring agent. The fat can include a flavoring agent. The meat dough can be about 45% to about 60% by weight of the composition. The carbohydrate-based gel can be about 10% to about 25% by weight of the composition. The fat can be about 10% to about 15% by weight of the composition. The flavoring agent can be about 3% to about 7% or about 0.001% to about 2% by weight of the composition. The flavoring agent can include one or more flavor precursors, a flavoring, or a flavoring compound. The flavoring agent can be a combination of a flavoring and one or more flavor precursors. The binding agent can be about 2% to about 10% by weight of the composition. The binding agent can include one or more proteins that have been chemically or enzymatically modified to improve their textural and/or flavor properties, or to modify their denaturation and gelling temperatures. The heme-containing protein can be about 0.01% to about 2% by weight of the composition. The composition can include the heme-containing protein and the iron salt. The meat dough can include an isolated plant protein, an edible fibrous component, an optional flavoring agent, and an optional fat. The binding agent can be a conglycinin protein.

In another aspect, this document features a meat replica composition that includes about 5% to about 80% (e.g., about 20% to about 30%) by weight of a meat dough; about 5% to about 35% (e.g., about 15% to about 25%) by weight of a fat; about 15% to about 40% (e.g., about 15% to about 25%) by weight of an edible fibrous component; about 0.1% to about 18% (e.g., about 7% to about 18%) by weight of a carbohydrate-based gel; about 0% to about 10% (e.g., about 0% to about 10%) by weight of a flavoring agent; about 0.5% to about 15% (e.g., about 5% to about 15%) by weight of a binding agent; and about 0.1% to about 8% (e.g., about 2% to about 8%) by weight of a heme-containing protein and/or an iron salt.

In another aspect, this document features a method of making a ground meat replica. The method can include (a) heating a dough to a temperature ranging from 150° F. to 250° F., the dough comprising an isolated plant protein, an optional edible fibrous component, one or more optional flavoring agents, and an optional fat; (b) combining the dough, after heating, with a fat, the fat optionally containing a flavoring agent and/or an isolated plant protein; and (c) combining the dough from step (b) with a carbohydrate-based gel, an optional edible fibrous component, an optional binding agent, a highly conjugated heterocyclic ring complexed to an iron ion and/or an iron salt, and one or more optional flavoring agents to make the ground meat replica.

The method can further include breaking the dough from step (b) into pieces before combining with the carbohydrate-based gel, the optional edible fibrous component, the optional binding agent, the highly conjugated heterocyclic ring complexed to an iron ion and/or the iron salt, and one or more optional flavoring agents.

In another aspect, this document features a method of flavoring a meat dough. The method can include (a) combining a first highly conjugated heterocyclic ring complexed to an iron ion and/or a first iron salt with one or more flavor precursors and an optional fat; (b) heating the mixture to form one or more flavor compounds; and (c) making a dough comprising an isolated plant protein, an optional edible fibrous component, and the mixture from step (b). The method can further include (d) combining the dough, after heating, with a fat, the fat optionally containing a flavoring agent and/or an isolated plant protein; and (e) combining the dough of step (d) with a carbohydrate-based gel, an optional binding agent, a second highly conjugated heterocyclic ring complexed to an iron ion and/or a second iron salt, and one or more optional flavoring agents to make a ground meat replica. The method can further include breaking the dough from step (d) into pieces before combining with the carbohydrate-based gel, the optional binding agent, the second highly conjugated heterocyclic ring complexed to an iron ion and/or the second iron salt, and one or more optional flavoring agents.

In another aspect, this document features a method of flavoring a meat dough, where the method includes (a) making a dough comprising an isolated plant protein, an optional edible fibrous component, one or more optional flavoring agents, and an optional fat; (b) making a flavored fat by combining a fat with a highly conjugated heterocyclic ring complexed to an iron ion and/or a first iron salt, and one or more flavor precursors and heating the mixture; and (c) combining the dough, after heating, with the flavored fat. The method can further include combining the dough of step (c) with a carbohydrate-based gel, an optional binding agent, a second highly conjugated heterocyclic ring complexed to an iron ion and/or a second iron salt, and one or more optional flavoring agents to make a ground meat replica. The method can further include breaking the dough of step (c) before combining with the carbohydrate-based gel, the optional binding agent, the second highly conjugated heterocyclic ring complexed to an iron ion and/or the second iron salt, and one or more optional flavoring agents.

This document also features a method of making a ground meat replica, where the method includes (a) combining an iron salt with one or more flavor precursors and an optional fat; (b) heating the mixture to form one or more flavor compounds; (c) making a dough comprising an isolated plant protein, an optional edible fibrous component, and the mixture from step (b); (d) combining the dough, after heating, with a fat, the fat optionally containing a flavoring agent and/or an isolated plant protein; and (e) combining the dough of step (d) with a carbohydrate-based gel, an optional binding agent, an iron salt, an optional highly conjugated heterocyclic ring complexed to an iron ion, and one or more optional flavoring agents to make the ground meat replica. The method can further include breaking the dough from step (d) into pieces before combining with the carbohydrate-based gel, the optional binding agent, the iron salt, the optional highly conjugated heterocyclic ring complexed to an iron ion, and one or more optional flavoring agents. In some embodiments, a highly conjugated heterocyclic ring complexed to an iron ion can be combined with the iron salt, the one or more flavor precursors, and the fat before heating the mixture.

In yet another aspect, this document features a method of making a ground meat replica. The method can include (a) making a dough comprising an isolated plant protein, an optional edible fibrous component, one or more optional flavoring agents, and an optional fat; (b) making a flavored fat by combining a fat with an iron salt and one or more flavor precursors and heating the mixture; (c) combining the dough, after heating, with the flavored fat; and (d) combining the dough of step (c) with a carbohydrate-based gel, an optional binding agent, an iron salt, an optional highly conjugated heterocyclic ring complexed to an iron ion, and one or more optional flavoring agents to make the ground meat replica. The method can further include breaking the dough from step (c) before combining with the carbohydrate-based gel, the optional binding agent, the iron salt, the optional highly conjugated heterocyclic ring complexed to an iron ion, and one or more optional flavoring agents. In some embodiments, a highly conjugated heterocyclic ring complexed to an iron ion can be combined with the fat, the iron salt, and the one or more flavor precursors before heating the mixture.

In any of the methods or compositions described herein, the iron salt can be iron gluconate, iron chloride, iron oxalate, iron nitrate, iron citrate, iron ascorbate, ferrous sulfate, ferric pyrophosphate, or any other aqueous soluble salt.

In any of the methods or compositions described herein, the heme-containing protein can be a non-animal heme-containing protein, such as a plant-derived heme-containing protein (e.g., leghemoglobin). Further, in some embodiments, the heme-containing protein can be isolated or isolated and purified.

In any of the methods or compositions described herein, wherein the one or more flavor precursors can be a sugar, a sugar alcohol, a sugar acid, a sugar derivative, an oil, a free fatty acid, an amino acid or derivative thereof, a nucleoside, a nucleotide, a vitamin, an acid, a peptide, a phospholipid, a protein hydrolysate, a yeast extract, or a mixture thereof. For example, the flavor precursor can be selected from the group consisting of glucose, fructose, ribose, arabinose, glucose-6-phosphate, fructose 6-phosphate, fructose 1,6-diphosphate, inositol, maltose, sucrose, maltodextrin, glycogen, nucleotide-bound sugars, molasses, a phospholipid, a lecithin, inosine, inosine monophosphate (IMP), guanosine monophosphate (GMP), pyrazine, adenosine monophosphate (AMP), lactic acid, succinic acid, glycolic acid, thiamine, creatine, pyrophosphate, vegetable oil, algal oil, sunflower oil, corn oil, soybean oil, palm fruit oil, palm kernel oil, safflower oil, flaxseed oil, rice bran oil, cottonseed oil, olive oil, sunflower oil, canola oil, flaxseed oil, coconut oil, mango oil, a free fatty acid, cysteine, methionine, isoleucine, leucine, lysine, phenylalanine, threonine, tryptophan, valine, arginine, histidine, alanine, asparagine, aspartate, glutamate, glutamine, glycine, proline, serine, tyrosine, glutathione, an amino acid derivative, urea, pantothenic acid, ornithine, niacin, glycerol, citrulline, taurine, biotin, borage oil, fungal oil, blackcurrant oil, betaine, beta carotene, B-vitamins, N-Acetyl L-cysteine, iron glutamate and a peptone, or mixtures thereof.

In any of the methods or compositions described herein, the isolated plant protein in the dough can include wheat gluten, a dehydrin protein, an albumin, a globulin, or a zein, or mixtures thereof.

In any of the methods or compositions described herein, the optional edible fibrous component can include plant fibers from carrot, bamboo, pea, broccoli, potato, sweet potato, corn, whole grains, alfalfa, kale, celery, celery root, parsley, cabbage, zucchini, green beans, kidney beans, black beans, red beans, white beans, beets, cauliflower, nuts, apple skins, oats, wheat, or psyllium, or a mixture thereof.

In any of the methods or compositions described herein, the edible fibrous component can include an extruded mixture of isolated plant proteins. The extruded mixture can contain wheat gluten and soy protein isolate, and optionally can further contain a flavoring agent (e.g., a flavoring such as yeast extract, a protein hydrolysate, or an oil; a flavor compound; or a flavor precursor). In some embodiments, the edible fibrous component can be a solution-spun protein fiber (e.g., a solution-spun protein fiber containing a prolamin such as corn zein, pea prolamin, kafirin, secalin, hordein, avenin, or a mixture thereof).

In any of the methods or compositions described herein, the fat can be a non-animal fat, an animal fat, or a mixture of non-animal and animal fat. The fat can be an algal oil, a fungal oil, corn oil, olive oil, soy oil, peanut oil, walnut oil, almond oil, sesame oil, cottonseed oil, rapeseed oil, canola oil, safflower oil, sunflower oil, flax seed oil, palm oil, palm kernel oil, coconut oil, babassu oil, shea butter, mango butter, cocoa butter, wheat germ oil, borage oil, black currant oil, sea-buckhorn oil, macadamia oil, saw palmetto oil, conjugated linoleic oil, arachidonic acid enriched oil, docosahexaenoic acid (DHA) enriched oil, eicosapentaenoic acid (EPA) enriched oil, palm stearic acid, sea-buckhorn berry oil, macadamia oil, saw palmetto oil, or rice bran oil; or margarine or other hydrogenated fats. In some embodiments, for example, the fat is algal oil. The fat can contain the flavoring agent and/or the isolated plant protein (e.g., a conglycinin protein).

In any of the methods or compositions described herein, the dough can include the flavoring agent. In any of the methods or compositions, the non-animal fat in the dough can include a flavoring agent. The flavoring agent can be selected from the group consisting of a vegetable extract, a fruit extract, an acid, an antioxidant, a carotenoid, a lactone, and combinations thereof. The antioxidant can be epigallocatechin gallate. The carotenoid can be lutein, β-carotene, zeaxanthin, trans-β-apo-8'-carotenal, lycopene, or canthaxanthin. The vegetable extract can be from a cucumber or a tomato. The fruit extract can be from a melon or pineapple.

In any of the methods or compositions described herein, the carbohydrate based gel can have a melting temperature between about 45° C. and about 85° C. The carbohydrate-based gel can include agar, pectin, carrageenan, konjac, alginate, chemically-modified agarose, or mixtures thereof.

In any of the methods or compositions described herein, the ground meat replica can contain the binding agent. The binding agent can be an isolated plant protein (e.g., a RuBisCO, an albumin, a gluten, a conglycinin, or mixtures thereof). The denaturation temperature of the binding agent can be between about 40° C. and about 80° C. The binding agent can be a carbohydrate based gel that becomes firm upon cooking to 140° F. to 190° F. The carbohydrate based gel can contain methylcellulose, hydroxypropylmethyl cellulose, guar gum, locust bean gum, xanthan gum, or a mixture thereof. The binding agent can be egg albumin or collagen.

In any of the methods or compositions described herein, the highly conjugated heterocyclic ring complexed to an iron ion can be a heme moiety, or a porphyrin, porphyrinogen, corrin, corrinoid, chlorin, bacteriochlorophyll, corphin, chlorophyllin, bacteriochlorin, or isobacteriochlorin moiety complexed to an iron ion. The heme moiety can be a heme-containing protein (e.g., a non-symbiotic hemoglobin, a Hell's gate globin I, a flavohemoprotein, a leghemoglobin, a heme-dependent peroxidase, a cytochrome c peroxidase, or a mammalian myoglobin). In some embodiments, the heme-containing protein can be a leghemoglobin. The leghemoglobin can be from soybean, pea, or cowpea.

In another aspect, this document features a method of increasing the meat flavor or masking off flavors from plant material in a food product. The method can include adding, to the food product, one or more lactones at a concentration of $10^{-3}$ to $10^{-11}$ of the food product, wherein the lactones are selected from the group consisting of tetrahydro-6-methyl-2H-pyran-2-one, delta-octalactone, 5-ethyldihydro-2(3H)-furanone, butyrolactone, dihydro-5-pentyl-2(3H)-furanone, dihydro-3-methylene-2,5-furandione, 1-pentoyl lactone, tetrahydro-2H-pyran-2-one, 6-heptyltetrahydro-2H-pyran-2-one, γ-octalactone, 5-hydroxymethyldihydrofuran-2-one, 5-ethyl-2(5H)-furanone, 5-acetyldihydro-2(3H)-furanone, trans-3-methyl-4-octanolide 2(5H)-furanone, dimethylethyl)-2,5-urandione, 3,4-dihydroxy-5-methyl-dihydrofuran-2-one, 5-ethyl-4-hydroxy-2-methyl-3(2H)-furanone, δ-tetradecalactone, and dihydro-4-hydroxy-2(3H)-furanone. In some embodiments, the lactones can be 5-ethyl-4-hydroxy-2-methyl-3(2H)-furanone, butyrolactone, γ-octalactone, and δ-tetradecalactone. The food product can be a meat replica. The meat replica can be free of animal products.

This document also features a method of increasing the meat flavor or masking off flavors from plant material in a food product, where the method includes adding, to the food product, one or more carotenoids at a concentration of between 0.00001% and 0.1% of the food product, wherein the carotenoids are selected from the group consisting of β-carotene, zeaxanthin, lutein, trans-β-apo-8'-carotenal, lycopene, canthaxanthin, and combinations thereof. The food product can be a meat replica. The meat replica can be free of animal products.

In another embodiment, this document features a method of increasing the meat flavor of a meat replica. The method can include adding, to the meat replica, a vegetable juice, a vegetable puree, a vegetable extract, a fruit juice, a fruit puree, or a fruit extract to the meat replica at a concentration from 0.0001% to 10% of the meat replica. The vegetable juice, vegetable puree, vegetable extract, a fruit juice, a fruit puree, or a fruit extract can be a *Cucumis* juice, puree, or extract (e.g., a juice, puree, or extract from a cucumber or a melon). The method vegetable juice, vegetable puree, vegetable extract, fruit juice, fruit puree, or fruit extract can be cooked or otherwise treated to denature proteins before adding to the meat replica. The meat replica can be free of animal products.

In another aspect, this document features a food product or food replica product containing a heme-containing protein and one or more lactones at a concentration of $10^{-3}$ to $10^{-11}$ of the food product, wherein the one or more lactones are selected from the group consisting of tetrahydro-6-methyl-2H-pyran-2-one, delta-octalactone, 5-ethyldihydro-2(3H)-furanone, butyrolactone, dihydro-5-pentyl-2(3H)-furanone, dihydro-3-methylene-2,5-furandione, 1-pentoyl lactone, tetrahydro-2H-pyran-2-one, 6-heptyltetrahydro-2H-pyran-2-one, γ-octalactone, 5-hydroxymethyldihydrofuran-2-one, 5-ethyl-2(5H)-furanone, 5-acetyldihydro-2(3H)-furanone, trans-3-methyl-4-octanolide 2(5H)-furanone, 3-(1,1-dimethylethyl)-2,5-urandione, 3,4-dihydroxy-5-methyl-dihydrofuran-2-one, 5-ethyl-4-hydroxy-2-methyl-3(2H)-furanone, δ-tetradecalactone, and dihydro-4-hydroxy-2

(3H)-furanone. For example, the one or more lactones can be 5-ethyl-4-hydroxy-2-methyl-3(2H)-furanone, butyrolactone, γ-octalactone, and δ-tetradecalactone. The food product or food replica product can be a meat replica. The meat replica can be free of animal products.

This document also features a food product or food replica product containing a heme-containing protein and one or more carotenoids at a concentration of between 0.00001% and 0.1% of the food product, wherein the one or more carotenoids are selected from the group consisting of β-carotene, zeaxanthin, lutein, trans-β-apo-8'-carotenal, lycopene, canthaxanthin, and combinations thereof. The food product or food replica product can be a meat replica. The meat replica can be free of animal products.

In another aspect, this document features a food product or food replica product containing (a) a heme-containing protein, and (b) a vegetable juice, a vegetable puree, a vegetable extract, a fruit juice, a fruit puree, or a fruit extract at a concentration from 0.0001% to 10% of the food product. The vegetable juice, vegetable puree, vegetable extract, a fruit juice, a fruit puree, or a fruit extract can be a *Cucumis* juice, puree, or extract. The *Cucumis* juice, puree, or extract can be from a cucumber or a melon. The vegetable juice, vegetable puree, vegetable extract, fruit juice, fruit puree, or fruit extract can have been cooked or otherwise treated to denature proteins before being added to the food replica product. For example, the vegetable juice, vegetable puree, vegetable extract, fruit juice, fruit puree, or fruit extract can have been heated to a temperature of about 60° C. to about 100° C. before being added to the food replica product. The food product can be free of animal products.

In another aspect, this document features a food replica product containing one or more lactones at a concentration of $10^{-3}$ to $10^{-11}$ of the food product, wherein the one or more lactones are selected from the group consisting of tetrahydro-6-methyl-2H-pyran-2-one, delta-octalactone, 5-ethyl-dihydro-2(3H)-furanone, butyrolactone, dihydro-5-pentyl-2 (3H)-furanone, dihydro-3-methylene-2,5-furandione, 1-pentoyl lactone, tetrahydro-2H-pyran-2-one, 6-heptyltetrahydro-2H-pyran-2-one, γ-octalactone, 5-hydroxymethyl-dihydrofuran-2-one, 5-ethyl-2(5H)-furanone, 5-acetyldihydro-2(3H)-furanone, trans-3-methyl-4-octanolide 2(5H)-furanone, 3-(1,1-dimethylethyl)-2,5-urandione, 3,4-dihydroxy-5-methyl-dihydrofuran-2-one, 5-ethyl-4-hydroxy-2-methyl-3(2H)-furanone, δ-tetradecalactone, and dihydro-4-hydroxy-2(3H)-furanone. The one or more lactones can be 5-ethyl-4-hydroxy-2-methyl-3(2H)-furanone, butyrolactone, γ-octalactone, and δ-tetradecalactone.

In still another aspect, this document features a food replica product containing one or more carotenoids at a concentration of between 0.00001% and 0.1% of the food product, wherein the one or more carotenoids are selected from the group consisting of β-carotene, zeaxanthin, lutein, trans-β-apo-8'-carotenal, lycopene, canthaxanthin, and combinations thereof.

This document also features a food replica product containing a vegetable juice, a vegetable puree, a vegetable extract, a fruit juice, a fruit puree, or a fruit extract at a concentration from 0.0001% to 10% of the food product. The vegetable juice, vegetable puree, vegetable extract, fruit juice, fruit puree, or fruit extract can be a *Cucumis* juice, puree, or extract (e.g., a *Cucumis* juice, puree, or extract from a cucumber or a melon). The vegetable juice, vegetable puree, vegetable extract, fruit juice, fruit puree, or fruit extract can have been cooked or otherwise treated to denature proteins before being added to the food replica product. For example, the vegetable juice, vegetable puree, vegetable extract, fruit juice, fruit puree, or fruit extract can have been heated to a temperature of about 60° C. to about 100° C. before being added to the food replica product.

In some embodiments, the food replica products provided herein can be free of animal products, wheat gluten, soy protein, and/or tofu.

Any of the food replica products provided herein can contain one or more of a meat dough, a carbohydrate-based gel, a non-animal fat, and a binding agent.

Any of the food replica products provided herein can be a meat replica. Further materials and methods for making meat replicas can be found in, for example, U.S. Publication No. 2014/0193547, and PCT publications WO 2014/110532 and WO 2014/110539, each of which is incorporated herein by reference in its entirety.

Any of the food replica products provided herein can be a cheese replica. The cheese replica can contain a nut milk, a cross-linking enzyme, or a cheese culture. Further materials and methods for making cheese replicas can be found in, for example, U.S. Publication No. 2014/0127358, and PCT publication WO 2014/110540, both of which are incorporated herein by reference in their entirety.

In yet another aspect, this document features a ground meat replica containing (a) a dough that contains an isolated plant protein, an optional edible fibrous component, one or more optional flavoring agents, and an optional fat; (b) a fat, the fat optionally containing a flavoring agent and/or an isolated plant protein; and (c) a carbohydrate-based gel, a binding agent, a highly conjugated heterocyclic ring complexed to an iron ion and/or an iron salt, an optional edible fibrous component, and one or more optional flavoring agents. The binding agent can be an isolated plant protein (e.g., a RuBisCO, an albumin, a gluten, a conglycinin, or mixtures thereof). The denaturation temperature of the binding agent can be between about 40° C. and about 80° C.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

BRIEF DESCRIPTION OF DRAWINGS

FIG. 1 is a Table showing flavor compounds affect by the addition of carotenoids in wheat gluten flour upon cooking. Data collected by SPME GCMS.

DETAILED DESCRIPTION

In general, this document provides methods and materials for producing meat replicas, including ground meat replicas (e.g., ground beef, ground chicken, ground turkey, ground lamb, or ground pork), as well as replicas of cuts of meat and fish. Broadly, the document provides methods for making ground meat replicas that include preparing a meat replica dough (referred to herein as "meat dough") that includes an optional edible fibrous component, combining the meat dough with a fat (typically a non-animal-based fat, although it is to be noted that an animal-based fat could be used) that can optionally include a flavoring agent and/or an isolated plant protein, adding a carbohydrate-based gel, an optional edible fibrous component, a binding agent, a highly conjugated heterocyclic ring complexed to an iron ion and/or an iron salt, and one or more flavoring agents to make the replica. After combining the meat dough with the fat, the mixture can be broken into smaller pieces before adding further ingredients.

The meat dough can incorporate an edible fibrous component to help achieve a textural heterogeneity and fibrousness in the meat replica that resembles the heterogeneity and texture of ground meat (e.g., ground beef). Incorporating flavoring agents into multiple components of the meat replica (e.g., two or more of the meat dough, the edible fibrous component, the non-animal-based fat, or the assembled replica), helps mimic the sensory properties of ground meat. In some embodiments, flavoring agents are incorporated into three components of the meat replica. In some embodiments, flavoring agents are incorporated into four components of the meat replica.

As described herein, the flavoring agents can be flavor precursors, flavor compounds produced from reacting flavor precursors with iron, or flavorings such as extracts (e.g., a malt extract, a yeast extract, a vegetable or fruit extract, such as a cucumber extract or a melon extract, or a peptone) or protein hydrolysates such as vegetable protein hydrolysates, soy protein hydrolysates, yeast protein hydrolysates, algal protein hydrolysates, or meat protein hydrolysates or flavor compounds, natural or synthetic. Flavor precursors can react, e.g., with the iron in a highly conjugated heterocyclic ring complexed to an iron ion or an iron salt, with each other, or with flavorings, upon heating. Accordingly, in the meat replicas described herein, combinations of pre-cooked, i.e., reacted, flavor components, uncooked flavor precursors that can react (e.g., with the iron salt and/or highly conjugated heterocyclic ring complexed to an iron ion or with each other) during cooking of the replicas, or flavorings or flavor compounds that introduce a flavor without requiring a reaction, can be incorporated into the meat replica to reproduce the sensory experience of cooking and eating cooked ground meat. The flavor and/or aroma profile of the ground meat product can be modulated by the type and concentration of the flavor precursors, the pH of the reaction, the length of cooking, the type and amount of iron complex (e.g., a heme-cofactor such as a heme-containing protein, or heme bound to non-peptidic polymer or macromolecule), the temperature of the reaction, and the amount of water activity in the product, among other factors.

A highly conjugated heterocyclic ring complexed to an iron ion is referred to herein as an iron complex. Such iron complexes include heme moieties or other highly conjugated heterocylic rings complexed to an iron ion. "Heme" refers to a prosthetic group bound to iron ($Fe^{2+}$ or $Fe^{3+}$) in the center of a porphyrin ring. Thus, an iron complex can be a heme moiety, or a porphyrin, porphyrinogen, corrin, corrinoid, chlorin, bacteriochorophyll, corphin, chlorophyllin, bacteriochlorin, or isobacteriochlorin moiety complexed to an iron ion. The heme moiety can be a heme cofactor such as a heme-containing protein; a heme moiety bound to a non-peptidic polymer or other macromolecule such as a liposome, a polyethylene glycol, a carbohydrate, a polysaccharide, or a cyclodextrin.

In some embodiments, the iron complex is a heme-containing protein that is isolated and purified. As used herein, the term "isolated and purified" with respect to a protein or a protein fraction indicates that the protein or protein fraction has been separated from other components of the source material (e.g., other animal, plant, fungal, algal, or bacterial proteins), such that the protein or protein fraction is at least 50% (e.g., at least 55%, 60%, 65%, 70%, 75%, 80%, 85%, 90%, 95%, or 99%) free, by dry weight, of the other components of the source material.

As used herein, an "enriched" protein or protein fraction composition is at least 2-fold (e.g., at least 3-fold, 4-fold, 5-fold, 10-fold, 20-fold, 50-fold, or 100-fold) enriched in that protein or protein fraction relative to the source material.

The term "heme containing protein" can be used interchangeably with "heme containing polypeptide" or "heme protein" or "heme polypeptide" and includes any polypeptide that can covalently or noncovalently bind a heme moiety. In some embodiments, the heme-containing polypeptide is a globin and can include a globin fold, which comprises a series of seven to nine alpha helices. Globin type proteins can be of any class (e.g., class I, class II, or class III), and in some embodiments, can transport or store oxygen. For example, a heme-containing protein can be a non-symbiotic type of hemoglobin or a leghemoglobin. A heme-containing polypeptide can be a monomer, i.e., a single polypeptide chain, or can be a dimer, a trimer, tetramer, and/or higher order oligomer. The life-time of the oxygenated $Fe^{2+}$ state of a heme-containing protein can be similar to that of myoglobin or can exceed it by 10%, 20%, 30%, 50%, 100% or more under conditions in which the heme-protein-containing consumable is manufactured, stored, handled or prepared for consumption. The life-time of the unoxygenated $Fe^{2+}$ state of a heme-containing protein can be similar to that of myoglobin or can exceed it by 10%, 20%, 30%, 50%, 100% or more under conditions in which the heme-protein-containing consumable is manufactured, stored, handled or prepared for consumption Non-limiting examples of heme-containing polypeptides can include an androglobin, a cytoglobin, a globin E, a globin X, a globin Y, a hemoglobin, a myoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin (e.g., HbN or HbO), a truncated 2/2 globin, a hemoglobin 3 (e.g., Glb3), a cytochrome, or a peroxidase.

Heme-containing proteins that can be used in the ground meat replicas described herein can be from mammals (e.g., farms animals such as cows, goats, sheep, pigs, ox, or rabbits), birds, plants, algae, fungi (e.g., yeast or filamentous fungi), ciliates, or bacteria. For example, a heme-containing protein can be from a mammal such as a farm animal (e.g., a cow, goat, sheep, pig, fish, ox, or rabbit) or a bird such as a turkey or chicken. Heme-containing proteins can be from a plant such as *Nicotiana tabacum* or *Nicotiana sylvestris* (tobacco); *Zea mays* (corn), *Arabidopsis thaliana*, a legume such as *Glycine max* (soybean), *Cicer arietinum* (garbanzo or chick pea), *Pisum sativum* (pea) varieties such as garden peas or sugar snap peas, *Phaseolus vulgaris* varieties of common beans such as green beans, black beans, navy beans, northern beans, or pinto beans, *Vigna unguiculata* varieties (cow peas), *Vigna radiata* (mung beans), *Lupinus albus* (lupin), or *Medicago sativa* (alfalfa); *Brassica napus*

(canola); *Triticum* sps. (wheat, including wheat berries, and spelt); *Gossypium hirsutum* (cotton); *Oryza sativa* (rice); *Zizania* sps. (wild rice); *Helianthus annuus* (sunflower); *Beta vulgaris* (sugarbeet); *Pennisetum glaucum* (pearl millet); *Chenopodium* sp. (*quinoa*); *Sesamum* sp. (sesame); *Linum usitatissimum* (flax); or *Hordeum vulgare* (barley). Heme-containing proteins can be isolated from fungi such as *Saccharomyces cerevisiae, Pichia pastoris, Magnaporthe oryzae, Fusarium graminearum, Aspergillus oryzae, Trichoderma reesei, Myceliopthera thermophile, Kluyveramyces lactis*, or *Fusarium oxysporum*. Heme-containing proteins can be isolated from bacteria such as *Escherichia coli, Bacillus subtilis, Bacillus licheniformis, Bacillus megaterium, Synechocistis* sp., *Aquifex aeolicus, Methylacidiphilum infernorum*, or thermophilic bacteria such as *Thermophilus* spp. The sequences and structure of numerous heme-containing proteins are known. See for example, Reedy, et al., *Nucleic Acids Research*, 2008, Vol. 36, Database issue D307-D313 and the Heme Protein Database available on the world wide web at http://hemeprotein.info/heme.php.

In some embodiments, a non-symbiotic hemoglobin can be from any plant. In some embodiments, a non-symbiotic hemoglobin can be from a plant selected from the group consisting of soybean, sprouted soybean, alfalfa, golden flax, black bean, black eyed pea, northern bean, tobacco, pea, garbanzo, moong bean, cowpeas, pinto beans, pod peas, quinoa, sesame, sunflower, wheat berries, spelt, barley, wild rice, and rice.

In some embodiments, a leghemoglobin can be a soy, pea, or cowpea leghemoglobin.

In some embodiments, isolated plant proteins are used. As used herein, the term "isolated" with respect to a protein or a protein fraction (e.g., a 7S fraction) indicates that the protein or protein fraction has been separated from other components of the source material (e.g., other animal, plant, fungal, algal, or bacterial proteins), such that the protein or protein fraction is at least 2% (e.g., at least 5%, 10%, 20%, 25%, 30%, 35%, 40%, 45%, 50%, 55%, 60%, 65%, 70%, 75%, 80%, 85%, 90%, 95%, or 99%) free, by dry weight, of the other components of the source material. Thus, in some embodiments, the iron complex can be a heme-containing protein (e.g., a plant heme-containing protein) that is isolated. Proteins can be separated on the basis of their molecular weight, for example, by size exclusion chromatography, ultrafiltration through membranes, or density centrifugation. In some embodiments, the proteins can be separated based on their surface charge, for example, by isoelectric precipitation, anion exchange chromatography, or cation exchange chromatography. Proteins also can be separated on the basis of their solubility, for example, by ammonium sulfate precipitation, isoelectric precipitation, surfactants, detergents or solvent extraction. Proteins also can be separated by their affinity to another molecule, using, for example, hydrophobic interaction chromatography, reactive dyes, or hydroxyapatite. Affinity chromatography also can include using antibodies having specific binding affinity for the heme-containing protein, nickel nitroloacetic acid (NTA) for His-tagged recombinant proteins, lectins to bind to sugar moieties on a glycoprotein, or other molecules which specifically binds the protein.

Example 2 describes a method for isolating RuBisCO from a plant (e.g., spinach or alfalfa). The extraction process can be improved further by adding reductants such as metabisulfite (about 2% w/v solution or more) to the initial extraction buffer and maintaining anaerobic conditions through the process and/or by adding 0.05-1% v/v cationic flocculants such as Superfloc 781G, Magnafloc LT 7989 (BASF), or Tramfloc 863A to the extraction buffer to the extraction buffer. The resuspended protein pellet from such methods, upon microfiltration at a pH of 7.0, would still perform, provide the same color, and have the same denaturation properties.

Example 4 describes a method for isolating conglycinin (also can be referred to as a 7S fraction) from a plant such as soybean. Other sources of 7S include seeds such as, without limitation, peas, chickpeas, mung beans, kidney beans, fava beans, cowpeas, pine nuts, rice, corn, and sesame. Soluble proteins can be extracted from defatted soybean flour, and then the mixture acidified (e.g., to a pH of 4.5) to precipitate the proteins. Conglycinin can be resolubilized and concentrated, e.g., using ultrafiltration.

In some embodiments, the isolated protein is decolorized. For example, the RuBisCO concentrates can be decolorized (pH 7-9) by passing over columns packed with activated carbon. The colorants can bind to the column while RuBisCO can be isolated in the filtrate. Alternatively, RuBisCO concentrates can be decolorized by incubating the solution with a FPX66 (Dow Chemicals) resin packed in a column or batch mode. The slurry is incubated for 30 minutes and then the liquid is separated from the resin. The colorants can bind to the resin and RuBisCO can be collected in the column flow-through.

In some embodiments, the isolated protein can be purified and decolorized as described in Example 3. See also "Methods for Extracting and Purifying Native Proteins" filed on Oct. 1, 2014, U.S. Ser. No. 62/058,211.

In some embodiments, a decolorized isolated plant protein can provide an increased shelf-life stability to the red color of the meat replica as compared to a corresponding meat replica including an isolated plant protein without decolorization. In some embodiments, the decolorized protein lead to an improved flavor profile of the meat replica as compared to that observed in a meat replica with the corresponding isolated plant protein without decolorization.

Heme-containing or other proteins also can be recombinantly produced using polypeptide expression techniques (e.g., heterologous expression techniques using bacterial cells, insect cells, fungal cells such as yeast, plant cells such as tobacco, soybean, or *Arabidopsis*, or mammalian cells). For example, leghemoglobin can be recombinantly produced in *E. coli* or *Pichia pastoris* as described in Example 1. In some cases, standard polypeptide synthesis techniques (e.g., liquid-phase polypeptide synthesis techniques or solid-phase polypeptide synthesis techniques) can be used to produce heme-containing proteins synthetically. In some cases, in vitro transcription-translation techniques can be used to produce heme-containing proteins.

In some embodiments, the meat replicas described herein are substantially or entirely composed of ingredients derived from non-animal sources, e.g., plant, fungal, or microbial-based sources. In some embodiments, a meat replica may include one or more animal-based products. For example, a meat replica can be made from a combination of plant-based and animal-based sources.

Making the Meat Replica

A meat dough can be prepared by mixing an isolated plant protein and an optional edible fibrous component, an optional flavoring agent, and optional non-animal fat, and adding an aqueous component such as water or a broth to the mixture and kneading or otherwise mixing, manually or mechanically, to form a dough. The aqueous component can be heated before adding to the mixture of plant protein and fibrous component. Once the meat dough is formed, the meat dough is heated (e.g., steamed or boiled) to a temperature ranging from 150° F. to 250° F. (e.g., 160° F. to 240° F., 170° F. to 230° F., 180° F. to 220° F., or 190° F. to 212° F.). For example, a meat dough can be steamed by placing in a rice cooker, steam cabinet, or tunnel steamer. A meat dough can be heated by applying dry heat, for example, by placing in a bread maker or oven, or by immersing in hot water or broth. Boiling in broth can improve the meat dough flavor because beneficial flavors and off-flavor masking agents can be absorbed into the dough. Texture properties may also be modulated by choice of the cooking method.

As used herein, the term "isolated plant protein" indicates that the plant protein (e.g., a heme-containing protein, wheat gluten, dehydrin protein, an albumin, a globulin, conglycinin, glycinin, or a zein, or mixtures thereof) or plant protein fraction (e.g., a 7S fraction) has been separated from other components of the source material (e.g., other animal, plant, fungal, algal, or bacterial proteins), such that the protein or protein fraction is at least 2% (e.g., at least 5%, 10%, 20%, 25%, 30%, 35%, 40%, 45%, 50%, 55%, 60%, 65%, 70%, 75%, 80%, 85%, 90%, 95%, or 99%) free, by dry weight, of the other components of the source material. For example, wheat gluten can be used alone or in combination with one or more other proteins (e.g., dehydrins). Dehydrins can be particularly useful for enhancing the juiciness and texture in the ground meat replicas. In some embodiments, the meat replica can be formulated to be gluten free, and, for example, a blend of maize starch, tapioca flour, rice flour, and guar gum can be substituted for the wheat gluten in the meat dough.

The edible fibrous component can be a plant fiber, an extruded mixture of isolated plant proteins (e.g., wheat gluten or other isolated plant protein, such as glutelins, albumins, legumins, vicillins, convicillins, glycinins and protein isolates such as from any seed or bean, including soy, pea, lentil, etc.), or a solution-spun protein fiber. In some embodiments, the solution-spun protein fiber is a prolamin solution-spun protein fiber. The prolamin can be from any plant source (e.g., corn or pea) and can include zein, prolamin, kafirin, secalin, hordein, or avenin. The texture of the ground meat product (e.g., meat patty) depends on properties of the edible fibrous component such as fibrousness and tensile strength. As described herein, the extruded mixture of isolated plant proteins or solution spun protein fibers can be referred to as connective tissue replicas and the fibrousness and tensile strength of the connective tissue replicas can be controlled by co-variation of extrusion parameters such as temperature, throughput, and die size. For example, combinations of lower extrusion temperatures, medium/low throughputs and smaller dies favor production of highly fibrous tissues with low tensile strength, while higher extrusion temperatures, higher throughputs and larger dies favor production of low fibrousness tissue replicas with very high tensile strengths.

The fibrousness and tensile strength of connective tissue replicas also can be modulated by changing the composition of the extrusion mixture. For example, by increasing the ratio of isolated plant protein (e.g., soy protein such as conglycinin) to wheat gluten to 3:1 w/w, and simultaneously decreasing water content in the extrusion mixture to 50%, a connective tissue replica with thinner fibers and larger tensile strength can be made.

The texture of a meat dough also can be modified by adding cream of tartar to the preparation. For example, meat dough preparations containing cream of tartar may be more cohesive, with a form factor after grinding that is similar to ground beef, such that it is readily shaped. Cream of tartar can be added between 0.05% and 2.5% (e.g., 0.5%).

The appearance of the ground meat replica can be modulated by shredding the edible fibrous component into pieces of the desired size and shape. In some embodiments, edible fibrous component can be shredded using commercial shredders, e.g., a Cuisineart chopper/grinder, UM 12 with a dull blade attachment, Comitrol shredder (Urschel Laboratories, Indiana) or a similar shredder. The size of the fibers can be adjusted to imitate the fibrous appearance of meat by the type of shredder, choice of blade, and screen type, and adjusting the time of shredding.

In other embodiments, the edible fibrous component can be separated into fibers by carding, using hand-held carders or carding machines, for example, Pat Green carder. By varying the size and spacing of pins on the carding drums, the size of the fibers can be adjusted to imitate the fibrous appearance of meat.

In other embodiments, the edible fibrous component can be separated into fibers by pushing it through rollers (for example, a KITCHENAID® pasta attachment), followed by gentle shredding using, for example, a dull blade on a UM 12 machine. By varying the number of rollers and the spacing between the rollers, the size of the fibers can be adjusted to imitate the fibrous appearance of meat.

The fibrousness, tensile strength, and appearance of the connective tissue replicas can be tailored to imitate specific ground meat products (e.g., ground beef or different cuts of beef that can be ground).

In some embodiments, the edible fibrous component includes soluble or insoluble plant fibers. For example, plant fibers from carrot, bamboo, pea, broccoli, potato, sweet potato, corn, whole grains, alfalfa, kale, celery, celery root, parsley, cabbage, zucchini, green beans, kidney beans, black beans, red beans, white beans, beets, cauliflower, nuts, apple skins, oats, wheat, or psyllium, or a mixture thereof, can be used as the edible fibrous component.

In some embodiments, the edible fibrous component can include compounds that prevent development of off-flavors during the extrusion process. High temperature and low moisture conditions to which the extrusion mixture is exposed during the extrusion process lead to formation of compounds associated with grainy, woody, nutty, rubbery and other off-flavors. Including certain classes of compounds such as antioxidants or carotenoids can help reduce the formation of off-flavor compounds. For example, the extruded mixture can include canthaxanthin to prevent development of grainy off-flavors. Carotenoids can be about 0% to about 1% by weight of the edible fibrous component.

In some embodiments, meat doughs are formed using roughly equal proportions of isolated plant protein and edible fibrous component. It will be appreciated that the ratio can be varied as desired to tailor the properties of the end product.

In some embodiments, a broth such as a flavored broth can be used in the meat dough. For example, a meat dough can be formed using roughly equal proportions of isolated plant protein and a broth.

In some embodiments, a flavor broth includes flavor mixtures created by pre-reacting (cooking) flavor precursors before adding into the meat dough. Flavor precursor molecules or compositions can be added to a pre-reaction mixture in purified form and/or can be derived from ingredients in the uncooked meat dough that contain and/or are enriched with one or more of the particular flavor precursors or compositions, including, for example, coconut oil, cysteine, glucose, ribose, thiamine, algal oil, lactic acid, and or yeast extract. The resultant flavor and/or aroma profile can be modulated by the type and concentration of the flavor precursors, the pH of the reaction, the length of cooking, the temperature of cooking, the type and amount of iron complex (e.g., an iron containing protein, a heme cofactor such as a heme-containing protein, or ferrous chlorophyllin) or iron salt (iron gluconate), the temperature of the reaction, and the amount of water activity in the product, among other factors. The flavor broth can contain non-animal products (e.g., plant) or it can be a combination of animal and non-animal based precursors (e.g., lard). The flavor broth can bring flavors into the consumable food product that result in taste and smell of beef, bacon, pork, lamb, goat, turkey, duck, deer, yak, bison, chicken or desirable meat flavor.

In some embodiments, a flavored broth can be made by combining an iron complex (e.g., an isolated heme-containing protein) and/or an iron salt (e.g., iron gluconate, iron chloride, oxalate, nitrate, citrate, ascorbate, ferrous sulfate, ferric pyrophosphate, or any other aqueous soluble salt) with one or more flavor precursors and a fat (e.g., a non-animal-based fat), and heating the mixture to obtain a flavored broth containing one or more flavor compounds. Suitable flavor precursors include sugars, sugar alcohols, sugar derivatives, free fatty acids, triglycerides, alpha-hydroxy acids, dicarboxylic acids, amino acids and derivatives thereof, nucleosides, nucleotides, vitamins, peptides, phospholipids, lecithin, pyrazine, creatine, pyrophosphate and organic molecules. For example, sugars, sugar alcohols, sugar acids, and sugar derivatives can include glucose, fructose, ribose, sucrose, arabinose, glucose-6-phosphate, fructose-6-phosphate, fructose 1,6-diphosphate, inositol, maltose, mannose, glycerol, molasses, maltodextrin, glycogen, galactose, lactose, ribitol, gluconic acid, glucuronic acid, amylose, amylopectin, or xylose. Free fatty acids can include caprylic acid, capric acid, lauric acid, myristic acid, palmitic acid, palmitoleic acid, stearic acid, oleic acid, linoleic acid, alpha linolenic acid, gamma linolenic acid, arachidic acid, arachidonic acid, behenic acid, eicosapentaenoic acid, petroselinic acid or erucic acid. Triglycerides can include fatty acid esters of caprylic acid, capric acid, lauric acid, myristic acid, palmitic acid, palmitoleic acid, stearic acid, oleic acid, linoleic acid, alpha linolenic acid, gamma linolenic acid, arachidic acid, arachidonic acid, behenic acid, eicosapentaenoic acid, petroselinic acid or erucic acid. Amino acids and derivatives thereof can include cysteine, cystine, a cysteine sulfoxide, allicin, selenocysteine, methionine, isoleucine, leucine, lysine, phenylalanine, threonine, tryptophan, 5-hydroxytryptophan, valine, arginine, histidine, alanine, asparagine, aspartate, glutamate, glutamine, glycine, proline, serine, tyrosine, ornithine, carnosine, citrulline, carnitine, ornithine, theanine, and taurine. Phospholipids can include a plurality of amphipathic molecules comprising fatty acids, glycerol and polar groups. The fatty acids are selected from the group consisting of oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, conjugated oleic acid, or esters of: oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, or conjugated oleic acid, or glycerol esters of oleic acid, palmitoleic acid, palmitic acid, myristic acid, lauric acid, myristoleic acid, caproic acid, capric acid, caprylic acid, pelargonic acid, undecanoic acid, linoleic acid, 20:1 eico-sanoic acid, arachidonic acid, eicosapentanoic acid, docosohexanoic acid, 18:2 conjugated linoleic acid, or conjugated oleic acid, or triglyceride derivatives of oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, or conjugated oleic acid. In some embodiments, the polar groups are selected from the group consisting of choline, ethanolamine, serine, phosphate, glycerol-3-phosphate, inositol and inositol phosphates.

Nucleosides and nucleotides can include inosine, inosine monophosphate (IMP), guanosine, guanosine monophosphate (GMP), adenosine, or adenosine monophosphate (AMP). Vitamins can include thiamine, Vitamin B2, Vitamin B9, Vitamin C, 4-aminobenzoic acid, choline, niacin, Vitamin B8, Vitamin B12, biotin, Betaine, Vitamin A, beta carotene, Vitamin D, Vitamin B6, or Vitamin E. Acids such as acetic acid, caffeic acid, glycolic acid, aspartic acid, pantothenic acid, alpha hydroxy acids such as lactic acid or glycolic acid, tricarboxylic acids such as citric acid, or dicarboxylic acids such as succinic acid or tartaric acid. Peptides and protein hydrolysates can include glutathione, vegetable protein hydrolysates, soy protein hydrolysates, wheat protein hydrolysates, corn protein hydrolysates, yeast protein hydrolysates, algal protein hydrolysates, and meat protein hydrolysates. Extracts can include a malt extract, a yeast extract, or peptone.

For example, in some embodiments, a broth can be made by combining an iron complex (e.g., an isolated and purified heme-containing protein such as leghemoglobin) and/or an iron salt (e.g., iron gluconate, iron chloride, oxalate, nitrate, citrate, ascorbate, ferrous sulfate, ferric pyrophosphate, or any other aqueous soluble salt) with one or more flavor precursors (e.g., a precursor mix shown in Table 2 or Table 13) and a fat (e.g., a non-animal-based fat), and heating the mixture to obtain a flavored broth containing one or more flavor compounds. A non-animal fat can include plant derived oils, algal oils, or oils from bacteria or fungi. Suitable plant derived oils include coconut oil, mango oil, sunflower oil, cottonseed oil, safflower oil, rice bran oil, cocoa butter, palm kernel oil, palm fruit oil, palm oil, soybean oil, rapeseed oil, canola oil, corn oil, sesame oil, walnut oil, almond oil, flaxseed, jojoba oil, castor, grapeseed oil, peanut oil, olive oil, borage oil, algal oil, fungal oil, black currant oil, babassu oil, shea butter, mango butter, wheat germ oil, blackcurrant oil, sea-buckhorn oil, macadamia oil, saw palmetto oil, conjugated linoleic oil, arachidonic acid enriched oil, docosahexaenoic acid (DHA) enriched oil, eicosapentaenoic acid (EPA) enriched oil, or margarine. The oils can be hydrogenated (e.g., a hydrogenated vegetable oil) or non-hydrogenated. Oil fractions such as stearin (e.g., palm stearin) or olein also can be used. For example, the non-animal fat can be coconut oil, or a combination of coconut oil and stearin. In some embodiments, the fat can contain non-animal (e.g., plant) products, or it can be a combination of animal and non-animal based precursors (e.g., lard), or exclusively animal-based fat.

In some embodiments, a flavored broth can be made by combining water, a non-animal based fat such as coconut oil, and a flavoring agent such as an acid (e.g., lactic acid), a carotenoid (e.g., lutein), or an antioxidant, and heating the mixture to make a broth.

After heating the meat dough as described above, a non-animal fat optionally containing a flavoring agent can be combined with the meat dough. Typically, the meat dough is allowed to cool (e.g., to room temperature) before combining the meat dough with the non-animal fat. The non-animal fat can be flavored by combining the non-animal fat with an iron complex or iron salt and one or more flavor precursors (described above) and heating the mixture to produce the flavor compounds. The heated mixture can be cooled so that the non-animal-based fat can solidify. One or more additional non-animal fats (e.g., algal oil), one or more masking agents (e.g., a lactone such as butyrolactone, delta-tridecalactone, gamma decalactone, delta-dodecalactone, γ-octalactone, dihydro-5-methyl 2(3H)-furanone, 4-hydroxy-2,5-dimethyl-3(2H)-furanone, 5-ethyl-4-hydroxy-2-methyl-3(2H)-furanone, δ-tetradecalactone, or combinations thereof), or one or more flavoring compounds (e.g., acetoin, carotenoid, antioxidant, vegetable or fruit juice, puree, or extract) can be added before the mixture solidifies to improve the flavor of the non-animal fat. In some embodiments, a combination of 5-ethyl-4-hydroxy-2-methyl-3 (2H)-furanone, butyrolactone, γ-octalactone, and/or δ-tetradecalactone can be used as a masking agent. Adding one or more lactones (e.g., at a concentration of $10^{-3}$ to $10^{-10}$) can result in a decrease in off flavors perceived as grain, eggy, bitterness, cardboard, livery, or mushroom and increase desired flavors such as creamy, buttery, caramelized, fatty, fresh, and fruity. For example, combinations of two, three, or four lactones can be used to mask properties such as bitterness. In addition, lactones also can be used at concentrations between $10^{-3}$ to $10^{-11}$ to provide desired flavors such as creamy, buttery, caramelized, fatty, fresh, fruity, tallow and meaty notes to the meat replica. Thus, lactones can be used as masking agents or as flavoring agents. Lactones can act as masking agents in other products, including, without limitation, dairy replicas such as milks, cheeses, and yogurts, or protein supplements such as protein bars and protein powders. Combinations of lactones can provide a unique flavor profile important in creating meat flavors (e.g., fatty tallow and sweet aromatics) in a food product such as a meat replica or providing a beef flavor to a non-beef food product. The meat replicas improve in overall liking and meatiness rating when lactones are added to the product. In some embodiments, for example, a combination of butyrolactone, delta-tetradecalactone, and 5-ethyl-4-hydroxy-2-methyl-3(2H)-furanone can be used to provide a meaty flavor. Lactones can be added to vegetable oil to make the fat taste more like animal fat and have an increase in perception of mouth coating. The lactones also can be added to increase the sweetness of the product without a change in the sugar content. It is to be noted that agents such as lactones and carotenoids can be used to flavor food replicas (e.g., plant-based food replicas), including meat or cheese replicas, and also can be used to alter the flavor of food products such as meats and cheeses (e.g., to increase meat or cheese flavors).

In some embodiments, carotenoids such as β-carotene, zeaxanthin, lutein, trans-β-apo-8'-carotenal, lycopene, and canthaxanthin can be used to control the creation of desirable flavors and prevent undesirable flavors from being created in food products such as plant based food products (e.g., meat replicas described herein). Carotenoids can be used to reduce off plant flavors in other food products, including dairy replicas. It was found that each type of carotenoid had different properties in creating desirable flavors and controlling off flavors. See, Examples 18 and 26. The carotenoids can increase sweet and fatty notes that improve meat replicas when added between 0.00001% and 0.1%.

Carotenoids can be added to the meat replica by adding them into the flavor emulsion or the flavor broth. The carotenoids can be added before or after cooking. The carotenoids can be added between 0.00001% and 0.1%. When the carotenoids are added before cooking, they can act as a substrate in the reaction flavor mixtures creating the flavors before their addition into a meat replica. The carotenoids also change the pathway for other flavors being generated by acting as antioxidant. With the addition of carotenoids, the flavor emulsion can have improved flavor quality; there is a decrease in off oxidized notes (waxy, fishy, painty), decrease in other off notes (earthy, mushroom, grainy, beany), and an increase in sweet, fatty, meaty, and fresh flavors. Each carotenoid has different resulting flavor profiles. For example, adding lycopene to the flavor emulsion before cooking results in a bland flavor, whereas β-carotene is very flavorful with added fatty and meaty notes compared to the control. The flavor profile of adding the carotenoids before cooking has a large effect on the flavor profile. When adding carotenoids after cooking, there can still be beneficial effects especially in terms of decreasing off flavor generated with storage. Other flavor precursor molecules in the flavor emulsion or flavor broth have an impact on the effect of the carotenoids. The resultant flavor and/or aroma profile can be modulated by the type and concentration of the flavor precursors, the pH of the reaction, the length of cooking, the temperature of cooking, the type and amount of iron complex (e.g., a heme cofactor such as a heme-containing protein, or ferrous chlorophyllin) or iron salt (iron gluconate), the temperature of the reaction, and the amount of water activity in the product, among other factors, all of which change how the carotenoids change the flavor profile. Particular examples include how carotenoids can reduce or prevent the creation of flavor compounds generated in plant oils, particularly when there is metal in the oil source. Carotenoids, when added to flavor emulsions with fat and oils that have poly unsaturated fatty acids like linoleic, gamma linoleic, DHA, and EPA, can prevent off fishy, painty, and vegetable flavor notes and facilitate the generation of meatiness, and sweet notes.

Particularly carotenoids can reduce grainy, woody, earthy, mushroom, planty and oxidized notes. Carotenoids can be added to different parts of plant-based products to have different impact. Carotenoids can reduce or prevent the creation off flavor compounds generated in wheat flours including wheat gluten. For example, lutein can be added to raw meat dough and reduce overall flavor intensity, reduce grain, woody, and oxidized notes in the cooked meat dough and in the final product. These changes in flavor character is supported by reduction in particular flavor compounds as seen by SPME Gas chromatography-mass spectrometry (GC-MS) in some cases and in other cases there is no change in flavor compounds but an observed reduction in the grain character, suggesting that carotenoids act by changing chemical reactions that are taking place and by masking particular flavors. Additionally, carotenoid added to the meat dough resulted in the samples being described as more fatty and sweeter than the control without carotenoids. The main compounds that decreased with lutein included oxidized flavor compound like alcohols and aldehydes, including (Z)-2-nonenal, (E,E)-2,4-nonadienal, and 1-penten-3-ol; additionally, sulfur compounds were decreased with lutein, including methanethiol, 2-acetylthiazole, and dimethyl sulfide; many of these compounds were also described as grainy and oxidized notes by trained flavor scientist by Gas Chromatography-Olfactometry (GCO).

Antioxidants such as epigallocatechin gallate (EGCG) also can be used to reduce off flavors in food products such as plant-based products (e.g., a meat replica). Antioxidants like EGCG, which is found in (and can be purified from) green tea extracts, can be added from 0.0001% and 0.1%. Antioxidants including EGCG also can be added to meat dough and change the flavor profile of both the cooked meat dough and the consumer products created from the dough. The EGCG decreases the overall flavor of the dough and particular decreases off flavors like grainy, and oxidized flavors as described by trained flavor scientist and confirmed using GCMS.

Vegetables or fruits (juice, purees, or extracts) can be added to meat replicas to increase the perceived meat flavor (e.g., the meatiness) and likeability of the products, as well as increase the perceived fattiness and fat mouth coating. Additionally, they can cause tasters to have an increase in salivation when eating the products, leading to an increase in perceived juiciness in meat replicas. The type of meat flavors that the vegetable or fruit enhances depends on the type and processing. Examples include added tallow fatty notes from cucumber and melons that are enhanced with cooking; added sweet aromatics, char meat, and savory notes from honeydew; added sweet aromatics, and freshness from pineapple and, added savory, browned meat flavor from tomato.

The vegetable or fruit can be added to meat replicates in the form of juices, purees, extracts created from pressing, juicing, stream distillate, pressure distillation, solvent assisted flavor extraction, or other methods. The vegetable or fruit can be uncooked or untreated, or can be cooked or otherwise treated (e.g., by pasteurization or by enzyme inactivation) to denature proteins (e.g., lipoxygenase). The flavor profiles—both meatiness and amount of off notes, including green or vegetable notes of the fruit or vegetable—can change depending on cooking or other treatment, and depending on the amount and process of cooking or other treatment. Many of the flavors in fruit and vegetable extracts, purees, and juices are created by enzymes. These enzymes can create desirable or undesirable flavors, and the desired flavor depends upon the application for the extracts and juices. Selection of the appropriate type of fruit or vegetable and treatment allows the creation of flavors appropriate for meat replicas. In addition, during processing it can be desirable to deactivate enzymes that can cause off flavors. A particular enzyme that can generate off flavors in the extracts when added to meat replicates is lipoxygenase, which is particularly active in the skin of fruits and vegetables. Disruption of the skin can increase lipoxygenase activity. Therefore, enzyme inactivation before cutting the skin of the fruit or vegetable can help to reduce off flavors. In the generation of fruit and vegetable extracts, purees, or juices, the enzymes can be deactivated by heating above 60° C., high pressure pasteurization, or enzyme inhibition. In some embodiments, for example, lipoxygenase can be inhibited by the addition of inhibitors such as epigallocatechin gallate (EGCG), or by addition of other redox active enzymes. In some embodiments, the whole fruit or vegetable can be cooked or treated before penetrating the skin or cooking can occur after cutting of the product. The cooking or other treatment can be rapid (minutes) or long (hours). When cooking is used, the temperature can be slightly elevated from room temperature to under pressure above 120° C. For example, the fruit or vegetable can be cooked at a temperature of 60-100° C. (e.g., 70-80° C., 80-90° C., or 90-100° C.). The process can include blending, straining, and or pressing. The seeds can be removed in some cases or the seeds can remain.

For example, cucumber puree added to a meat replica can provide additional fatty tallow flavor but can also bring green vegetable notes along. When the fruit is cooked first, there is a decrease in a few compounds including but not limited to 2-nonenal and 2,6-nonadienal that are responsible for the green, and strong cucumber notes. Additionally, there is an increase in buttery, fatty, and tallow flavors, which could come from an increase in the concentration of lactones as seen by SPME GC-MS. The cooking of tomatoes also enhances the meaty notes while decreasing the green and tomatoes flavors.

The fruits or vegetables flavor liquids can be added to different components of the products, for example added to the meat dough before cooking, added to the fat emulsion after or before cooking, added to a gelled matrix, added to the fully assembled product, or added to the unreacted flavor broth. The extract can be added from 0.0001% for extracts to up to 10% for purees and juices.

Acids such as lactic acid can be added to the meat dough to lower the pH and change the flavor reactions that occur with cooking and processing. Beef has a pH of around 5.5; to achieve meat dough at pH 5.5 additional acidity is needed. Lactic acid brings along a desirable fresh, sourness like that seen in beef.

In other embodiments, the non-animal fat can include an isolated plant protein. For example, an emulsion can be made by combining a plant derived oil, algal oil, or oil from bacteria or fungi and an optional flavor agent with an aqueous solution of an isolated plant protein (e.g., conglycinin from soy), then homogenizing the mixture using, for example, a high-speed homogenizer and heating it for a short period of time, for example, 5 min at 90° C. Physical properties of the emulsion, such as melting temperature, firmness, brittleness, color can be modulated by using different types of isolated proteins, changing the protein concentration, oil-to-water ratio, speed of homogenization, heating temperature and heating time. For example, emulsions with a high oil-to-water ratio and low protein concentration are more brittle and melt easier, while emulsions with lower oil-to-water ratio and a higher protein concentration are softer, less brittle, and more sticky, and melt at higher temperatures.

In some embodiments, an emulsion can be made by combining a plant derived oil, algal oil, or oil from bacteria or fungi and an optional flavoring agent with an aqueous solution of isolated proteins (for example, soy conglycinin) having a pH >10 (for example, pH 12) with, for example, sodium hydroxide. Agitation, stirring or homogenization of this mixture leads to the formation of an emulsion. After the emulsion is formed, the pH can be adjusted to neutral or an acidic pH by adding, for example, hydrochloric or lactic acid. Physical properties of these emulsions can be controlled by changing protein type, protein concentration, pH level at the time of homogenization, speed of homogenization and oil-to-water ratio.

In other embodiments, an emulsion can be made by mixing a plant derived oil, algal oil, or oil from bacteria or fungi, an aqueous solution of salt and flavoring agents (e.g., flavor precursors), and emulsifiers. For example, mono/diglycerides, lecithins, phospholipids, Tween surfactants, sodium stearoyl lactylate, or DATEM (diacetyl tartaric acid ester of monoglyceride) can be used as emulsifiers. Physical properties of these emulsions can be controlled by changing emulsifier type and concentration, speed of homogenization and oil-to-water ratio.

The solidified, optionally flavor-infused and/or protein containing fat can be combined with the meat dough, and the mixture of the meat dough and non-animal fat can be broken into smaller pieces, e.g., by chopping, grinding, cutting, mincing, shearing, or tearing. In some embodiments, shearing can be applied to the dough while heating, resulting in a dough that firms up and eventually breaks into pieces during the cooking process. Accordingly, a separate step for breaking into pieces would not be necessary.

A carbohydrate-based gel and an optional binding agent can be added to the dough-fat mixture. The carbohydrate-based gels also are useful for developing the texture of the meat replica and providing juiciness to the final product without making it soggy. Typically, carbohydrate-based gels that have a melting temperature between about 45° C. and about 85° C. are used. Non-limiting examples of suitable carbohydrate-based gels include agar, pectin, carrageenan, konjac (also known as glucomannan), alginate, chemically modified agarose, or mixtures thereof.

The binding agent can be an isolated plant protein or a carbohydrate-based gel. Non-limiting examples of suitable plant proteins include RuBisCO, an albumin, a gluten, a glycinin, a conglycinin, a legumin, a globulin, a vicilin, a conalbumin, a gliadin, a glutelin, a glutenin, a hordein, a prolamin, a phaseolin, a proteinoplast, a secalin, a triticeae gluten, a zein, an oleosin, a caloleosin, a steroleosin, or mixtures thereof (e.g., albumin fractions). The plant proteins can be obtained from any source, including soy, peas or lentils. In some embodiments, useful binding agents can be obtained from a non-plant-based source. For example, egg albumin or collagen can be used as a binding agent in some embodiments.

When the binding agent is a protein, it is useful for the denaturation temperature of the protein to be less than the melting temperature of the carbohydrate-based gel. For example, the denaturation temperature of suitable protein-binding agents (e.g., RuBisCO, albumin, soybean conglycinin, or a gluten, or mixtures thereof) can be between about 40° C. and about 80° C. This allows the carbohydrate based gel to melt after the protein binding agent denatures and binds the meat replica together, and provides better texture and form to the meat replica.

In some embodiments, the proteins used as binding agents may be chemically or enzymatically modified to improve their textural and/or flavor properties. For example, proteins may be partially proteolyzed using food-grade enzymes such as papain to result in better water-release profile during gelation and cooking. In some embodiments, the proteins used as binding agents may be chemically or enzymatically modified to modify the denaturation and gelling temperature of the proteins, for example, to achieve a specific gelling temperature (e.g., 52° C. to mimic myosin or 68° C. to mimic actin). In some instances, proteins such as proteases may be used to reduce bitterness that may be present in purified protein fractions.

In some embodiments, the binding agent is a carbohydrate-based gel. For example, a carbohydrate based gel that becomes firm upon cooking to 140° F. to 190° F. (e.g., 150° F. to 180° F.). Non-limiting examples of carbohydrate-based gels include methylcellulose, modified starches such as hydroxypropylmethyl cellulose, guar gum, locust bean gum, xanthan gum, or mixtures thereof.

In addition, an iron-complex and/or an iron salt and a flavoring agent can be added to the meat replica. The iron-complex and/or iron salt can be the same or different than the iron-complex and/or iron salt used to flavor the meat dough, connective tissue replica, or non-animal-based fat. The flavoring agent can be a flavor precursor or mixture of flavor precursors (described above) such that upon cooking the meat replica, the iron-complex and/or iron salt and flavor precursor can react and produce flavor compounds. The flavoring agent also can be a flavoring such as yeast extract, hydrolyzed protein, or a flavor compound. Flavor compounds can include, for example, phenylacetic acid, (E,E)-2,4-nonadienal, aquaresin onion, oil soluble onion, p-cresol, acetonyl acetate, 4-hydroxy-2,5-dimethyl-3(2H)-furanone, (E,E)-2,4-octadienal, 2-methyl-1-butane thiol, 2-methyl-3-furyl tetrasulfide, ethyl 2-mercaptopropionate, 2-mercapto-3-butanol (mixture of isomers), n-decane-d22, oil soluble garlic, sulfurol, sulfuryl acetate, mercapto-3-butanol, spiromeat, 1-penten-3-one, 2-methyl-3-furanthiol, 2-methyl-3-tetrahydrofuranthiol, oleic acid, dipropyl trisulfide, difurfuryl disulfide, methylcyclopentenolone, 3-methylthio hexanal, butyric acid, butyrolactone, 5-methyl-2(3H)-furanone, furaneol, 1-(1H-pyrrol-2-yl)-ethanone, hexanoic acid, and combinations thereof. Additional flavor compounds may be purchased commercially from companies such as Sigma Aldrich (St. Louis, Mo.), Penta Manufacturing Co. (Fairfield, N.J.), Advanced Biotech (Totowa, N.J.), Firmenich (Meyrin, Switzerland), Givaudan (Vernier, Switzerland), International Flavors and Fragrances (New York, N.Y.), and Wild Flavors (Erlanger, Ky.).

In some embodiments, seasonings agents such as edible salts (e.g., sodium or potassium chloride), garlic, or herbs (e.g., rosemary, thyme, basil, sage, or mint), emulsifiers (e.g., lecithin), additional fiber (e.g., zein or inulin), minerals (e.g., iodine, zinc, and/or calcium), meat shelf life extenders (e.g., carbon monoxide, nitrites, sodium metabisulfite, Bombal, vitamin E, rosemary extract, green tea extract, catechins and other antioxidants) can be incorporated into the meat replica.

Meat replicas described herein also can include a natural coloring agent such as turmeric or beet juice, or an artificial coloring agent such as an azo dye, triphenylmethane, xanthene, quinine, indigoid, titanium dioxide, red #3, red #40, blue #1, or yellow #5, or any combination of natural and/or artificial coloring agents.

Any of the replicas described herein can be shaped to the desired use, e.g., formed into patties, loaves, chubs, meatballs, or nuggets, and used in any type of food product that ground meat would be used, e.g., as taco filling, or in casseroles, sauces, toppings, soups, stews, meatballs, or meatloaves. In some embodiments, a meat replica can be formed, for example, into meatballs or nuggets, and then coated with breadcrumbs, rice, or a flour (e.g., oat flour or coconut flour) for ease of convenience.

Meat Replica

A meat replica described herein can include about 5% to about 88% (e.g., about 10% to about 40%, about 25% to about 35%, about 40% to about 88%, or 45% to about 60%) by weight of a meat replica dough; about 0% to about 40% (e.g., about 15% to about 25%) by weight of a carbohydrate-based gel; about 3% to about 35% by weight of a non-animal fat (e.g., about 10% to about 15%); about 0.00001% to about 10% by weight of a flavoring agent; about 0% to about 15% (e.g., about 2% to about 15% or about 2% to about 10%) by weight of a binding agent; and about 0.01% to about 4% (e.g., about 0.05% to about 1%, or about 0.2% to about 2%) by weight of an iron complex such as a heme-containing protein and/or an iron salt. The amount of flavoring agent can vary depending on the type of flavoring agent. In some embodiments, a flavoring agent can be about 0.5% to about 7% of the meat replica. For example, a flavoring agent such as a mixture of flavor precursors can be about 0.5% to about 7% of the meat replica (e.g., about 1% to about 3%; about 3% to about 6%; about 4% to about 7%). In some embodiments, a flavoring agent such as a flavoring compound can be about 0.00001% to about 2% of the meat replica.

As described herein one or more, two or more, three or more, or four or more of the components can include a flavoring agent. For example, the meat dough can include a flavoring agent (e.g., a flavoring compound produced by combining an iron complex or iron salt with one or more flavor precursors and heating) or can include a flavoring such as yeast extract in the edible fibrous component. The non-animal fat also can include a flavoring agent (e.g., a flavoring compound produced by combining an iron complex or iron salt with one or more flavor precursors and heating). The replica also can include an iron complex or iron salt and one or more flavor precursors that can react upon cooking the replica, enhancing the sensory experience of cooking the replica. In addition, the replica can include a flavoring or flavoring compound.

In some embodiments, the components are produced at the desired particle sizes and then compressed together for 5 minutes to 24 hours (e.g., 10 minutes to 2 hours, 1 to 4 hours, 4 to 8 hours, 6 to 12 hours, or 12 to 24 hours) to allow the components to adhere into a meat replica. The meat replica may then be ground to replicate the attributes of a ground meat. The meat replica can be compressed into any desired form to replicate the shape and density of, for example, a steak, a tenderloin, a chop, or a fillet. The meat replica also may be further processed into a processed meat such as a sausage.

The invention will be further described in the following examples, which do not limit the scope of the invention described in the claims.

EXAMPLES

Example 1

Isolation and Purification of Leghemoglobin

A nucleic acid encoding *Glycine max* leghemoglobin C2 (Uniprot KB P02236) with an N-terminal His6 epitope tag and a TEV cleavage site was cloned into the pJexpress401 vector (DNA2.0), and transformed into *E. coli* BL21. Transformed cells were grown by fed-batch fermentation supplemented with kanamycin, 0.1 mM ferric chloride and 10 µg/ml 5-aminolevulinic acid. Expression was induced by 0.3 mM isopropyl β-D-1-thiogalactopyranoside (IPTG) and cells were grown at 30° C. for 24 hr. Cells were concentrated by centrifugation and resuspended in 20 mM potassium phosphate pH 7.8, 100 mM NaCl. Cells were lysed by high-pressure homogenization and clarified by centrifugation and microfiltration. Leghemoglobin was purified from the soluble lysate using zinc-charged IMAC sepharose fast flow resin (GE Healthcare). Bound leghemoglobin was eluted off the resin with 500 mM potassium phosphate monobasic, 100 mM NaCl. Purified leghemoglobin was neutralized and concentrated using ultrafiltration. Concentrated leghemoglobin was reduced with 20 mM Na dithionite. Na dithionite was removed by diafiltration. Leghemoglobin concentration was determined by soret peak absorbance and adjusted to 60-70 mg/ml. The final leghemoglobin product was frozen in liquid nitrogen, lyophilized, and stored at −20° C. Purity (partial abundance) of leghemoglobin was analyzed by SDS-PAGE and determined to be ~80%. Analysis of UV-VIS spectra (250-700 nm) revealed spectral signature consistent with heme-loaded leghemoglobin.

*Glycine max* leghemoglobin C2 and eight *Pichia pastoris* heme biosynthesis genes (listed in Table 1) were cloned into the *Pichia pastoris* expression vector pJA (BioGrammatics Inc.; Carlsbad, Calif.) under the control of the pAOX1 methanol inducible promoter. *Pichia pastoris* strain Bg11 (BioGrammatics, Inc.) was transformed with linearized plasmids, and stable integrants were selected by antibiotic resistance.

TABLE 1

| Gene | Species | Function | UniprotKB # |
| --- | --- | --- | --- |
| Leghemoglobin C2 | *Glycine max* | Leghemoglobin production | P02236 |
| ALA synthase | *Pichia pastoris* | Heme enzyme-step 1 | F2QS71 |
| ALA dehydratase | *Pichia pastoris* | Heme enzyme-step 2 | F2QZA1 |
| Porphobilinogen deaminase | *Pichia pastoris* | Heme enzyme-step 3 | F2QP90 |
| Uroporphyrinogen III synthase | *Pichia pastoris* | Heme enzyme-step 4 | F2QSR5 |
| Uroporphyrinogen III decarboxylase | *Pichia pastoris* | Heme enzyme-step 5 | F2QUW1 |
| Coproporphyrinogen oxidase | *Pichia pastoris* | Heme enzyme-step 6 | F2QUX3 |
| Protoporphyrinogen III oxidase | *Pichia pastoris* | Heme enzyme-step 7 | F2R0D |
| Ferrochelatase | *Pichia pastoris* | Heme enzyme-step 8 | F2QWX6 |
| Sh bleomycin | *Streptoalloteichus hindustanus* | Resistance to Zeocin | P17493 |
| Beta lactamase | *E. coli* | Resistance to ampicillin | Q9L5C7 |
| Hygromycin | *E. coli* | Resistance to hygromycin | P00557 |
| NatR | *Streptomyces noursei* | Nourseothricin resistance | O33583 |
| Neomycin resistance | Synthetic bacterial transposon Tn5 | Resistance to geniticin (G418) | n/a |

Transformed *Pichia* cells were grown by fed-batch fermentation and leghemoglobin expression was induced with methanol for 120 hours at 30° C. Cells were concentrated by centrifugation, resuspended in water, and lysed by high pressure homogenization. Solids were removed by treatment with Tramfloc 863A, centrifugation, and 0.2 µm microfiltration (Koch Membrane Systems). The soluble lysate was concentrated and diafiltered with water using 3 kDa ultrafiltration (Spectrum Laboratories). The formulated lysate was partially purified using HPA25L anion exchange resin (Mitsubishi) to a final purity of ~40%. The partially purified leghemoglobin solution was re-formulated by concentration and water diafiltration using 3 kDa ultrafiltration (Spectrum Laboratories) and further purified using Q Fast Flow anion exchange resin (GE Lifesciences). The final leghemoglobin product was concentrated using 3 kD ultrafiltration and frozen at −20° C. The final product was ~80% pure and contained 80 g/L leghemoglobin.

Example 2

Isolation of RuBisCO

One kg of fresh spinach leaves was macerated in a Vita-prep 3 blender (Vitamix Corp, Cleveland, Ohio) at a ratio of 1:1 with potassium phosphate buffer (pH 7.4)

containing 0.1M NaCl. The extraction was performed for 10 min at the highest setting (3HP motor). The temperature was maintained at less than 30° C. The pH was adjusted to 7.4 post-grinding using a 10 M NaOH solution. The homogenate was centrifuged at 3500 g for 5 minutes, simulating the conditions at scale (with a GEA Westfalia decanter GCE-345 at about a 1 gpm feed rate). The pellet was discarded. The liquid centrate (about 1.6 L) then was microfiltered using a 0.2 µm modified polyethersulfone (mPES) membrane in a hollow fiber format (KrosFlo K02E20U-05N from Spectrum Laboratories Inc. Rancho Dominguez, Calif.). The retentate (about 0.25 L) was diafiltered using about 1.5 L of the extraction buffer. The permeate from this filtration step (~3 L) was concentrated using a 10 kDa mPES membrane (MiniKros N02E010-05N from Spectrum Laboratories Inc. Rancho Dominguez, Calif.) to about 0.1 L. The protein concentrate had a pH of about 7.4. A concentrated acid solution such as 6M Hydrochloric Acid was slowly added to the concentrate to decrease the pH to 5. The mixture was stirred vigorously for 30 minutes using a magnetic stir plate or a homogenizer and then centrifuged at 3500 g for 5 minutes to obtain an off white pellet and a brown centrate. The centrate was discarded and the protein pellet was washed with deionized water. The pellet was resuspended in 0.05-0.1 L DI water. The solution was mixed vigorously into a uniform slurry and the pH was slowly raised to 11 using a concentrated base solution such as 10M sodium hydroxide. The resulting solution was clear yellow. The pH was then reduced to 9 to maintain the clear mixture. The product was dried using a spray dryer, or frozen and dried using a freeze dryer. This material was analyzed using a Leco FP-528 Nitrogen Combustion Analyzer (Leco, St. Joseph, Mich.) by the AAOC method (AOAC, 2000). Protein was calculated as % nitrogen×6.25 and was calculated to be 86% protein. The product obtained was slightly decolored and retained the low temperature denaturation property.

Example 3

Isolation and Decolorization of RuBisCO

One kg of fresh spinach leaves were macerated in a Vita-prep 3 bender (Vitamix Corp., Cleveland, Ohio) in a ratio of 1:1 (w/w) with potassium phosphate buffer (pH 7.4) containing 8% (w/v) PEG (Carbowax Sentry PEG 8000; Dow Chemicals, Midland, Mich.) and 0.1% (w/v) cationic flocculant (863A; Tramfloc, Inc., Houston, Tex.). The extraction was performed for 3 minutes at the highest setting (3HP motor) maintaining the temperature at less than 30° C. at all times. The pH was adjusted to 7.4 post-grinding, using a 10 M NaOH solution. The homogenate was centrifuged at 3500 g for 5 minutes using a bench top centrifuge (Allegra X15R, SX4750 rotor; Beckman Coulter, Inc., Pasadena, Calif.). The pellet was discarded and the supernatant (about 1.6 L) was collected separately. Magnesium sulfate heptahydrate salt (K+S KALI GmbH, Kassel, Germany) was added to the supernatant to attain 1M concentration. The solution was mixed thoroughly and centrifuged at 5451 g for 3 minutes using a bench top centrifuge (Allegra X15R, SX4750 rotor; Beckman Coulter, Inc.). Three layers formed in the centrifuge bottle, and the remaining green solids separated out as a pellet (about 0.1 L). The PEG layer (about 0.3 L) separated and formed the top layer, selectively fractionating the color compounds and odorous compounds. A clear product remaining in the middle layer was then microfiltered using a 0.2 µm modified polyethersulfone (mPES) membrane in a hollow fiber format (Spectrum Laboratories Inc.). The retentate (about 0.25 L) was diafiltered using about 0.75 L of 1M magnesium sulfate solution. The permeate from this filtration step (about 3 L) was concentrated using a 70 kDa mPES membrane (Spectrum Laboratories, Inc.) to about 0.1 L. This was further diafiltered with about 0.5 L DI water in 5 steps. The protein concentrate had a pH of about 7 and conductivity less than 5 mS/cm. The resulting protein concentrate was clear pale yellow. The product was dried using a spray dryer, or frozen and dried using a freeze dryer. This material was analyzed using the standard 660 nm Pierce protein assay and SDS gel densitometry. The dry solids were analyzed using the IR moisture analyzer. The flocculant and PEG concentration in the final product were analyzed using titration methods. The protein concentration was about 91% (w/w), and the total solids about 95% (w/w). The PEG and flocculant concentrations were analyzed at less than 0.2% (w/w). The product was over 90% pure with over 90% recovery through the process. The product obtained was decolored and retained the low temperature denaturation property.

Example 4

Isolation of Soluble Soybean Conglycinin

The soluble conglycinin fraction of soybean proteins (the 7S fraction) was obtained using the following method: 1 kg of defatted soy flour (CHS HONEYSOY® PDI 90) was mixed with 10 L deionized water in a vessel fitted with an overhead mixer. After the clumps of flour were dispersed, the pH of the slurry was adjusted to 8 with 2N NaOH. The mixture was stirred for 1 hour at 4° C. to extract all soluble proteins. The pH of the mixture then was adjusted to 5.8 using 2N $H_2SO_4$ and mixed for an additional 1 hour at 4° C. The mixture was then centrifuged to remove insoluble carbohydrate and protein (glycinins) at 10000 g for 10 minutes in a JLA 8.1 rotor (JHC centrifuge, Beckman Coulter Inc.). The soluble supernatant was further acidified to pH 4.5 using 2N $H_2SO_4$ and mixed for 1 hour at 4° C. The acidified mixture was then centrifuged at 10000 g for 10 minutes to collect the precipitated proteins and the supernatant containing lipoxygenase, soybean lecithin and trypsin inhibitors was discarded. The conglycinin in the pH 4.5 precipitated protein fraction was resolubilized by resuspending the pellet in 4 volumes of water (approximately 2 L) and adjusted to pH 8 using 2N NaOH. The mixture was stirred at 4° C. for 1 hr. The pH of the mixture was once again dropped to 5.8 using 2N $H_2SO_4$ to minimize co-purification of contaminant proteins. The mixture was centrifuged at 15000 g for 20 minutes to collect the soluble conglycinin in the supernatant. The conglycinin fraction was concentrated using ultrafiltration (70 kDa mPES ultrafiltration membrane, 2600 sq. cm, Spectrum Laboratories Inc.). The resulting protein solution (approx. 0.5 L at 10% protein concentration) comprises 55-65% pure conglycinin and gels at 65° C. The protein then was freeze-dried and stored at room temperature until used in making of the meat-replicas.

Example 5

Preparation of Dough Broth for Pre-Flavoring Meat Dough

A dough broth was created by mixing a 1× precursor mix 1 (see Table 2), 0.5% leghemoglobin (LegH, isolated and purified as described in Example 1), and 18% Refined, Bleached, and Deodorized (RBD) coconut oil (from Shay and company, Milwaukie, Oreg.), and stirring as the solution was heated until boiling, then simmered at a low boil for 10 minutes. This solution is referred to as the "dough broth" and was used for creating the meat dough of Example 10. Incubating the coconut oil with the LegH and precursor mix generates savory or meaty flavors in the broth including caramelized, fatty, beefy, nutty, sulfur, metallic, buttery, sweet, savory, and umami.

TABLE 2

Composition of magic mixes

| Precursor | Precursor mix 1 (mM) | Precursor mix 2 (mM) |
|---|---|---|
| Alanine | 15.0 | 7.5 |
| Arginine | 0.6 | 0.3 |
| Asparagine | 0.8 | 0.4 |
| Aspartate | 0.8 | 0.4 |
| Cysteine | 9.0 | 9.0 |
| Glutamic acid | 50.0 | 50.0 |
| Glutamine | 0.7 | 0.3 |
| Glycine | 1.3 | 0.7 |
| Histidine | 0.6 | 0.3 |
| Isoleucine | 0.8 | 0.4 |
| Leucine | 2.0 | 1.0 |
| Lysine | 5.0 | 2.5 |
| Methionine | 1.0 | 0.5 |
| Phenylalanine | 0.6 | 0.3 |
| Proline | 0.9 | 0.4 |
| Threonine | 0.8 | 0.4 |
| Tryptophan | 1.5 | 0.8 |
| Tyrosine | 0.6 | 0.3 |
| Valine | 1.0 | 0.5 |
| Glucose | 5.6 | 2.8 |
| Ribose | 5.0 | 5.0 |
| Thiamine | 0.2 | 0.2 |
| IMP + GMP | 2.0 | 1.0 |
| Lactic acid | 9.0 | 4.5 |
| Creatine | 3.0 | 1.5 |
| L-Taurine | 40.0 | 20.0 |
| Glutathione | 2.0 | 1.0 |
| N-Acetyl L-cysteine | 10.0 | 5.0 |

Example 6

Preparation of Flavor Infused Fat Replica

A flavored fat replica was created by mixing a solution of LegH (from Example 1) at 0.5%, 1× precursor mix 1 (Table 1), and 30% RBD coconut oil (Shay and company, Milwaukie, Oreg.) and stirring the mixture as it was heated until boiling, then simmered at a low boil for 10 minutes. The solution was cooled to allow the oil to solidify. Once the oil was solidified, it was separated from the aqueous layer and used in preparing the burger described in Example 11. Incubating the coconut oil with the LegH and precursor mix infuses flavor notes in the oil including savory, meaty, beef fat, slightly sweet and sulfur.

Example 7

Preparation of "Soft Connective" Tissue Replica

A soft connective tissue replica was prepared using soy protein isolate (SUPRO® EX38 (Solae)), Vital wheat gluten (131100, Guisto's Specialty Foods, San Francisco, Calif.), and water. A Nano 16 extruder ((Leistritz Advanced Technologies Corp., Somerville, N.J.) was used, with a custom-made cooling die (round, ID 6.5 mm, length 300 mm), a cooling water circulator, and a high pressure water pump (Optos, Eldex Laboratories Inc.).

Fifty (50) g of soy protein isolate and 50 g of wheat gluten powder were thoroughly mixed with manual mixing and tumbling for 5 min, and then loaded into the loading tube of the extruder's batch feeder. The dry mixture was fed into the extruder at the rate of 2.4 g/min. Water was fed by the pump into the second zone of the extruder's barrel at the rate of 3.6 ml/min. Screw speed of the extruder was maintained at 120 RPM. A temperature gradient was set along the extruder barrel as follows: feed zone—25° C., zone 1—30° C., zone 2—60° C., zone 3—110° C., zone 4—110° C. The die plate was neither actively heated, nor cooled. The cooling die was cooled by the cooling water circulator maintaining the die at 24° C.

The soft connective replica produced by this method was off-white in color and highly fibrous/filamentous, with a neutral taste and flavor. Tensile strength of this material was low and comparable to that of tender beef roast.

Example 8

Preparation of "Tough Fibrous Connective" Tissue Replica

To prepare a tough fibrous connective tissue replica, 50 g of soy protein isolate and 50 g of wheat gluten powder were thoroughly mixed by manual mixing and tumbling for 5 min, and loaded into the loading tube of the extruder's batch feeder. The dry mixture was fed into the extruder at the rate of 3.6 g/min. Water was fed by the pump into the second zone of the extruder's barrel at the rate of 5.4 ml/min. Screw speed of the extruder was maintained at 120 RPM. A temperature gradient was set along the extruder barrel as follows: feed zone—25° C., zone 1—37° C., zone 2—61° C., zone 3—135° C., zone 4—135° C. The die plate was neither actively heated, nor cooled. The cooling die was cooled by the cooling water circulator maintaining the die at 26° C.

The tough fibrous connective replica produced by this method was light tan in color and was a fibrous/layered material having a neutral taste and flavor. Tensile strength of this material was high and comparable to that of cooked beef tendons.

Example 9

Preparation of Pre-Flavored "Soft Connective" Tissue

To prepare a flavored soft connective tissue replica, 50 g of soy protein isolate, 50 g of wheat gluten powder, 1 g of yeast extract #9 (Flavor house Inc., X11020), and yeast extract #21 (Biospringer 1405/40 MG1) were thoroughly mixed by manual mixing and tumbling for 5 min, and loaded into the loading tube of the extruder's batch feeder and extruded as described in Example 7. The pre-flavored soft connective tissue had a savory taste, with an increase in the flavor complexity and decrease in off notes as compared to the soft connective tissue produced in Example 7.

Example 10

Preparation of "Meat Dough"

"Meat dough" for the ground beef-replica was prepared using the following ingredients:

a. Vital wheat gluten (#131100, Guisto's Specialty Foods, San Francisco, Calif.)

b. soft connective tissue replica (see Example 7, the pre-flavored soft connective tissue of Example 9 also could be used)
c. dough broth (see Example 5)

A 100 g portion of meat dough was prepared as follows. First, 25 g of the soft connective tissue replica was hand shredded lengthwise into approximately 1-inch long pieces. The shredded soft connective replica was combined with 25 g dry wheat gluten in a mixing bowl and gently hand tossed to mix evenly. In a separate container, 50 mL of dough broth was brought to a boil and simmered on low for 10 minutes. The hot dough broth was added to the dry gluten-connective tissue replica mix and kneaded on a stand mixer (e.g., KITCHENAID® Professional 600 Series 6 Quart Bowl-Lift Stand Mixer model KP26M1XER with dough-mixing attachment, set at speed 2) for 30 seconds to form the meat dough.

Once kneaded, the meat dough was formed into a slab and transferred to another vessel for steaming. The meat dough was steamed (in an Aroma Rice cooker Model No. ARC-1030SB) until the internal temperature reached approximately 200° F. and held at that temperature for additional 20 minutes. After steaming, the dough was transferred to a container on ice to allow it to cool down to room temperature. The steamed meat dough also can be stored at this point at 4° C. for up to a week. Before forming the beef-patty replicas, the steamed meat dough was hand torn into smaller pieces, approximately 1 inch cubes. The mixture is now ready for use in the formation of a beef-patty replica (described in Examples 11 and 12).

Example 11

Assembly and Cooking of Burger

A replica burger containing the ingredients in Table 3 was prepared. The 1% agar preparation was made by adding 1 g of agar powder (item 6410, Now Foods Bloomingdale, Ill.) to 99 ml of water in a glass beaker. The agar was fully solubilized by heating the mixture to 100° C. while stirring, and then cooling in an ice bath for 20-30 min until a firm gel firmed. The gel was then transferred to a coffee grinder (Cuisinart® Model #CUI DCG-20N) and ground for 20 seconds to break it into small pieces for mixing.

TABLE 3

Composition of Burger

| Ingredient | % |
| --- | --- |
| Meat dough (Example 10) | 54.1 |
| 1% agar preparation | 20.0 |
| Coconut oil with flavor system (Example 6) | 13.5 |
| 16x precursor mix 2 (Table 1) | 5.9 |
| RuBisCO preparation (dry) (Example 2) | 5.3 |
| LegH preparation (dry) (Example 1, E. coli) | 1.2 |
| Total | 100 |

The meat dough (Example 10) and flavored coconut oil (Example 6) were mixed by hand in a bowl. A typical batch size was 100 g to 2000 g. The mixture was then ground using a stand mixer fitted with a food grinder attachment (KITCHENAID® Professional 600 Series 6 Quart Bowl-Lift Stand Mixer model KP26M1XER and KITCHENAID® Food Grinder model FGA, St. Joseph, Mich.) on speed setting 1. The mixture was fed by a screw conveyor past a rotating knife installed in front of a fixed-hole plate. The ground tissue was collected in a bowl.

The following ingredients then were added in the ratios shown in Table 3: 1% agar preparation, RuBisCO (approximately 50% by weight RuBisCO), 16× precursor mix 2, and LegH (350-650 mg/g). Ingredients were added in the order listed here and the material was mixed gently after each addition. Thirty (30) g or 90 g portions of ground tissue were then formed by hand into round patty shapes. Typical dimensions for 30 g patties were 50 mm×12 mm. Typical dimensions for 90 g patties were 70 mm×18 mm. During the assembly, grinding, and forming, all materials were kept cold (4-15° C.). Patties were refrigerated until cooked. Patties were cooked on a preheated (325-345° F.) non-stick skillet and heated to an internal temperature of 160° F. while flipping every 2 minutes. Typical cook times ranged from 12 to 15 minutes. Cooked patties had an appearance, texture, and flavor similar to ground beef as judged by a trained sensory panel. In addition to cooking in a patty format, the unformed material also can be used in a variety of dishes such as taco filling, casseroles, sauces, toppings, soups, stews, or loaves.

Example 12

Adding Flavor Molecules to the Burger

A replica burger containing the ingredients in Table 4 was prepared.

TABLE 4

Composition of burger

| Ingredient | % |
| --- | --- |
| Unflavored meat dough | 54.1 |
| 1% agar preparation (see Example 11) | 20.0 |
| Coconut oil | 13.5 |
| 16x precursor mix 2 (Table 1) | 5.9 |
| RuBisCO preparation (dry) (Example 2) | 5.3 |
| LegH preparation (dry) (Example 1, E. coli) | 1.2 |
| Phenylacetic acid (CAS # 103-82-2) | 0.003% |
| Furaneol (CAS #3658-77-3) | 0.003% |
| 2-Mercapto-3-butanol (CAS # 37887-04-0) | 0.0015% |
| Garlic, oil soluble (Kalsec) | 0.0015% |
| Total | 100 |

The unflavored meat dough (wheat gluten, unflavored soft connective tissue, and water) and coconut oil were mixed by hand in a bowl and ground as described in Example 11. The following ingredients were then added at the ratios in Table 4: 1% agar preparation, RuBisCO (approximately 50% by weight), 16× precursor mix 2, and LegH (350-650 mg/g). Flavor compounds and garlic oil were diluted to $1 \times 10^{-2}$ then added at the concentration listed in Table 4. Ingredients were added in the order listed here and the material was mixed gently after each addition. 100 g portions of ground tissue were then formed by hand into round patty shapes. During the assembly, grinding, and forming, all materials were kept cold (4-15° C.). Patties were cooked on a preheated (325-345° F.) non-stick skillet and heated to an internal temperature of 160° F. while flipping every 2 minutes. The patties typically cooked in 12 to 15 minutes. Cooked patties had appearance, texture, and flavor similar to ground beef. These patties did not have as much depth in flavor as burgers created with pre-flavored dough and fat, however these burgers had additional flavor notes associated with beef as judged by a trained sensory panel.

Example 13

Preparation of Solution-Spun Zein Fibers for Connective Tissue Replica

Solution-spun zein fibers were produced using zein powder (Prairie Gold Inc., Bloomington, Ill.), ethanol (190 proof Everclear by Luxco), sodium hydroxide (Fisher Scientific), glycerol, (Fisher Scientific), and water. Fifty (50) g of zein powder, ten (10) g of glycerol, thirty six (36) g of ethanol, and four (4) g of water were mixed in a glass jar for 5 min using a homogenizer. The pH of the solution was adjusted to 7.0 with a 1M solution of sodium hydroxide in ethanol. The solution was loaded into a 1 ml syringe with a 30-gauge needle. The syringe was mounted on a syringe pump (New Era Syringe Pumps, Inc.), which was installed vertically, needle pointing down, over a custom-made fiber spooler with a Delrin spool. The spooling rod was set to rotate at 3 RPM.

The syringe pump was set to 0.12 ml/h and activated. When a drop of solution formed at the end of the needle, it was picked up with a spatula and stretched into a fiber. The end of the fiber was touched to the spooling rod until it adhered. A heating fan, pointing to the spooling rod at the place of fiber attachment, was then switched on to facilitate fiber drying. Fiber was spooled until the syringe was empty, after which the syringe was reloaded and the above procedure repeated. After spooling, the fibers were pre-cured in a 110° C. oven for 1 hour, and then finished by baking at 175° C. for 5 minutes.

Zein fibers obtained by this process were semi-clear, light yellow colored fibers, 60-80 micrometer thick, as measured by light microscopy. They were very flexible in air and water, maintaining high tensile strength similar to animal connective tissue (10-15 MPa) even after water immersion for several hours.

Example 14

Preparation of Dough Broth with Iron Gluconate for Pre-Flavoring Meat Dough

A dough broth was created by mixing a 1× precursor mix 1 (see Table 2), 1 mM iron gluconate, and 18% refined, bleached, and deodorized (RBD) coconut oil (Shay and company), and stirring as the solution was heated until boiling, then simmered at a low boil for 30 minutes. This solution is referred to the "iron gluconate dough broth" and can be used instead of the "dough broth" that is used in the meat dough of Example 10. Incubating the coconut oil with the iron gluconate and precursor mix generates savory and or meaty flavors in the broth including pork, beefy, sulfur, metallic, sweet, savory, and umami in the broth.

Example 15

Preparation of Flavor Infused Fat Replica with Iron Gluconate

Flavored fat replica containing iron gluconate was created by mixing a solution of LegH at 0.25%, 1 mM iron gluconate, 1x precursor mix 1 (Table 1), and 30% RBD coconut oil (Shay and company) and stirring the mixture as it was heated until boiling, then simmered at a low boil for 10 minutes. The solution was cooled to 4° C. to allow the oil to solidify. Once the oil was solidified, it was separated from the aqueous layer and used instead of the flavored fat replica in preparing the burger described in Example 13. Incubating the coconut oil with the LegH, iron gluconate, and precursor mix infuses flavor notes in the oil including savory, meaty, beef fat notes, sweet, metallic and sulfur notes.

Example 16

Preparation of Meat Dough Containing Cream of Tartar

A meat dough was prepared as follows using the ingredients shown in Table 5.

TABLE 5

| Composition of Meat Dough | |
|---|---|
| Ingredient | % |
| Gluten flour | 48.2 |
| Water | 35.0 |
| Coconut oil | 9.0 |
| 1M lactic acid solution | 6.0 |
| Hydrolyzed vegetable protein | 1.3 |
| Cream of tartar | 0.5 |
| Total | 100.0 |

First, water, coconut oil, 1M lactic acid solution, and hydrolyzed vegetable protein were mixed and heated to 60° C. to make a broth. Heating was done to melt and help distribute the coconut oil. Gluten flour (vital wheat gluten #131100, Guisto's Specialty Foods, San Francisco, Calif.) and cream of tartar were mixed in a separate container. The warm broth was then added to the dry mixture and kneaded with a stand mixer (e.g., KITCHENAID® Professional 600 Series 6 Quart Bowl-Lift Stand Mixer model KP26M1XER with dough-mixing attachment, set at speed 2) for 30 seconds to form the meat dough. Once kneaded, the meat dough was formed into a slab and transferred to another vessel for steaming. The meat dough was steamed (e.g., in an Aroma Rice cooker Model No. ARC-1030SB) until the internal temperature reached approximately 88° C. After steaming, the dough was transferred to a container on ice to allow it to cool down to 4° C. Cream of tartar modified the texture of the dough in an advantageous way. When compared to the meat dough of Example 10, the meat dough of the present example was more cohesive, had a form factor after grinding that was more similar to ground beef, and had improved raw handling characteristics so that it was easier to shape and form patties.

Example 17

Preparation of Meat Dough Containing Lutein

A meat dough was prepared as follows using the ingredients shown in Table 6.

TABLE 6

| Composition of Meat Dough | |
|---|---|
| Ingredient | % |
| Water | 50 |
| gluten flour | 40 |

TABLE 6-continued

| Composition of Meat Dough | |
|---|---|
| Ingredient | % |
| coconut oil | 9.0 |
| lutein SAF preparation | 1 |
| Total | 100.0 |

First, water, coconut oil (Shay and company, Milwaukie, Oreg.), and lutein (FloraGLO Lutein 20% SAF, DSM Nutritional Products, Overland Park, Kans.) were mixed and heated to greater than 25° C. to make a broth. Heating was done to melt and help distribute the coconut oil and lutein. The warm broth was then added to gluten flour (vital wheat gluten PROLIGHT® LF, ADM, Chicago, Ill.) and kneaded with a stand mixer (e.g., KITCHENAID® Professional 600 Series 6 Quart Bowl-Lift Stand Mixer model KP26M1XER with dough-mixing attachment), set at speed "2" for 30 seconds to form the meat dough. Once kneaded, the meat dough was formed into a slab and transferred to another vessel for steaming as in Example 16 then transferred to a container on ice to allow it to cool down to 4° C. A control batch of meat dough was made as described above except no lutein was added. The meat dough containing lutein was described as having less grainy flavor and being closer to beef than the control meat dough.

Example 18

Decreasing Grain and Off Flavors by the Addition of Carotenoids

Meat dough was prepared as follows using the ingredients shown in Table 7.

TABLE 7

| Composition of Meat Dough | |
|---|---|
| Ingredient | % |
| Gluten flour (ADM PROLITE ® Low Flavor Vital Wheat Gluten (Montreal, Canada)) | 40.0 |
| Tap water | 50.0 |
| Coconut oil | 10.0 |
| Carotenoids (DSM) | 0.005 |
| Total | 100.0 |

First, melted coconut oil (50° C.) was mixed with carotenoids, then this was mixed into the water. The broth was vigorously stirred, then quickly the wheat gluten flour was added to the broth and mixed well with a spoon. The formed raw meat dough was transferred to a metal ramekin or glass beaker for steaming as described in Example 16 and then transferred to a container on ice to allow it to cool down to 4° C.

The addition of carotenoids modified the flavor of the dough in an advantageous way; when compared to the meat dough with no carotenoids (Example 10), five trained flavor scientists described the meat dough with carotenoid as having less grain flavor, less oxidized notes, and overall less off flavors in four tastings. Table 8 presents the summarized sensory results from a panel of samples with different carotenoids evaluated by five trained flavor scientist on grain flavor. The trained flavor scientists rated the samples from 1-5 on the grain flavor, with 1 being the lowest in grain flavor and 5 being the highest. The reduction in off flavors in the meat dough with the lutein was supported by SPME Gas chromatography-mass spectrometry (GC-MS) data. Additionally, carotenoids (lycopene, beta-carotene, zeaxanthin, canthaxanthin, and lutein) added to the meat dough resulted in the samples being described as more fatty and sweeter.

With the addition of lutein in the meat dough, most flavor compounds decreased dependent on the concentration of lutein. See Table 9 shown in FIG. 1; lutein concentrations were at none, 0.0005%, and 0.005%. The main compounds that decreased with the carotenoids included oxidized flavor compound like alcohols and aldehydes, including (Z)-2-nonenal, (E,E)-2,4-nonadienal, and 1-penten-3-ol; additionally, sulfur compounds were decreased, including methanethiol, 2-acetylthiazole, and dimethyl sulfide; many of these compounds also were described as grainy and oxidized notes by trained flavor scientist by Gas Chromatography-Olfactometry (GCO).

TABLE 8

| Sensory emulation of meat dough with the addition of carotenoids for reduction in grain flavor | |
|---|---|
| Meat dough with: | Grain ranking: 1-5 (1 = lowest) |
| Control coconut oil blank | 3.0 ± 0.8 |
| plus Lycopene | 2.8 ± 0.6 |
| plus beta-carotene | 1.5 ± 0.7 |
| plus Zeaxanthin | 1.6 ± 0.8 |
| plus Canthaxanthin | 1.6 ± 0.8 |
| plus lutein | 1.9 ± 0.8 |

Example 19

Decreased Grain and Off Flavor by the Addition of Antioxidants

A meat dough was prepared as follows using the ingredients shown in Table 10.

TABLE 10

| Composition of Meat Dough | |
|---|---|
| Ingredient | % |
| Gluten flour (ADM PROLITE ® Low Flavor Vital Wheat Gluten) | 40.0 |
| Tap water | 50.0 |
| Coconut oil | 9.95 |
| EGCG (Swanson Superior Herbs) | 0.05 |
| Total | 100.0 |

EGCG (epigallocatechin gallate) was solubilized in water, then melted coconut oil (50° C.) was mixed into the water. The broth was vigorously stirred, then quickly the wheat gluten flour was added to the broth and mixed well with a spoon. The formed raw meat dough was transferred to a metal ramekin or glass beaker for steaming as described in Example 16, and then transferred to a container on ice to allow it to cool down to 4° C.

The reduction in off flavors as described by trained flavor scientists in the meat dough with the addition of EGCG is supported by SPME GC-MS data. The GCMS data showed multiple flavor compounds that were no longer detectable or decreased by at least 2-fold, including compounds 2-pentylfuran, 6-methyl-5-hepten-2-one, 1-penten-3-ol, 2-penten-1-ol, methyl-pyrazine, butanal, 5-ethyl-2(5H)-furanone, 5-ethyldihydro-2(3H)-furanone, 2-nonenal, phenylacetaldehyde, and 3,5-octadien-2-one that were described by GCO as being grainy and oxidized notes.

Example 20

Preparation of Meat Dough with Decreased Grain Flavor by Washing the Wheat Gluten Meat dough was prepared as follows using the ingredients shown in Table 11.

TABLE 11

Composition of Meat Dough

| Ingredient | % |
|---|---|
| Gluten flour | 40.0 |
| Tap water | 50.0 |
| Coconut oil | 10 |
| Total | 100.0 |

Wheat gluten flour (ADM PROLITE® Low Flavor Vital Wheat Gluten) was slowly stirred into a solution that contained 10× washing solution (50 mM NaCl), then mixed well to prevent clump formation. The solution was set on ice for five minutes, during which the wheat gluten settled to the bottom. A second wash step was followed by removing the first wash solution and stirring into 10× fresh washing solution. The second solution was discarded and a final wash with tap water followed. The water wash solution was discarded, then the washed wheat gluten was measured to determine that the correct amount of water was incorporated. Water was added or pressed out so that the wheat gluten dough weight was equal to the amount of initial wheat gluten flour measured out and the theoretical amount of water. Melted coconut oil was added, and the dough was hand kneaded for 30 seconds to incorporate the oil. The formed raw meat dough was transferred to a metal ramekin or glass beaker for steaming as in Example 16 and then transferred to a container on ice to allow it to cool down to 4° C.

The washing step modified the flavor of the dough in an advantageous way; when compared to the non-washed meat dough, five trained flavor scientists described the washed meat dough as having less grain flavor, less oxidized notes, and overall less off flavors in four tastings. The reduction in off flavors in the washed meat dough is supported by SPME GC-MS coupled with GCO that compared non-washed to washed meat dough. In the washed meat dough, flavor compounds decreased, including oxidized flavor compounds such as alcohols and aldehydes, and particular compounds including 1-(2-furanyl)-ethanone, methyl-pyrazine, pentanoic acid, 3-methyl-1-butanol, 2,3-butanedione, benzyl alcohol, (E,E) 3,5-octadien-2-one, (E)-2-nonenal, (E,E)-2,4-decadienal, and 1-octen-3-one, which were determined to be odor active compounds by GCO and the detection of these compounds was either decreased or was not detected in the washed meat dough.

Example 21

Preparation of Bloody Agar

Bloody agar was prepared using the ingredients shown in Table 12.

TABLE 12

Composition of Bloody Agar

| Ingredient | % |
|---|---|
| Flavor broth | 41.5 |
| Leghemoglobin, 50 mg/ml liquid | 26.7 |
| 17× Liquid Magic Mix | 17.3 |
| RuBisCO, dry (Example 2) | 12.0 |
| 1M lactic acid solution | 1.5 |
| Agar powder | 1 |
| Total | 100.0 |

Agar powder (Now Foods, Bloomingdale, Ill.) was dissolved in a mixture of lactic acid and flavor broth (made as in Example 5, except 10% coconut oil and Magic Mix 1 from Table 13 was used) by heating to 100° C. in a stirred beaker. The solution was cooled to 65° C. by immersion in an ice bath. 17× liquid magic mix (Magic Mix 2 from Table 13) and leghemoglobin, both at 4° C., then were added, causing the temperature of the mixture to decrease to 50° C. It is important that the mixture be cooled before adding the leghemoglobin to prevent the leghemoglobin from denaturing. The dry RuBisCO then was added and the mixture was stirred vigorously by hand. It is important that the temperature be between 40° C. and 60° C. when the RuBisCO is added. If the temperature is too high, the RuBisCO can denature and will not function as a firming agent during cooking of the final product. If the temperature is too low, the agar will solidify and hinder generation of a homogenous mixture.

TABLE 13

Composition of Magic Mixes

| Precursor | Precursor mix 1 (mM) | Precursor mix 2 (mM) |
|---|---|---|
| Alanine | 15.0 | 7.5 |
| Arginine | 0.6 | 0.3 |
| Asparagine | 0.8 | 0.4 |
| Aspartate | 0.8 | 0.4 |
| Cysteine | 9.0 | 9.0 |
| Glutamic acid | 20 | 20 |
| Glutamine | 0.7 | 0.3 |
| Glycine | 1.3 | 0.7 |
| Histidine | 0.6 | 0.3 |
| Isoleucine | 0.8 | 0.4 |
| Leucine | 2.0 | 1.0 |
| Lysine | 5.0 | 2.5 |
| Methionine | 1.0 | 0.5 |
| Phenylalanine | 0.6 | 0.3 |
| Proline | 0.9 | 0.4 |
| Threonine | 0.8 | 0.4 |
| Tryptophan | 1.5 | 0.8 |
| Tyrosine | 0.6 | 0.3 |
| Valine | 1.0 | 0.5 |
| Glucose | 5.6 | 2.8 |
| Ribose | 5.0 | 5.0 |
| Thiamine | 0.2 | 0.2 |
| IMP + GMP | 2.5 | 1.3 |
| Lactic acid | 10.0 | 5.0 |
| Creatine | 3.0 | 1.5 |
| L-Taurine | 10.0 | 5.0 |

Example 22

Preparation of Bloody Agar

Bloody agar was prepared using the ingredients shown in Table 14.

TABLE 14

Composition of Bloody Agar

| Ingredient | % |
| --- | --- |
| Water | 81.1 |
| 1M lactic acid solution | 9.2 |
| 17x Liquid Magic Mix (Table 12) | 4.4 |
| Leghemoglobin, 87 mg/ml liquid | 4.3 |
| Agar powder | 1.0 |
| Total | 100.0 |

Agar powder (Agar 100, TIC Gums, White Marsh, Md.) was dissolved in a mixture of water and lactic acid by heating to at least 91° C. in a stirred beaker. Heating was done to fully solubilize the agar. The solution then was cooled to 50-70° C. and a premixture of the leghemoglobin (*Pichia* expressed, Example 1) and 17× Liquid Magic mix (Table 12) was added. If the temperature is too high, the leghemoglobin can denature and will not function as intended for flavor reaction chemistry. If the temperature is too low, the agar will solidify and hinder generation of a homogenous mixture. The mixture then was stirred and further cooled to 4-25° C. The finished product has a ketchup like appearance and texture.

Example 23

Preparation of Adipose Replica Emulsion with Improved Melting, Adhesive and Mouth Feel Properties To prepare one hundred (100) g of adipose replica, 1 g of dry precursor mix 1 (Table 12) was dissolved in 18.8 ml of water and the pH was adjusted to 6 with a concentrated NaOH solution. A frozen solution of leghemoglobin (5.5%) was added to the precursor solution and placed on a stirring hot plate maintained at 160° C., with a 250 RPM rotation speed.

In a separate container, thirty five (35) g of coconut oil (Shay and company, Milwaukie, Oreg.) and thirty five (35) g of palm stearin were melted together in a 60° C. water bath. The melted oil mixture was slowly (about 12 ml/min) added to the solution of precursors and leghemoglobin, while increasing the stirring rate to 450 RPM.

The resulting thick emulsion was maintained at the same temperature and stirring rate for 23 min after the oil was added. The emulsion then was transferred to a 600 ml beaker and placed on ice and into the refrigerator for rapid cooling. When the emulsion reached 25° C., 0.35 g of algal vegetable oil and 0.35 g of acetoin were added to the emulsion and rapidly mixed in with a spatula. Lactones for improved flavor and masking off-flavors (as described in Example 31) were added in the following amounts: 5-ethyl-4-hydroxy-2-methyl-3(2H)-furanone was added to a final concentration of $2.5*10^{-5}\%$, butyrolactone was added to a final concentration of $2.5*10^{-8}\%$, and δ-tetradecalactone was added to a final concentration $5*10^{-9}\%$. The emulsion was homogenized for 2.5 min using a hand-held homogenizer at setting 6. The emulsion was incubated at 4° C. until it was fully solid.

After solidification, the adipose replica emulsion was off-white to a slightly browned color, waxy solid at room temperature, with flavors that were characterized as savory, meaty, bloody, and chicken fat-like. When incorporated into the ground beef replica, the stickiness of the replica was increased as was the ability of the replica to be handled and shaped.

Example 24

Preparation of Adipose Replica Emulsion Stabilized by Soy Conglycinin Protein To prepare 100 g of adipose replica, 1.5 g of isolated soy conglycinin powder from Example 4 was dissolved in 28.5 ml of water and placed on a hot stir plate. In a separate container, 70 g of coconut oil (Shay and company) were melted in a 60° C. water bath. The melted oil mixture was slowly (about 12 ml/min) added to the solution of purified protein under constant stirring. The resulting emulsion was heated up to 90° C. temperature and maintained at this temperature for 5 min. The emulsion then was transferred to a 600 ml beaker and placed on ice and into the refrigerator for rapid cooling. When the emulsion reached 25° C., 0.35 g of algal vegetable oil were added to the emulsion and rapidly mixed in with a spatula. Lactones for improved flavor and masking off-flavors (as described in Example 31) were added in the following amounts: 5-ethyl-4-hydroxy-2-methyl-3(2H)-furanone was added to a final concentration of $2.5*10^{-5}\%$, butyrolactone was added to a final concentration of $2.5*10^{-8}\%$, and δ-tetradecalactone was added to a final concentration $5*10^{-9}\%$. The emulsion was homogenized for 2.5 min using a hand-held homogenizer at setting 6 and incubated in the 4° C. refrigerator until it was fully solid. After solidification, the adipose replica emulsion was white to slight off-white color, solid at room temperature, with bland, very neutral flavor and texture characterized as similar to rendered beef fat.

Example 25

Preparation of Adipose Replica Emulsion Stabilized by Soy Conglycinin Protein by a pH Excursion Method To prepare 100 g of adipose replica, 0.5 g of isolated soy glycinin protein powder from Example 4 was dissolved in 29.5 ml of water in a beaker. The pH of the protein solution was adjusted to 12 using a 2 M solution of sodium hydroxide. In a separate container, 70 g of coconut oil (Shay and company) were melted in a 60° C. water bath. The melted oil mixture was slowly (about 12 ml/min) added to the solution of purified protein under constant stirring. 0.35 g of algal vegetable oil were added to the emulsion and rapidly mixed in with a spatula. The pH of the protein solution was adjusted to 12 using a 2 M solution of sodium hydroxide, and the emulsion was homogenized for 30 s (thirty seconds) using a hand-held homogenizer at setting 6 and incubated at 4° C. until it was fully solid. After solidification, the adipose replica emulsion was white to slight off-white color, solid at room temperature, with bland, very neutral flavor and cottage cheese-like texture.

Example 26

Adding Carotenoids in Flavor Emulsion to Increase Meaty Flavors

Each carotenoid (canthaxanthin, β-carotene, lutein, or lycopene) (Shay and company, Milwaukie, Oreg.) was individually dissolved in coconut oil or water at 10%, dependent on solubility. The carotenoids were added to the flavor emulsion before cooking by mixing a solution of LegH at 0.5%, lx precursor mix 1 (Table 1), 30% RBD coconut oil, and the individual 10% carotenoid solutions (final carotenoid concentration in emulsion was 0.025%), and stirring the mixture as it was heated until boiling, then simmered at a low boil for 10 minutes. Additional algal vegetable oil at 0.7% was added for additional precursors for flavor creation as described in Example 32. Lactones for improved flavor and masking off-flavors (as described in Example 31) were added in the following amounts: 5-ethyl-4-hydroxy-2-methyl-3(2H)-furanone was added to a final concentration of $2.5*10-5\%$, butyrolactone was added to a final concentration of $2.5*10-8\%$, and δ-tetradecalactone was added to a final concentration $5*10-9\%$. The emulsion was homogenized for 2.5 min using a hand-held homogenizer at setting 6 then incubated at 4° C. until it was fully solid. The emulsions were then added to the taco meat prepared as described in Example 30. The samples then were compared with the different carotenoids to a control with no carotenoids added. The samples were evaluated by at least five trained flavor scientists. The results are summarized in Table 15.

TABLE 15

Flavor descriptions from tacos tasted with flavor emulsion prepared with different carotenoids

| Carotenoid | Summary - common | Summary - unique |
| --- | --- | --- |
| canthaxanthin | more brown (2)[§], similar to control (2), lower green floral/veg (2), toasted grain (2), more fatty (2), odd/chemical/vitamin (2) | sweet, more beefy, less grain, sl* floral |
| β-carotene | more meaty/beefy (3), more fatty (2), less green/floral off, less chickeny | more savory, less savory, sl bitter, sl carrot, sl bland |
| lutein | similar to control (3), more brown (2) | lower green floral, floral, cardboard/grain, more butter, vegetable stock, pleasant, no off flavors |
| lycopene | fatty (2), grain (3) | lower green/floral/grain, more vegetable, less meaty, less off, savory, same as control |

*slightly
[§]Numbers in parentheses indicate the number of tasters with that response.

Example 27

Assembly and Cooking of Burger

A replica burger containing the ingredients in Table 16 was prepared.

TABLE 16

Composition of Burger

| Ingredient | % |
| --- | --- |
| Meat dough (Example 16) | 26.9 |
| Bloody agar (Example 21) | 33.9 |
| Flavored emulsion (Example 21) | 20.0 |
| Soft connective tissue (Example 7) | 19.2 |
| Total | 100.0 |

Chilled meat dough was ground using a stand mixer fitted with a food grinder attachment (KITCHENAID® Professional 600 Series 6 Quart Bowl-Lift Stand Mixer model KP26M1XER and KITCHENAID® Food Grinder model FGA, St. Joseph, Mich.) on speed setting 1. In this equipment, material is fed by a screw conveyor past a rotating knife installed in front of a fixed-hole plate. Soft connective tissue was shredded using a Universal Machine (UM-12, Stephen Machinery GmbH, Schwarzenbeck, Germany) fitted with a blunt blade and run for 20-30 seconds at slow speed. Flavored emulsion was chilled to −20° C. and then chopped with a mini chopper (Mini-Prep® Plus Processor model DLC-2L Cuisinart, Stamford, Conn.) in a single step process. Approximate 400 g of emulsion was placed in the mini chopper and processed on the chop setting for 60 seconds to yield pieces of 1-3 mm in length.

Ground meat dough, shredded soft connective tissue, and flavored emulsion pieces were then mixed. During mixing, the mixture was kept at −5 to 4° C. to prevent the fat from melting. The bloody agar was then added and mixed until it was thoroughly incorporated. The total batch size was 1 kg. 50 g or 150 g portions of ground tissue then were formed by hand into round patty shapes. Typical dimensions for 50 g patties were 55 mm×15 mm. Typical dimensions for 150 g patties were 100 mm×22 mm. Patties were refrigerated until cooked. Patties were cooked on a preheated (325-345° F.) non-stick skillet and heated to an internal temperature of 160° F. while flipping every 2 minutes. Cooked patties had an appearance, texture, and flavor similar to ground beef. In addition to cooking in patty format, the unformed material also can be used in a variety of dishes such as taco filling, casseroles, sauces, toppings, soups, stews, or loaves.

Example 28

Assembly and Cooking of Burger

A replica burger containing the ingredients in Table 17 was prepared.

TABLE 17

Composition of Burger

| Ingredient | % |
| --- | --- |
| Meat dough (Example 17) | 26.8 |
| Fat emulsion (Example 23) | 20 |
| Soft connective tissue (Example 7) | 19.2 |
| Bloody agar (Example 22) | 13.0 |
| Hydration liquids | 10.5 |
| Soy conglycinin, dry | 10.5 |
| Total | 100.0 |

Chilled meat dough was ground using a stand mixer fitted with a food grinder attachment (KITCHENAID® Professional 600 Series 6 Quart Bowl-Lift Stand Mixer model KP26M1XER and KITCHENAID® Food Grinder model FGA, St. Joseph, Mich.) on speed setting 1. Soft connective tissue was shredded using a Universal Machine (UM-12, Stephan Machinery GmbH, Schwarzenbeck, Germany) fitted with a blunt blade and run for 20-30 seconds at slow speed. Flavored emulsion was chilled to −20° C. and then chopped with a SALADSHOOTER® National Presto Industries, Inc. Eau Claire, Wis.) to yield pieces of 1-3 mm in length. Ground meat dough, shredded soft connective tissue, flavored emulsion pieces, and dry soy conglycinin were then mixed. During mixing, the mixture was kept at −5 to 4° C. to prevent the fat from melting. Hydration liquids (a 1:1 mixture of leghemoglobin and 17× Liquid Magic mix as described in Example 22) were then added and the mixture was held at 4° C. for a minimum of 15 minutes to allow the dry soy conglycinin to hydrate. Finally bloody agar was added and mixed until it was thoroughly incorporated. The total batch size was 200 g. 50 g portions of ground tissue then were formed by hand into round patty shapes. Typical dimensions for 50 g patties were 55 mm×15 mm. Patties were refrigerated until cooked. Patties were cooked on a preheated (325-345° F.) non-stick skillet and heated to an internal temperature of 170° F. while flipping every minute. Cooked patties had an appearance, texture, and flavor similar to ground beef. In addition to cooking in patty format, the unformed material also can be used in a variety of dishes such as taco filling, casseroles, sauces, toppings, soups, stews, or loaves.

Example 29

Assembly and Cooking of Burger with 10% Meat Dough

A replica burger containing the ingredients in Table 18 was prepared.

TABLE 18

| Composition of Burger | |
|---|---|
| Ingredient | % |
| Meat dough (Example 17) | 10 |
| Fat emulsion (Example 23) | 20 |
| Soft connective tissue (Example 7) | 36 |
| Bloody agar (Example 22) | 13.0 |
| Hydration liquids | 10.5 |
| Soy conglycinin, dry | 10.5 |
| Total | 100.0 |

Chilled meat dough was ground using a stand mixer fitted with a food grinder attachment (KITCHENAID® Professional 600 Series 6 Quart Bowl-Lift Stand Mixer model KP26M1XER and KITCHENAID® Food Grinder model FGA, St. Joseph, Mich.) on speed setting 1. Soft connective tissue was shredded using a Universal Machine (UM-12, Stephan Machinery GmbH, Schwarzenbeck, Germany) fitted with a blunt blade and run for 20-30 seconds at slow speed. Flavored emulsion was chilled to −20° C. and then chopped with a SALADSHOOTER® National Presto Industries, Inc. Eau Claire, Wis.) to yield pieces of 1-3 mm in length. Ground meat dough, shredded soft connective tissue, flavored emulsion pieces, and dry soy conglycinin were then mixed. During mixing, the mixture was kept at −5 to 4° C. to prevent the fat from melting. Hydration liquids (a 1:1 mixture of leghemoglobin and 17× Liquid Magic mix as described in Example 22) were then added and the mixture was held at 4° C. for a minimum of 15 minutes to allow the dry soy conglycinin to hydrate. Finally, bloody agar was added and mixed until it was thoroughly incorporated. The total batch size was 200 g. Fifty (50) g portions of ground tissue then were formed by hand into round patty shapes. Typical dimensions for 50 g patties were 55 mm×15 mm. Patties were refrigerated until cooked. Patties were cooked on a preheated (325-345° F.) non-stick skillet and heated to an internal temperature of 170° F. while flipping every minute. Cooked patties had an appearance, texture, and flavor similar to ground beef. In addition to cooking in patty format, the unformed material also can be used in a variety of dishes such as taco filling, casseroles, sauces, toppings, soups, stews, or loaves.

Example 30

Assembly and Cooking of "Taco Meat"

A replica "taco meat" containing the ingredients in Table 19 was prepared.

TABLE 19

| Composition of Burger | |
|---|---|
| Ingredient | % |
| Meat dough (Example 17) | 29.9 |
| Fat emulsion (Example 23) | 22.3 |
| Soft connective tissue (Example 7) | 21.5 |
| Bloody agar (Example 22) | 14.5 |
| Hydration liquids | 11.7 |
| Total | 100.0 |

Chilled meat dough was ground, soft connective tissue was shredded, and the flavored emulsion was chopped as described in Example 28. Ground meat dough, shredded soft connective tissue, and flavored emulsion pieces were then mixed. During mixing, the mixture was kept at −5 to 4° C. to prevent the fat from melting. Hydration liquids (a 1:1 mixture of leghemoglobin and 17× Liquid Magic mix as described in Example 22) and bloody agar was then added and mixed. The total batch size was 20 g. The mixed tissue was then cooked on a preheated (325—345° F.) non-stick skillet to 160° F. Cooked tissue had an appearance, texture, and flavor similar to ground beef. The material resembled taco meat in appearance; without the 7S protein, the meat did not firm up and stick together as much.

Example 31

Using Lactones as Masking Agents

Lactones were diluted in either water or oil depending on solubility. The diluted lactones were then added to the flavored emulsion (Example 23) as indicated in Table 20 and homogenized. The final concentrations of the lactones are given in Table 20. The flavored emulsion was added for a final of 20% of the ground meat (e.g., taco meat) (all components of the meat replica without RuBisCO). The flavored emulsion was mixed with meat dough, connective tissue, magic mix, and heme as indicated in Example 17 but without the RuBisCO. The ground meat was then tested by five trained flavor scientists for overall taste, any reduction in off flavors, and overall improvement. The summarized results are indicated in Table 20. The addition of particular lactones and combinations of lactones resulted in a decrease in off flavors including grain, eggy, bitterness, livery, and mushroom. Unique combinations were required for particular masking properties like bitterness. The lactones also increased desired flavors of creamy, buttery, caramelized, fatty, fresh, and fruity.

TABLE 20

Sensory data on addition of lactones as masking agents in meat replicas

| Compound | Conc. (%) in Meat Tested | Compound | Conc. (%) in Meat Tested | Compound | Conc. (%) in Meat Tested | % of testers who preferred over control | Common Flavor Descriptors | Masks or prevents off flavors? |
|---|---|---|---|---|---|---|---|---|
| Butyrolactone | $2.5*10^{-9}$ | y-Octalactone | $2.5*10^{-8}$ | — | — | 80% | Sour, savory | Bitterness |
| Delta-Tridecalactone | $2.5*10^{-5}$ | 5-Ethyl-4-hydroxy-2-methyl-3(2H)-furanone | $2.5*10^{-6}$ | — | — | 75% | Salty, savory, creamy/buttery | Bitterness |
| 2(3H)-Furanone, Dihydro-5-Methyl | $2.5*10^{-8}$ | 5-Ethyl-4-hydroxy-2-methyl-3(2H)-furanone | $2.5*10^{-6}$ | — | — | 75% | Bland, fatty, salty | Bitterness, grain |
| 2(3H)-Furanone, Dihydro-5-Methyl | $2.5*10^{-8}$ | 5-Ethyl-4-hydroxy-2-methyl-3(2H)-furanone | $2.5*10^{-6}$ | Delta-Tridecalactone | $2.5*10^{-6}$ | 83% | Buttery, fatty, bright/bitter, savory | Eggy, grain |
| 2(3H)-Furanone, Dihydro-5-Methyl | $2.5*10^{-8}$ | 5-Ethyl-4-hydroxy-2-methyl-3(2H)-furanone | $2.5*10^{-6}$ | Delta-Tridecalactone | $2.5*10^{-6}$ | 83% | Sl sweet, fatty | Grain |
| Butyrolactone | $2.5*10^{-8}$ | 5-Ethyl-4-hydroxy-2-methyl-3(2H)-furanone | $2.5*10^{-6}$ | y-Octalactone | $2.5*10^{-7}$ | 83% | Creamy, metallic | Eggy |
| Gamma Decalactone | $5*10^{-5}$ | | | | | 40% | Caramelized/aromatic sweet, salty | Grain |
| Delta-Tridecalactone | $5*10^{-5}$ | | | | | 60% | Caramelized/aromatic sweet | Mushroom |
| Delta-dodecalactone | $1*10^{-5}$ | | | | | 60% | Buttery, fatty/oily, sl beefy | Grain |
| 4-hydroxy-2,5-dimethyl-3(2H)-furanone | $1*10^{-5}$ | | | | | 60% | Sl sweet/caramelized | Grain |
| y-Octalactone | $1*10^{-5}$ | | | | | 80% | Fatty, sweet/caramelized | Grain |
| Butyrolactone | $2.5*10^{-8}$ | | | | | 83% | Bright/sharp/bitter, sweet, fatty | Eggy |
| δ-Tetradecalactone | $5*10^{-9}$ | | | | | 83% | Brothy, fatty | Eggy, grain |
| 2(3H)-Furanone, Dihydro-5-Methyl | $5*10^{-9}$ | | | | | 100% | Mild savory, slight sweet | Eggy, grain |

Example 32

Adding Polyunsaturated Fats for the Creation of Meaty Fat Flavor

Algal vegetable oil (DSM life's omega 45 02412-0100) was added to the flavored emulsion (Example 23), and then homogenized, for a final concentration of 0.07% in the meat replica. The flavor emulsion was added to the replica as described in Example 27. The addition of algal vegetable oil resulted in a replica with an increase in tallow taste, fattiness, and overall meatiness, as described by trained flavor scientists.

The addition of algal oil increased the precursors including eicosapentaenoic acid and docosahexaenoic acid that are needed for the creation of fatty flavor molecules. As detected by SPME Gas chromatography-mass spectrometry (GC-MS), the addition of algae oil to the precursor mix and hemoglobin as compared to the control without algal oil created flavors including nonane, (E,E)-3,5-octadien-2-one, 1-hepten-3-ol, 1-penten-3-one, 2-propyl furan, n-caproic acid vinyl ester, 3-ethyl-2-methyl-1,3-hexadiene, 1-ethyl-5-methylcyclopentene, trans-2-(2-pentenyl)furan, 1-penten-3-ol, 4,7-dimethyl-undecane, 1-octanol, 3-ethyl-pyridine, 3-ethylcyclopentanone, (Z)-2-octen-1-ol, 2-n-heptylfuran, (Z)-2-decenal, hexanoic acid, (E,E)-2,4-nonadienal, 6-methyl-2-heptanone, (Z)-2-heptenal, (E,E)-2,4-heptadienal, 1-hexanol, (E,E)-2,4, decadienal, (E,Z)-2,6-nonadienal, and 1-octen-3-ol.

Example 33

Creating *Cucumis* Slurries for Meat Replicas

To create a boiled cucumber slurry, an entire non-permeated crisp variety cucumber (with the skin not peeled off or otherwise disrupted) was used. A water bath was heated to 80-90° C., and the entire cucumber was placed into the water bath and cooked until the internal temperature of the cucumber was equilibrated with the temperature of the water bath, around 30 minutes for this example. The cucumber then was taken out of the bath and the skin of the cucumber was completely removed from the flesh. The flesh was blended with the seeds and then sieved to separate out any of the larger particulates. The blended flesh then was used as the slurry and added to the meat replicas. This same method was used with other varieties in the *Cucumis* genus including honeydew melon and cantaloupe.

Example 34

Creating *Cucumis* Extracts Using Solvent Assisted Flavor Extraction

An extract was created using solvent assisted flavor extraction (SAFE), and water as the solvent. SAFE works by pulling the flavor compounds out of the material with pressure and a slightly elevated temperature.

An extract was created by removing all the skin of a crisp variety cucumber, and cutting the cucumber into pieces then blended with a magic bullet. The cucumber slurry was then poured into the sample inlet of the SAFE glassware that was under pressure using an Edwards 12 floor vacuum, and the temperature was set at 40° C. with a water pump, and a warm water-bath for the sample round bottom flask. A small amount (2-4 mL of sample) of the cucumber slurry was put in the sample round bottom flask. The slurry immediately appeared to boil as it traveled into the sample round bottom flask. When the visual boiling stopped, more sample volume was added to the sample round bottom flask. This continued until the entire sample was let into the SAFE glassware setup. Once the entire sample was gone, the sample keep extracting as the water bath reach 40° C. then extracted for additional 20 minutes. As the extract was taking place the collection round bottom flask was submerged in liquid nitrogen and cold finger inlet filled with liquid nitrogen. The extract was then collected from the collection round bottom flask.

Example 35

Adding *Cucumis* Liquid to Meat Replicas to Increase Meatiness and Fattiness by Adding to Gelled Matrix Bloody agar as outlined in Example 22 was made as described other than with the addition of *Cucumis* liquid replacing DI water. The *Cucumis* liquid was one of the following: (i) a commercially available water extract from a cantaloupe melon, added at 2% of the DI water, (ii)-(v) a slurry, cooked or not cooked, of either honeydew melon (6.25%) or cucumber (3.2%) as described in Example 33, or (vi) solvent assisted flavor extract of cucumber (pressure distillate) as described in Example 34. The addition of these cucumber and melon extracts brings certain elements of a meaty flavor profile to enhance the overall preferences and meatiness of replicas. As demonstrated by SPME GC-MS, and confirmed as odor active compounds by trained flavor scientist using GCO, many of the compounds are aldehydes, lactones, many of which are seen in beef. Compounds that are similar between beef and *Cucumis* include, without limitation, nonanal, 2-decenal, 2-nonenal, 2-heptenal, 2,6-nonadienal, 2,4-decadienal, 2-undecenal, 2-octenal, 2-nonenal, dodecanal, 2,4-heptadienal, 2,6-nonadienal, 2,4-nonadienal, 2,4-octadienal, decanal, 5-(methylenecyclopropyl)-pentanal, 6-nonenal, 3,7-dimethyl 1,6-octadien-3-ol, 2-nonen-1-ol, 3-nonen-1-ol, 3,5-octadien-2-one, 2,3-butane-dione, 2-methyl-cyclopentanone, 2-butanone, á-ionone, 6-octen-2-one, dihydro-5-pentyl-2(3H)-furanone, 1-menthone, n-caproic acid vinyl ester, 4-methyloctanoic acid, and acetic acid ethenyl ester.

When the bloody agar with the extracts were added to meat replicas as described in Example 30, there was an increase in sweet aromatics, fattiness, and in some cases tallow and beefy flavors, see Table 21 for the full description from five trained flavor scientist of additional flavor notes that were not seen in the control and blind control. Additionally, it was observed that the addition of these melon and cucumber extracts also decreases the perception of off flavors including grainy, earthy, woody, and astringent.

Three of these extracts were tested in a formal descriptive panel with 8 trained panelists and compared to one control replica indicated as such, a blind control not indicated as a control, 80:20 beef, and three additional samples with the *Cucumis* liquid (cooked cucumber slurry tested at 0.37% of the final taco meat, cooked honeydew slurry tested at 0.73% of the final taco meat, and Cantaloupe extract (from TRE-ATT) at 0.24% of the final taco meat). The results showed that all three samples were rated as higher in fattiness and sweet aromatics, with a decrease in off notes of earthy, grainy, astringent, and green. The cantaloupe extract had an additional off note from the control of a sweet melon flavor unlike what is tasted in beef. The other two samples the cooked honeydew slurry and cucumber slurry made as described in Example 33, were both rated as higher in meatiness and fattiness than both controls, and had no additional off notes described.

TABLE 21

Flavor descriptions from adding *Cucumis* liquid to meat replicas

| *Cucumis* liquid | Flavor Description when added to tacos | |
|---|---|---|
| | Increase in desirable flavors | Decrease in undesirable flavors |
| Cooked honeydew slurry | Fatty, butter, fresh, sweet, mouthwatering, and fatty mouth coating | Green, grain, earthy |
| Cooked cucumber slurry | Beef tallow, more buttery, fatty, fresh, fruit, fatty mouth coating | Green, grain, earthy |
| Honeydew slurry | Savory, melon, slight butter, pork, sweet aromatic, fatty, mouthwatering, mouth coating | Green, grain, earthy |
| Cucumber slurry | Fruity, fatty, cucumber, vegetable stock and melon | Green, grain, earthy |
| Cantaloupe extract | Sweet, fruity, aromatic, slight butter, melon, candy | Green, grain, earthy |
| Cucumber SAFE | Less chicken, freshness, sweet, little cucumber | Green, grain, earthy |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant *Pichia pastoris* organism comprising:
    eight stably integrated genes encoding recombinant heme biosynthesis enzymes; and
    a stably integrated nucleic acid encoding a recombinant heme-containing protein selected from leghemoglobin and myoglobin,
    wherein the heme biosynthesis enzymes are *Pichia pastoris* ALA synthase, *Pichia pastoris* ALA dehydratase, *Pichia pastoris* porphobilinogen deaminase, *Pichia pastoris* uroporphyrinogen III synthase, *Pichia pastoris* uroporphyrinogen III decarboxylase, *Pichia pastoris* coproporphyrinogen oxidase, *Pichia pastoris* protoporphyrinogen III oxidase, and *Pichia pastoris* ferrochelatase.

2. The recombinant *Pichia pastoris* organism of claim 1, wherein at least one of the eight genes and/or the recombinant heme-containing protein is expressed by a methanol inducible promoter.

3. The recombinant *Pichia pastoris* organism of claim 2, wherein the methanol inducible promoter is pAOXI.

4. The recombinant *Pichia pastoris* organism of claim 1, wherein the heme-containing protein is a mammalian myoglobin.

5. The recombinant *Pichia pastoris* organism of claim 1, wherein the heme-containing protein is a *Glycine max* leghemoglobin.

6. A method of producing a consumable heme-containing protein, the method comprising:
fermenting the recombinant *Pichia pastoris* organism of claim 2 in a fermentation broth, and inducing expression of the heme-containing protein with methanol.

7. The method of claim 6, comprising centrifuging cells of the *Pichia pastoris* organism expressing the heme-containing protein.

8. The method of claim 6, comprising lysing cells of the *Pichia pastoris* organism expressing the heme-containing protein to produce a cell lysate.

9. The method of claim 8, comprising filtering the cell lysate to produce a soluble lysate.

10. The method of claim 9, comprising concentrating the heme-containing protein in the soluble lysate.

11. The method of claim 6, comprising centrifuging cells of the *Pichia pastoris* organism expressing the heme-containing protein, lysing cells of the *Pichia pastoris* organism expressing the heme-containing protein to produce a cell lysate, filtering the cell lysate to produce a soluble lysate, and concentrating the heme-containing protein in the soluble lysate.

12. The method of claim 6, wherein the heme-containing protein is a mammalian myoglobin.

13. The method of claim 6, wherein the heme-containing protein is a *Glycine max* leghemoglobin.

14. A method for preparing a food additive comprising recombinant heme-containing protein, the method comprising:
providing a recombinant *Pichia pastoris* organism comprising: eight stably integrated genes encoding recombinant heme biosynthesis enzymes; and a stably integrated gene encoding a recombinant heme-containing protein selected from leghemoglobin and myoglobin under the control of a methanol inducible promoter, wherein the recombinant heme biosynthesis enzymes comprise *Pichia pastoris* ALA synthase, *Pichia pastoris* ALA dehydratase, *Pichia pastoris* porphobilinogen deaminase, *Pichia pastoris* uroporphyrinogen III synthase, *Pichia pastoris* uroporphyrinogen III decarboxylase, *Pichia pastoris* coproporphyrinogen oxidase, *Pichia pastoris* protoporphyrinogen III oxidase, and *Pichia pastoris* ferrochelatase;
fermenting the recombinant *Pichia pastoris* organism in a fermentation broth;
inducing expression of the heme-containing protein with methanol;
purifying the recombinant heme-containing protein; and
combining the purified recombinant heme-containing protein with a buffered solution.

* * * * *